(12) United States Patent
Agarwal et al.

(10) Patent No.: US 12,083,242 B2
(45) Date of Patent: *Sep. 10, 2024

(54) ALGINATE BASED PARTICLES AS A TEMPORARY EMBOLIC AGENT

(71) Applicant: CrannMed Limited, Galway (IE)

(72) Inventors: Sankalp Agarwal, Nagpur (IN); Masum Pandey, Nagpur (IN); Andrew Lewis, Galway (IE)

(73) Assignee: CrannMed Limited, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/794,072

(22) PCT Filed: Mar. 2, 2022

(86) PCT No.: PCT/IB2022/051852
§ 371 (c)(1),
(2) Date: Jul. 20, 2022

(87) PCT Pub. No.: WO2022/185235
PCT Pub. Date: Sep. 9, 2022

(65) Prior Publication Data
US 2023/0405179 A1 Dec. 21, 2023

(30) Foreign Application Priority Data
Mar. 3, 2021 (IN) .............................. 202121008937

(51) Int. Cl.
*A61L 24/08* (2006.01)
*A61L 24/00* (2006.01)
*A61L 24/04* (2006.01)

(52) U.S. Cl.
CPC ........... *A61L 24/08* (2013.01); *A61L 24/0015* (2013.01); *A61L 24/043* (2013.01); *A61L 2300/236* (2013.01); *A61L 2300/41* (2013.01); *A61L 2300/622* (2013.01); *A61L 2400/04* (2013.01)

(58) Field of Classification Search
CPC ................................................ A61L 2300/236
See application file for complete search history.

(56) References Cited

U.S. PATENT DOCUMENTS

| | | | | |
|---|---|---|---|---|
| 8,871,873 B2 * | 10/2014 | Fujita | ................... | A61L 24/046 525/411 |
| 9,220,761 B2 | 12/2015 | Barnett | | |
| 2010/0080788 A1 | 4/2010 | Barnett et al. | | |
| 2013/0211249 A1 | 8/2013 | Barnett et al. | | |
| 2013/0243864 A1 * | 9/2013 | Macdonald | .......... | A61K 9/0019 424/490 |

FOREIGN PATENT DOCUMENTS

WO 2012/071527 A2 5/2012

OTHER PUBLICATIONS

International Search Report and Written Opinion dated Nov. 23, 2020 for International Patent Application No. PCT/IB2020/058022, 11 pages.
Sangeetha Kunjukunju et al. "Cross-linked enzyme aggregates of alginate lyase: A systematic engineered approach to controlled degradation of alginate hydrogel," Internationnal Journal of Biological Macromolecules, Aug. 1, 2018, vol. 115, pp. 176-184.
Vaidya et al., "An Overview of Embolic Agents," Semin. Intervent. Radiol., 2008; 25:204-15.
Tamiya et al., "Freeze Denaturation of Enzymes and its Prevention with Additives," Cryobiology 22, pp. 446-456 (1985).
Yu et al., "Metal-Based X-ray Contrast Media," Chem. Rev. 1999, 99, pp. 2353-2377.
Lee et al., "Alginate: properties and biomedical applications," Prog. Polym. Sci., 2012, 37(1): 106-126.
Brus et al., "Structure and Dynamics of Alginate Gels Cross-Linked by Polyvalent Ions Probed Via Solid State NMR Spectroscopy," Biomacromolecules, 2017, 18:2478-2488.
Ramos et al., "Effect of alginate molecular weight and M/G ration in beads properties foreseeing the protection of probiotics", Food Hydrocoll, 2018; 77;8-16.
Inoue et al., "Functional identification of alginate lyase from the brown alga *Saccharina haponica*", Sci. Rep. 2019;9:1-11.
Farres et al., "Formation kinetics and rheology of alginate fluid gels produced by in-situ calcium release", Food Hydrocolloids 40 (2014): 76-84.
Porter et al., "Effects of freezing on particulate enzymes of rat liver", J. biol. Chen 205 (1953): 883-891.
Chan et al., "Effects of starch filler on the physical properties of lyophilized calcium-alginate beads and the viability of encapsulated cells", Carbohydrate polymers 83, No. 1 (2011); 225-232.
Okuno et al., "Midterm Clinical Outcomes and MR Imaging Changes after Transcatheter Arterial Embolization as a Treatment for Mild to Moderate Radiographic Knee Osteoarthritis Resistant to Conservative Treatment", J. Vasc. Interv. Radiol, 2017;28:995-1002.
International Search Report and Written Opinion dated Jun. 13, 2022 for International Patent Application No. PCT/IB2022/051852, 11 pages.

* cited by examiner

*Primary Examiner* — Gina C Justice
(74) *Attorney, Agent, or Firm* — Morgan Lewis & Bockius

(57) ABSTRACT

The present disclosure provides compositions including alginate microspheres capable of self-degradation upon rehydration, the alginate microspheres comprising alginate, alginate lyase, and divalent metal ions. The present disclosure also provides methods of making compositions including alginate microspheres capable of self-degradation upon rehydration, comprising alginate, alginate lyase, and divalent metal ions. The present disclosure also provides methods of inducing an embolism in a subject in thereof, and syringes containing the compositions of the present disclosure for use in the methods thereof.

21 Claims, 19 Drawing Sheets

ALGINATE BASED PARTICLES AS A TEMPORARY EMBOLIC AGENT

CROSS-REFERENCE TO RELATED APPLICATIONS

The present application is a U.S. national phase of International Patent Application No. PCT/IB2022/051852 filed Mar. 2, 2022, which claims priority to Indian Provisional Patent Application No. 202121008937 filed on Mar. 3, 2021, each of which is hereby incorporated by reference in its entirety for all purposes.

FIELD

The present disclosure provides compositions and methods of making alginate microspheres crosslinked using divalent ions and/or photo-crosslinking. In some aspects, the alginate microspheres are encapsulated with alginate lyase and/or anti-inflammatory agents for embolic applications. In some aspects, post-preparation processing (e.g., sterilization and lyophilization) of the alginate microspheres is used for improving shelf-life.

BACKGROUND

Artificial blocking of a blood vessel, or embolization, in an organ may be used, for example, (a) to control bleeding caused due to trauma, (b) to prevent blood flow into abnormal blood vessels such as aneurysms, and/or (c) to treat an organ (e.g., to excise a tumor, for transplant, or for surgery). In many circumstances, the permanent embolization of blood vessels is not required. For such medical interventions, using temporary and bioresorbable embolic agents is desirable. For example, IMP/CS (Imipenem/Ciliastatin) antibiotic particles of size ranging from 10 μm to 80 μm have been used as a temporary embolic agent, however this material can require nearly a month to become absorbed completely (see, e.g., Okuno, et al.; "Midterm Clinical Outcomes and MR Imaging Changes after Transcatheter Arterial Embolization as a Treatment for Mild to Moderate Radiographic Knee Osteoarthritis Resistant to Conservative Treatment", J. Vasc. Interv. Radiol. 2017; 28:995-1002). Similarly, other embolic agents such as Gelfoam®, collagen, and thrombin have also been used (see, e.g., Vaidya, et al.; "An overview of embolic agents", Semin. Intervent. Radiol. 2008; 25:204-15). However, existing agents have numerous drawbacks such as unpredictable resorption rate, lack of agent(s) that selectively degrade abovementioned matrices, and/or migration of the embolic agents causing non-specific occlusion (see, e.g., U U.S. Patent Application Publication No. 20130211249). Furthermore, some embolic agents require a processing or preparation step before their use within the body. For example, Gelfoam has to be cut up into pledgets or slurried. Likewise, autologous blood clots have to be collected formed and re-injected.

Accordingly, there is a need for embolic agents that can selectively degrade abovementioned matrices, and/or exhibit predictable dissolution rate without creating any non-specific occlusion in vivo.

SUMMARY OF THE DISCLOSURE

In one aspect, the present disclosure relates to an alginate microsphere capable of self-degradation upon rehydration, comprising: an alginate lyase enzyme pre-treated by varying temperature, by varying pH, and/or with a metal-ion enzyme inhibitor; alginate molecules having one or both of (i) a predetermined molecular weight, and (ii) a predetermined ratio of β-D-Mannuronic acid (M) blocks to α-L-Guluronic acid (G) blocks; and a divalent metal-ion crosslinking the alginate molecules, wherein the alginate microsphere is substantially free of water and/or sterilized. In one embodiment, the degradation of alginate microsphere is controlled by one or more of the pre-treatment of the alginate lyase enzyme, an amount of the alginate enzyme in the microsphere, the predetermined molecular weight of the alginate molecule, and the predetermined ratio of M:G blocks of the alginate molecules, and a composition of gelling bath, including an amount and or charge of one or more ions in the gelling bath. In one embodiment, at least one of (i)-(iii) applies: (i) the metal-ion enzyme inhibitor is a reversible inhibitor selected from the group consisting of $Cu^{2+}$, $Zn^{2+}$, and $Fe^{2+}$, (ii) the pre-treatment of the alginate enzyme in the precursor solution allows mixing of a predetermined amount of enzyme (measured in units, U) with the alginate molecules, and (iii) an activity of the alginate lyase enzyme is modulated by adjusting one or more of a pH of a gelling bath, a temperature of the gelling bath, and an amount of the metal-ion enzyme inhibitor in the alginate microsphere. In one embodiment, at least one of (i)-(v) applies: (i) the predetermined molecular weight of the alginate molecules is in a range of greater than about 100 kDa to less than about 800 kDa, (ii) the predetermined ratio of M:G blocks is about 50:50, about 55:45, about 60:40, about 65:35, about 70:30, about 75:25, about 80:20, about 85:15, about 90:10, or about 95:5, (iii) the predetermined ratio of M:G blocks is about 50:50, about 45:55, about 40:60, about 35:65, about 30:70, about 25:75, about 20:80, about 15:85, about 10:90, or about 5:95, (iv) an activity of the alginate lyase enzyme is between about 0.05 mU (milliunits) and about 2.5 mU per microsphere, and (v) an activity of the alginate lyase enzyme is between about 0.05 nU (nanounits) and about 0.05 mU per microsphere. In one embodiment, at least one of (a)-(d) applies: (a) the predetermined ratio of M:G blocks is about 50:50, about 55:45, about 60:40, about 65:35, about 70:30, about 75:25, about 80:20, about 85:15, about 90:10, or about 95:5 and the alginate microsphere degrades over a period of less than about 5 days or greater than about 2 days, (b) the predetermined ratio of M:G blocks is about 50:50, about 45:55, about 40:60, about 35:65, about 30:70, about 25:75, about 20:80, about 15:85, about 10:90, or about 5:95 and the alginate microsphere degrades over a period of between about 5 days and about 30 days, (c) an activity of the alginate lyase enzyme is between about 0.05 mU (milliunits) and about 2.5 mU per microsphere and the alginate microsphere degrades over a period of less than about 5 days, and (d) an activity of the alginate lyase enzyme is between about 0.05 nU (nanounits) and about 0.05 mU per microsphere and the alginate microsphere degrades over a period of between about 5 days and about 30 days. In one embodiment, at least one of (i)-(vii) applies: (i) the microsphere further comprises a bioactive agent, (ii) the microsphere further comprises a cryoprotectant selected from the group consisting of hydroxypropyl-β cyclodextrin, trehalose, polyvinyl pyrrolidone of 40 kDa (PVP 40 kDa), dextran (70 kDa molecular weight), glucose, lactose, maltodextrins, mannitol, glycols, and polyglycols, (iii) the alginate microsphere is lyophilized, (iv) a sphericity of the alginate microsphere is at least about 0.7, at least about 0.75, at least about 0.8, at least about 0.85, at least about 0.9, at least about 0.95, or at least about 0.99, (v) the alginate microsphere is sterilized, or the alginate microsphere is lyophilized and sterilized, (vi) a shelf-life of the alginate microsphere is at least about 3 months, at least about 6 months, at least about 12 months, at least about 18 months, at least about 24 months, at least about 36 months, at least about 48 months, or at least about 60 months when stored at a given temperature, and (vii) a lyophilized alginate microsphere is reconstituted in saline or saline-radiopaque contrast at physiological pH. In one embodiment, at least one of (a)-(d) applies: (a) the microsphere further comprises a bioactive agent wherein the bioactive agent comprises an anti-inflammatory agent, an anesthetic drug, an anti-cancer agent, or an anti-angiogenic agent, (b) the alginate microsphere is lyophilized wherein a residual water content of the lyophilized alginate microsphere is in the range of about 1% to about 3% by mass, (c) the alginate microsphere is sterilized, or the alginate microsphere is lyophilized and sterilized wherein the sterilization comprises high energy radiation sterilization, gamma-ray sterilization, or e-beam sterilization, and (d) a shelf-life of the alginate microsphere is at least about 3 months, at least about 6 months, at least about 12 months, at least about 18 months, at least about 24 months, at least about 36 months, at least about 48 months, or at least about 60 months when stored at a given temperature, wherein the given temperature is between about 2° C. and about 8° C. or about room temperature (RT). In one embodiment, the microsphere further comprises an anti-inflammatory agent bioactive agent wherein the anti-inflammatory bioactive agent comprises hyaluronic acid having a molecular weight of between about 1 million (M) and about 5 M Daltons. In one embodiment, the alginate microsphere is sterilized, or the alginate microsphere is lyophilized and sterilized wherein the sterilization comprises gamma-ray sterilization of between about 15 and about 25 kGy of gamma radiation from Cobalt 60 Isotope, or about 25 kGy of electron beam radiation in accordance with ISO 11137-1:2006.

In another aspect, the present disclosure relates to a method of preparing an alginate microsphere capable of self-degradation upon rehydration, the method comprising: forming droplets from a precursor solution, the precursor solution comprising: (i) an alginate lyase enzyme pre-treated by varying temperature, by varying pH, and/or with a metal-ion enzyme inhibitor; and (ii) alginate molecules having one or both of (a) a predetermined molecular weight, and (b) a predetermined ratio of β-D-Mannuronic acid (M) blocks to α-L-Guluronic acid (G) blocks; contacting the droplets with a gelling bath comprising a divalent metal-ion, thereby crosslinking the alginate molecules to form an alginate microsphere; and dehydrating, and optionally sterilizing, the alginate microsphere thereby substantially removing water from the microsphere. In one embodiment, at least one of (i)-(x) applies: (i) the precursor solution comprises one or more cryoprotectants, (ii) the gelling bath comprises one or more cryoprotectants, (iii) the pH of alginate lyase enzyme in the precursor solution containing alginate lyase and alginate is in the range of pH 3.0 to 6.4, (iv) the metal-ion enzyme inhibitor is a reversible inhibitor selected from the group consisting of $Cu^{2+}$, $Zn^{2+}$, and $Fe^{2+}$, (v) the temperature of the precursor solution is in the range of 1-4° C., (vi) the pre-treatment of the alginate enzyme in the precursor solution allows mixing of a predetermined amount of enzyme (measured in units, U) with the alginate molecules, (vii) an activity of the alginate lyase enzyme is modulated by adjusting one or more of a pH of the gelling bath, a temperature of the gelling bath, and an amount of the metal-ion enzyme inhibitor in the alginate microsphere, (viii) a pH of the gelling bath is less than about 6.5, (ix) a pH of the gelling bath is equal to or about equal to a pH of the precursor solution, and (x) the precursor solution and/or the gelling bath further comprises a bioactive agent. In one embodiment, at least one of (i)-(iv) applies: (i) the dehydrating comprises lyophilizing the alginate microsphere, (ii) forming the droplets is performed using a method selected from the group consisting of drop casting, spray congealing/spray cooling, spray drying, microfluidic droplet production, and jet-cutting, (iii) a sphericity of the alginate microsphere is at least about 0.7, at least about 0.75, at least about 0.8, at least about 0.85, at least about 0.9, at least about 0.95, or at least about 0.99, and (iv) a shelf-life of the alginate microsphere is at least about 3 months, at least about 6 months, at least about 12 months, at least about 18 months, at least about 24 months, at least about 36 months, at least about 48 months, or at least about 60 months when stored at a given temperature. In one embodiment, the precursor solution and/or the gelling bath comprises one or more cryoprotectants, wherein the cryoprotectants are each independently selected from the group consisting of hydroxypropyl-β cyclodextrin, trehalose, polyvinyl pyrrolidone of 40 kDa (PVP 40 kDa), dextran (70 kDa molecular weight), glucose, lactose, maltodextrins, mannitol, glycols, and polyglycols. In one embodiment, the precursor solution comprises trehalose cryoprotectant in a concentration of about 0.1% w/v to about 20% w/v, PVP 40 kDa cryoprotectant in a concentration of about 0.1% w/v to about 1% w/v, or dextran (molecular weight 70 kDa) cryoprotectant in a concentration of about 0.1% w/v to about 1% w/v. In one embodiment, the precursor solution and/or the gelling solution comprise a hydroxypropyl-β cyclodextrin cryoprotectant in a concentration of about 0.1% w/v to about 2% w/v. In one embodiment, the precursor solution and the gelling bath both comprise the same cryoprotectant. In one embodiment, the precursor solution and the gelling bath both comprise the same cryoprotectant at equal or about equal concentrations. In one embodiment, the dehydrating comprises lyophilizing the alginate microsphere wherein a residual water content of the lyophilized alginate microsphere is in the range of about 1% to about 3% by mass. In one embodiment, the method further comprises at least one step selected from (i)-(iv): (i) sterilizing the alginate microsphere or the alginate microsphere that has been dehydrated by lyophilization, (ii) storing the alginate microsphere for at least about 3 months, at least about 6 months, at least about 12 months, at least about 18 months, at least about 24 months, at least about 36 months, at least about 48 months, or at least about 60 months when stored at a given temperature, (iii) administering the alginate microsphere, or the alginate microsphere that has been dehydrated by lyophilization, to a subject, and (iv) reconstituting the alginate microsphere, or the alginate microsphere that has been dehydrated by lyophilization, using saline or saline-radiopaque contrast at physiological pH. In one embodiment, at least one of (a)-(d) applies: (a) the method further comprises the step of sterilizing the alginate microsphere or the alginate microsphere that has been dehydrated by lyophilization, wherein the sterilizing comprises high energy radiation sterilization, gamma-ray sterilization, or e-beam sterilization, (b) the method further comprises the step of sterilizing the alginate microsphere or the alginate microsphere that has been dehydrated by lyophilization, wherein the sterilizing comprises between about 15 and about 25 kGy of gamma radiation from Cobalt 60 Isotope, or about 25 kGy of electron beam radiation in accordance with ISO 11137-1:2006, (c) the method further comprises the step of storing the alginate microsphere for at least about 3 months, at least about 6 months, at least about 12 months, at least about 18 months, at least about 24 months, at least about 36 months, at least about 48 months, or at least about 60 months when stored at a given temperature, wherein the given temperature is between about 2° C. and about 8° C. or the given temperature is about room temperature (RT). In one embodiment, the degradation of alginate microsphere is controlled by one or more of the pre-treatment of the alginate lyase enzyme, an amount of the alginate enzyme in the microsphere, the predetermined molecular weight of the alginate molecule, and the predetermined ratio of M:G blocks of the alginate molecules, and a composition of gelling bath, including an amount and or charge of one or more ions in the gelling bath. In one embodiment, at least one of (i)-(vii) applies: (i) the predetermined molecular weight of the alginate molecules is in a range of greater than about 100 kDa to less than about 800 kDa, (ii) the predetermined ratio of M:G blocks is about 50:50, about about 60:40, about 65:35, about 70:30, about 75:25, about 80:20, about 85:15, about or about 95:5, (iii) the predetermined ratio of M:G blocks is about 50:50, about 45:55, about 40:60, about 35:65, about 30:70, about 25:75, about 20:80, about 15:85, about 10:90, or about 5:95, (iv) the pre-treated alginate lyase enzyme is mixed in the precursor solution having enzyme activity ranging from 0.0025 U/mg to 1 U/mg of alginate, (v) the pre-treated alginate lyase enzyme is mixed in the precursor solution having enzyme activity ranging from 0.125 U/mg to 0.250 U/mg of alginate, (vi) the pre-treated alginate lyase enzyme is mixed in the precursor solution having enzyme activity ranging from 0.025 U/mg to 0.125 U/mg of alginate, and (vii) the pre-treated alginate lyase enzyme is mixed in the precursor solution having enzyme activity ranging from 0.0025 U/mg to 0.005 U/mg of alginate. In one embodiment, at least one of (a)-(e) applies: (a) the predetermined ratio of M:G blocks is about 50:50, about 55:45, about about 65:35, about 70:30, about 75:25, about 80:20, about 85:15, about 90:10, or about and the alginate microsphere degrades over a period of less than about 5 days or greater than about 2 days, (b) the predetermined ratio of M:G blocks is about 50:50, about 45:55, about about 35:65, about 30:70, about 25:75, about 20:80, about 15:85, about 10:90, or about and the alginate microsphere degrades over a period of between about 5 days and about 30 days, (c) the pre-treated alginate lyase enzyme is mixed in the precursor solution having enzyme activity ranging from 0.125 U/mg to 0.250 U/mg of alginate and the alginate microsphere degrades over a period of less than about 5 days, (d) the pre-treated alginate lyase enzyme is mixed in the precursor solution having enzyme activity ranging from 0.025 U/mg to 0.125 U/mg of alginate and the alginate microsphere degrades over a period of between about 5 days and about 30 days, and (e) the pre-treated alginate lyase enzyme is mixed in the precursor solution having enzyme activity ranging from 0.0025 U/mg to 0.005 U/mg of alginate and the alginate microsphere degrades over a period of greater than about 30 days. In one embodiment, the precursor solution and/or the gelling bath further comprises a bioactive agent, wherein the bioactive agent comprises an anti-inflammatory agent, an anesthetic agent, anti-cancer agent, or an anti-angiogenic agent. In one embodiment, the precursor solution and/or the gelling bath comprise an anti-inflammatory bioactive agent, wherein the anti-inflammatory agent comprises hyaluronic acid having a molecular weight of between about 1 million (M) and about 5 M Daltons.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

BRIEF DESCRIPTION OF THE SEVERAL VIEWS OF THE DRAWINGS

The foregoing summary, as well as the following detailed description of embodiments of the compositions and fluid delivery devices, will be better understood when read in conjunction with the appended drawings of exemplary embodiments. It should be understood, however, that embodiments of the present disclosure are not limited to the precise arrangements and instrumentalities shown.

DETAILED DESCRIPTION

Overview

Figures 1A, 1B, 1C:
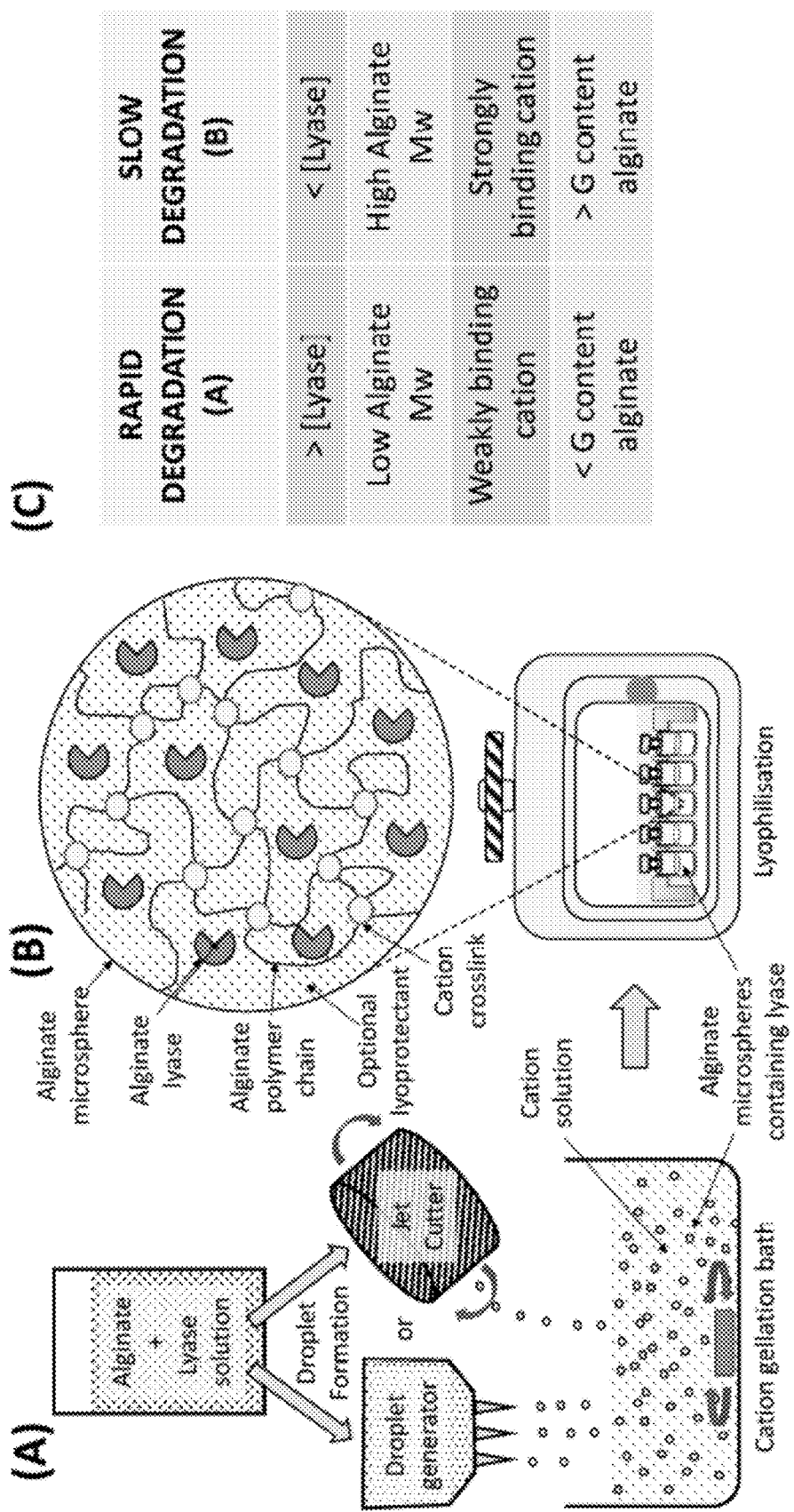
FIG. 1A illustrates the preparation and tailoring of properties of exemplary microspheres of the present disclosure. Alginate and alginate lyase dissolved in aqueous media. Microspheres prepared by conventional methods to gel alginate+lyase droplets by cationic crosslinking.
FIG. 1B illustrates the preparation and tailoring of properties of exemplary microspheres of the present disclosure. Microspheres are lyophilized with optional lyoprotectant to remove water and "freeze" enzyme activity, preventing premature degradation during storage. Microspheres are sterilized in this form.
FIG. 1C illustrates the preparation and tailoring of properties of exemplary microspheres of the present disclosure. Degradation properties may be controlled by varying lyase and alginate parameters and preparation conditions to produce particles of varied degradation rates from days to months depending upon indication to be treated.
Figures 2A, 2B, 2C:
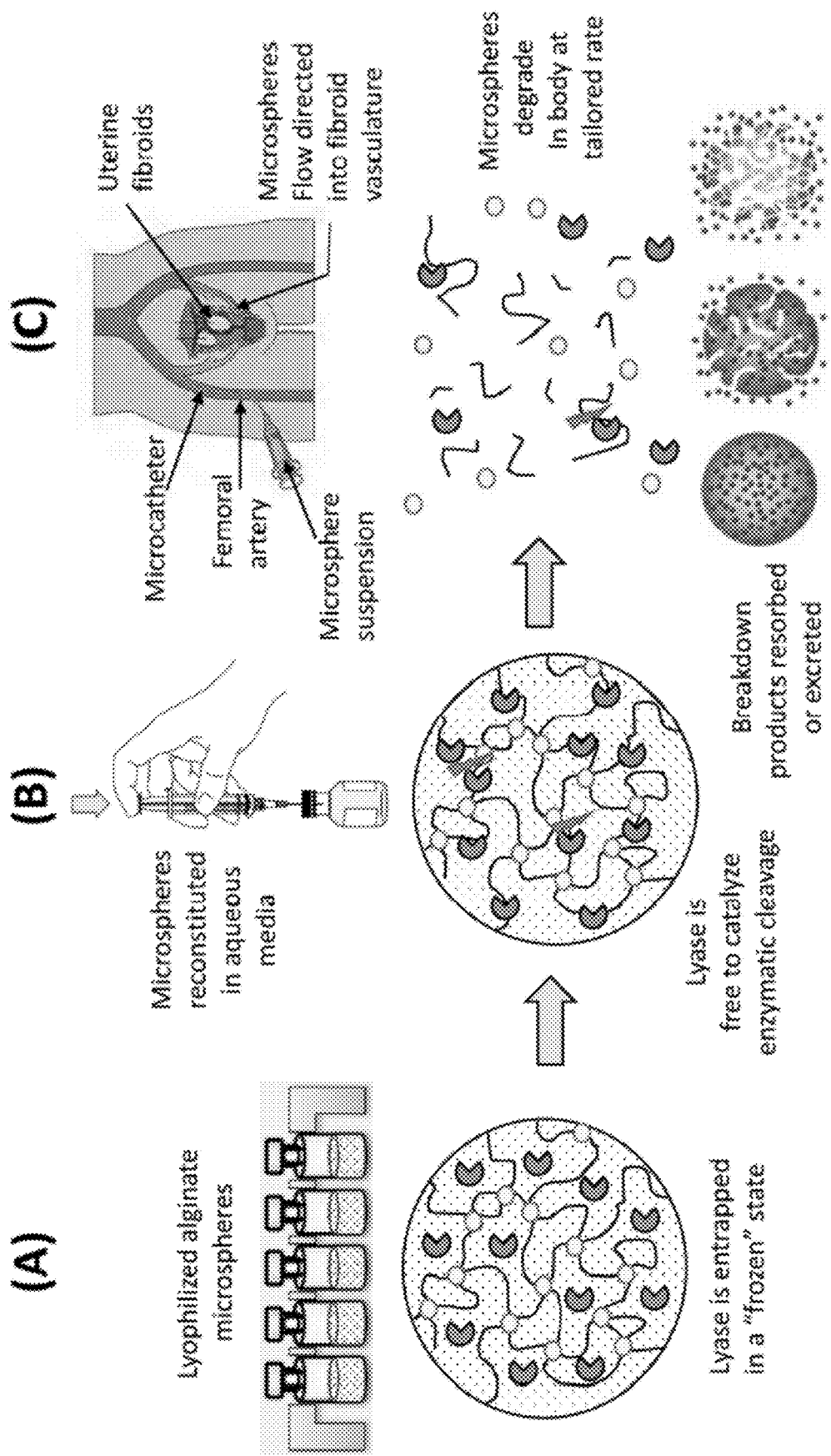
FIG. 2A illustrates exemplary post-particle preparation processes and methods of use. Lyophilized alginate particles are prepared to remove water and freeze enzyme activity. Cryoprotectant protects enzyme and microsphere structure to allow shape recovery upon hydration.
FIG. 2B illustrates exemplary post-particle preparation processes and methods of use. Particles are reconstituted in aqueous media at point of use, hydrating the particle and enabling catalytic activity of the lyase.
FIG. 2C illustrates exemplary post-particle preparation processes and methods of use. Particles are prepared in an appropriate suspension for intra-arterial delivery for the designated embolization procedure (e.g., uterine fibroid embolization). When in the body, the enzyme activity is enhanced and the alginate chains are cleaved, releasing the cations, polymer chain fragments and lyase into the body where they may be resorbed or excreted.

Generally, the present disclosure provides a method for the preparation of dehydrated and/or sterilized compositions comprising alginate particles containing alginate lyase enzyme to control its degradation for use in embolization applications.

Alginate based liquid embolic agents have been considered as a promising alternative. Pure forms of alginate are highly biocompatible, and their gelling properties can be controlled. They are naturally-occurring polysaccharide copolymers composed of randomly 1-4 linked β-D-mannuronic acid (M-block)-α-L-guluronic (G block) of various M:G ratios that are commonly found in various seaweeds. In the prior-art disclosure, alginate is dissolved in the contrast agent iohexol (to impart radiopacity) and is gelled into hydrocoil form which solidifies in the presence of calcium chloride solution due to ionic crosslinking of the carboxylate groups of the polysaccharide residues with $Ca^{2+}$. All of these components were mixed simultaneously at the treatment site to create an in situ mass of gel. This gel may be subsequently dissolved using a mixture termed EmboClear by the inventors, which is a mixture of alginate lyase enzyme and EDTA (Ethylenediaminetetraacetic acid). The enzyme cleaves the polysaccharide chains at the glycosidic bond via a β-elimination mechanism and the EDTA de-complexes the ionic crosslinks by scavenging the $Ca^{2+}$ by chelation. This dissolution agent was administered at the site of the embolus and it completely cleared the occluded vessel within a few minutes. This invention addresses some aspects of the selective degradation of the embolic agent but poses a few complications.

Firstly, the procedure to degrade the EmboGel using Emboclear solution introduces additional risk to the patient, as they must undertake additional post embolization procedures. Moreover, depending upon the time interval desired between formation of the embolus and its dissolution, this could involve rescheduling the patient for a second visit and all the associated costs for a re-catheterization procedure. Secondly, in some cases such as aneurysm therapy, the alginate gel could migrate to the parent artery during injection or after the post-embolization procedure which may cause non-specific vessel occlusion (see, e.g., Barnett, et al., "A selectively dissolvable radiopaque hydrogel for embolic applications"; and U.S. Pat. No. 9,220,761).

Barnett et al. demonstrate that an alginate-based embolic material can be degraded within the body by application of an alginate lyase based composition. Purified alginate is dissolved in the contrast agent iohexol (to impart radiopacity) and is gelled into hydrocoil form which solidifies in the presence of calcium chloride solution due to ionic crosslinking of the carboxylate groups of the polysaccharide residues with $Ca^{2+}$. All of these components were mixed simultaneously at the treatment site to create an in situ mass of gel. This gel may be subsequently dissolved using EmboClear.

In U.S. Pat. No. 9,220,761, non-specific migration of degraded/disintegrated alginate gels to other parts of the body predominantly occurs due to instant/uncontrolled degradation/disintegration of EmboGel by the EmboClear, causing generation of particulates of various size and that are unable to be reabsorbed before they are distributed to off-target distal locations at which the Emboclear is ineffective due to dilution. If EmboGel is loaded with a bioactive agent/drug, it requires the separate administration of EmboClear dissolution agent in order to afford degradation-controlled release kinetics.

Boyan et al. report a method and composition of alginate particles consisting of alginate lyase and stem cells (see, i.e., PCT Publication No. WO 2012/071527 A2). Depending on the concentration of enzyme incorporated, proteins secreted by stem cells or stem cells can be delivered into the body. In contrast with various embodiments of the present disclosure, the compositions of Boyan are incapable of being lyophilized and sterilized without killing the stem cells therein. In Boyan, $Ca^{2+}$ crosslinked alginate particles are used to encapsulate alginate lyase and stem cells for the sustained release of proteins and stem cells. In this method, the varying amount of alginate lyase along with stem cells are mixed with alginate of different molecular weight for 1 minute at 1-4° C. and gelled in a calcium chloride bath to obtain self-degradable stem cell-encapsulated calcium crosslinked alginate microspheres. In order to release the stem cells and their secreted proteins, these particles were suspended in saline @37° C. to activate the alginate matrix-degrading catalytic activity of the alginate lyase enzyme. Furthermore, the alginate particles loaded with cells were processed with DMSO for cryopreservation in liquid nitrogen. This report provided insight into controlled degradation of alginate particles, but there are many drawbacks for using this method to produce scalable self-degradable alginate particles for embolic applications. It was observed that the reduction of temperature to 1-4° C. does not completely cease the degrading activity of the enzyme. Furthermore, the incubation period of the enzyme with alginate will be higher, if the production of these particles needs to scale up. This reduces the viscosity of the alginate, thereby reducing the encapsulation of the alginate lyase enzyme and also poses a challenge in obtaining uniformly shaped particles. Likewise, any proposed encapsulation of bioactive agents (such as anti-inflammatory and anticancer) would also be reduced. Furthermore, the method to encapsulate bioactive agents and post-particle preparation processes such as lyophilization and sterilization of degradable alginate particles were not considered. For developing temporary embolic particles like alginate lyase encapsulate alginate microspheres, it is important to enable storage for a longer time period in dried and sterile form, that can be reconstituted at the point of use, and become activated upon introduction into the body. Therefore, there is a need for temporary embolic agents that can degrade or exhibit predictable resorption rates without creating any non-specific occlusion in vivo, acts as a vehicle for releasing bioactive agent and remain stable for a long time period under desired storage conditions.

Furthermore, Kunjukunju, et al. reported alginate lyase aggregates of various size (10-300 µm) and shape using ammonium sulfate (see, e.g., Kunjukunju, et al., "Crosslinked enzyme aggregates of alginate lyase: A systematic engineered approach to controlled degradation of alginate hydrogel." International Journal of Biological Macromolecules 115 (2018): 176-184). These aggregates were crosslinked using glutaraldehyde to produce insoluble catalytically active alginate lyase aggregates. The resultant crosslinked aggregate was encapsulated in an alginate hydrogel to achieve its controlled degradation. However, the method described in this report may not be suitable to enable the preparation of a temporary alginate-based embolization agent per se.

Firstly, it would not be possible to produce alginate particles of the desired size, as the size and polydispersity of the described aggregates of the enzyme could not be encapsulated. Secondly, the process described crosslinking the enzyme aggregates with glutaraldehyde which is a toxic agent that should be avoided in the preparation of compositions intended for use in the human body. Thirdly, the authors did not report any other methods to control the degradation of the alginate, such as molecular weight or viscosity of sodium alginate, pre-treatment of the enzyme using modifiers (metal ions) or other physiochemical parameters such as pH and temperature or to improve the encapsulation efficiency of alginate lyase enzyme. Lastly, no work has been performed to achieve the storage and shelf life of the alginate aggregates.

The present disclosure provides compositions and methods for making self-degradable crosslinked alginate microspheres loaded with alginate lyase enzyme, bioactive agents and cryoprotectants for embolic applications. This allows the loading or encapsulation of the desired concentration of enzyme and bioactive agents to obtain the tailored degradation of alginate microspheres under physiological conditions. There are many advantages of the present disclosure over the existing temporary embolic agents and prior-art alginate-based systems:

1. By pre-treating the alginate lyase enzyme under a combination of different conditions (pH, temperature and metal ion inhibitor) that may reversibly inhibit the catalytic degrading activity, thereby allowing the controlled loading of the enzyme into alginate particles. This strategy provides the predictable and desired degradation rate of alginate particles which are of prime importance for embolic applications. Using a combination of different conditions to regulate the loading of alginate lyase enzyme into alginate particles has not been described for existing temporary embolic particles and prior-alginate-based systems;
2. The pre-treatment of the enzyme reversibly inhibits the enzyme activity, thereby ceasing the exposure of alginate to the active form of alginate lyase for the desired length of time. This strategy may allow the scale-up production of these microspheres without prematurely degrading the alginate matrix;
3. The self-degrading nature of alginate-based enzyme-containing embolic microspheres ensures any by-products or particulates can be reabsorbed and ultimately excreted through the kidneys. Therefore, the risk of non-specific occlusion of blood vessels is minimized;
4. In many embolization procedures, the patients suffer neuropathic pain. These self-degradable alginate microspheres can also be loaded with anti-inflammatory agents, for e.g hyaluronic acid, and its sustained release at the site of embolization may alleviate the neuropathic pain that could arise from chronic inflammation; and/or
5. The composition of self-degradable alginate microspheres also consists of cryoprotectants. The inclusion of cryoprotectant allows the lyophilization and subsequent sterilization without affecting the enzyme activity. These post-preparation processing steps of microspheres result in a sterile composition that can be stored for a length of time and reconstituted at the point of use to re-activate the enzyme before administration into the body.

In addition to divalent-metal ion crosslinking, photopolymerization methods may be used to prepare self-degradable alginate particle compositions with the same properties as discussed above. This method may further improve the calibrated degradation of the alginate microspheres.

Definitions

As used herein, the term "a", "an", or "the" generally is construed to cover both the singular and the plural forms.

As used herein, the term "about" generally refers to a particular numeric value that is within an acceptable error range as determined by one of ordinary skill in the art, which will depend in part on how the numeric value is measured or determined, i.e., the limitations of the measurement system. For example, "about" may refer to a range of ±20%, ±10%, or ±5% of a given numeric value.

The term "substantially" as used herein may refer to a majority of, or mostly, as in at least about 50%, 60%, 70%, 80%, 90%, 95%, 96%, 97%, 98%, 99%, 99.5%, 99.9%, 99.99%, or at least about 99.999% or more.

"Carrier" or "vehicle" as used herein refer to carrier materials suitable for drug administration. Carriers and vehicles useful herein include any such materials known in the art, e.g., any liquid, gel, solvent, liquid diluent, solubilizer, surfactant, or the like, which is nontoxic and which does not interact with other components of the composition in a deleterious manner.

The term "therapeutically effective amount" may generally refer to the amount (or dose) of a compound or other therapy that is minimally sufficient to prevent, reduce, treat or eliminate a condition, or risk thereof, when administered to a subject in need of such compound or other therapy. In some instances, the term "therapeutically effective amount" may refer to that amount of compound or other therapy that is sufficient to have a prophylactic effect when administered to a subject. The therapeutically effective amount may vary; for example, it may vary depending upon the subject's condition, the weight and age of the subject, the severity of the disease condition, the manner of administration (e.g., subcutaneous delivery) and the like, all of which may be determined by one of ordinary skill in the art.

As used herein, "treating" or "treat" includes: (i) preventing a pathologic condition from occurring (e.g., prophylaxis); (ii) inhibiting the pathologic condition or arresting its development; (iii) relieving the pathologic condition; and/or (iv) diminishing symptoms associated with the pathologic condition.

The phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated. Supplementary active ingredients may also be incorporated into the compositions.

The term "pharmaceutically acceptable excipient" is intended to include vehicles and carriers capable of being co-administered with a compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present disclosure.

Compositions & Methods

The present inventions relate to the loading of alginate lyase into sodium alginate or methacrylate-alginate that can be gelled or crosslinked using divalent metal ions or light activated photopolymerization (photo crosslinking) respectively to form enzyme-loaded alginate microspheres. In order to make divalent metal ion crosslinked alginate microspheres loaded with alginate lyase enzyme, the latter is mixed with the alginate (precursor solution) and dripped into a divalent metal ion gelling bath. In the case of photo-crosslinked alginate microspheres loaded with the alginate lyase enzyme, the methacrylate-alginate is mixed with alginate lyase enzyme and photo initiators (precursor solution), which can be either drop casted or injected into different liquid containing surfactant or oils (mono- or double emulsion) using a microfluidics platform for instance, to form droplets. These droplets are irradiated with near UV-wavelength (200 nm-400 nm) for various times. Upon irradiation, the crosslinking of methacrylate-alginate occurs to form of alginate-lyase loaded alginate microspheres. Furthermore, these microspheres can also be encapsulated with anti-inflammatory agents by mixing into precursor solution and subject to the above-mentioned crosslinking procedures. The degradation of these crosslinked alginate particles can be controlled by the composition of precursor solution, gelling bath and method of preparing these particles.

Composition of Precursor Solution for the Preparation of Divalent Metal Ion Crosslinked-Alginate Microspheres Loaded with Alginate Lyase.

The degradation of crosslinked alginate particles can be controlled by the composition of precursor solution (i) concentration of alginate lyase enzyme (may be pre-treated with pH, temperature and metal ion inhibitors) loaded into alginate microspheres and (ii) predetermined molecular weight of alginate and ratio of M (β-D-mannuronic acid) and G (α-L-guluronic acid) blocks (M/G).

In the precursor solution, the alginate lyase enzyme causes breakdown of the alginate which can impact the encapsulation of alginate lyase enzyme into alginate particles. This also reduces the initial viscosity of alginate solution, which is important for maintaining both encapsulation efficiency within the alginate particles and also for obtaining particles of desired size and shape. The enzyme may therefore be pre-treated at different pH, low temperature and/or exposure to metal ion inhibitors, before adding the precursor mix to the divalent metal ion gelling bath for crosslinking.

The optimum catalytic activity of the lyase enzyme is observed at pH ranging from 6.8 to 7.5. To prevent the initial degradation of sodium alginate during the preparation of alginate lyase loaded alginate particles, the pH of the alginate lyase-sodium alginate solution may be reduced to 3.0. To carry out this process, sodium acetate-acetic acid buffer, of ionic strength <1 M, preferably <0.1 M and most preferably <0.01M with a pH range 3.7-5.6. In addition, the desired pH (pH 6.5 to 3.0) of the solution may also be achieved using sodium hydroxide (>1M to <0.01M) or hydrochloric acid (>1M to <0.01M). This results in the reduction or ceasing of the alginate lyase catalytic activity. This regulation of the catalytic activity may be attributed to the unfolding of 3D conformation of alginate lyase enzyme. The ceased catalytic activity of the alginate lyase enzyme may be reversed/activated by exposing alginate lyase loaded alginate particles to the aqueous environment having pH 6.5 to 7.5 The preferred buffers for reversing the activity of the alginate lyase enzyme are phosphate buffers. The preferred ionic strength of the phosphate buffer is 0.01 M with a pH range of 6.5 to 7.5 at 20° C. The desired pH (pH 6.5 to 7.5) of the solution may also be achieved using sodium hydroxide (>1M to <0.01M) or hydrochloric acid (>1M to <0.01M). Additionally, saline or de-ionized water or an aqueous solution having a pH between 6.5-7.5 may also be used.

In combination with changing the pH of the solution, the temperature of the individual component of the precursor solution before mixing may be maintained at 1-4° C. to inhibit the degradation of alginate. The temperature of precursor solution after mixing the individual component may be maintained at 1-4° C. to inhibit the degradation of alginate. Note that the temperature will also influence the viscosity of the solution.

In addition to changing the pH and temperature of the precursor solution, the enzyme may be pre-treated with the metal ion inhibitors such as $Cu^{2+}$, $Zn^{2+}$ and $Fe^{2+}$. These metal ions can inhibit the activity of the enzyme (Inoue, et al., "Functional identification of alginate lyase from the brown alga *Saccharina japonica*", Sci. Rep. 2019; 9:1-11).

Therefore, a combination of the abovementioned approaches may be used to inhibit (reversibly or partially) the alginate lyase enzyme in the precursor solution. This may enhance the loading of alginate lyase enzyme into the alginate particles without degrading the alginate matrix. The combination of these approaches has not been adopted in the cited reports.

The self-degradation of alginate microspheres can also be controlled by chemical properties of the alginate (molecular weight and the ratio of M (β-D-mannuronic acid) and G (α-L-guluronic acid) blocks (M/G)). Particularly, the G-block has more affinity toward divalent cations as compared to the M-block due to the geometry of the carboxylate residues. Alginate contains a large variation in the M and G content, and also possesses the variation in the sequence structures (G-block, M-block and MG block) Ramos, et al., "Effect of alginate molecular weight and M/G ratio in beads properties foreseeing the protection of probiotics", Food Hydrocoll. 2018; 77:8-16). In general, the alginate with a higher G content relative to M content (lower M/G ratio) when crosslinked with cations gives more mechanically robust structures/capsules with low permeability and greater resistance to enzyme degradation, when compared to the alginate with higher M/G ratio. Other factors which improve the robustness of alginate are choice of divalent ions and molecular weight/viscosity of alginates.

To achieve the rapid degradation (>=2 days to <=5 days) of alginate lyase-loaded divalent metal ion complexed alginate particles, lower G-content alginate (e.g., higher M:G ratio) having low molecular weight/low viscosity may be used in the precursor solution. In certain embodiments, the purified alginate contains more than 50% M content (β-D-mannuronic acid). The percentage of M-content in the purified alginate maybe 50% and 80%, 55%-75% and 60%-80%. To get intermediate (>5 days to <=30 days) or slow (>30 days) degradation periods the higher G content alginate (e.g., the lower M:G ratio) having high molecular weight/ viscosity may be used. In certain embodiments, the purified alginate contains more than 50% G content (α-L-guluronic acid). The percentage of G-content in the purified alginate maybe 50% and 80%, 55%-75% and 60%-80%.

The molecular weight or viscosity of alginate also affect the mechanical properties of the alginate particle (Farrés, et al., "Formation kinetics and rheology of alginate fluid gels produced by in-situ calcium release", Food Hydrocolloids 40 (2014): 76-84). The average molecular weight of alginate polymers may be >100 kDa, preferably >200 kDa and most preferably >30 kDa. The viscosity of 1% alginate solution at 20° C. may have a range >25 mPa·s, preferably <1000 mPa·s for the preparation of rapid and slow degrading alginate lyase loaded divalent metal ion complexed alginate particles.

The activity (Units, U) of treated (pH, temperature and metal ion inhibitor exposed) alginate lyase enzyme mixed with alginate of different molecular weight and M/G ratio (M ((3-D-mannuronic acid) and G (α-L-guluronic acid) blocks (M/G) ratio) in the precursor solution also regulates the degradation of divalent metal ion-crosslinked alginate microspheres. The activity of the alginate lyase enzyme may range from 0.025 U/mg to 1 U/mg of alginate. For the rapid degradation of alginate microspheres (>=2 days to <=5 days), the preferred activity of the enzyme may range from 0.125 U/mg to 0.25 U/mg of alginate. To get intermediate (>5 days to <=30 days) or slow (>30 days) degradation periods, the preferred range of enzyme activity may be 0.025 U/mg to 0.125 U/mg of alginate and 0.0025 U/mg to 0.005 U/mg of alginate respectively.

Encapsulation of Bioactive Agents

Previous reports demonstrated that high molecular weight hyaluronic acid (100-500 KDa) displays anti-inflammatory and immunosuppressive activity. Many embolization medical interventions cause neuropathic pain which may be relieved by the use of hyaluronic acid of high molecular weight. The present invention discloses the encapsulation of high molecular weight hyaluronic acid in the alginate lyase loaded-divalent metal ion crosslinked alginate microspheres. To the precursor solution mentioned previously mentioned, anti-inflammatory bioactive agents including high molecular weight hyaluronic acid may be added. This involves the addition of hyaluronic acid 1% wt to 20% wt of alginate concentration in the precursor solution. On cross-linking in the divalent metal ion-gelling bath, the hyaluronic acid may be encapsulated. The encapsulated hyaluronic acid may be released at the site of embolization due to the degradation of alginate lyase-alginate microspheres. The release of hyaluronic acid may alleviate the neuropathy pain.

Composition of Gelling Bath

The precursor alginate lyase enzyme-sodium alginate (appropriate molecular weight and M/G ratio) solution under the appropriate conditions (low temperature, pH or metal ion) along with hyaluronic acid (as mentioned in section 4.2 and 4.3) needs to be gelling in a divalent metal ion bath to form microspheres. The particle size obtained may be >40 μm, <200 μm but <2000 μm. To reduce the degradation of divalent crosslinked alginate microspheres, the temperature and pH of the gelling bath may be maintained at 1-4° C. and 3.0 respectively. The pH may be maintained using the buffers with ionic strength mentioned in above said section. The composition and condition of the gelling bath are important to make desired alginate-based embolic particles. The divalent metal ion component of the gelling bath composition may be selected from the group consisting $Cu^{2+}$, $Ba^{2+}$, $Sr^{2+}$, $Ca^{2+}$, $Co^{2+}$, $Ni^{2+}$, $Mn^{2+}$ and $Mg^{2+}$ (Lee, et al., "Alginate: properties and biomedical applications,"

Progress in polymer science 37, no. 1 (2012): 106-126; and Brus, et al., "Structure and dynamics of alginate gels crosslinked by polyvalent ions probed via solid state NMR spectroscopy," Biomacromolecules 18, no. 8 (2017): 2478-2488). Divalent cation choice may also influence alginate matrix crosslinking. The binding strength of divalent metal ion with alginate is given in decreasing order $Cu^{2+}>Ba^{2+}>Sr^{2+}>Ca^{2+}>Co^{2+}>Ni^{2+}>Mn^{2+}$, The preferred metal cations are $Ba^{2+}$ and $Ca^{2+}$. These metal ions may be used at different concentrations ranging from 0.1% w/v to 10% w/v. The preferred concentration of divalent metal ion may be 2% w/v.

Lyophilization and Sterilization

The shelf-life of the self-degradable alginate microspheres containing alginate lyase and hyaluronic acid may be improved through the lyophilization and sterilization of lyophilized product. For these post-preparation process, cryoprotectants may be added into precursor solution (obtained in the previous sections) and gelling bath. The addition of cryoprotectants is important in many ways. Firstly, it helps in maintaining the sphericity and mechanical robustness of the alginate lyase loaded alginate particles during lyophilization process. Secondly, it preserves the 3D conformation of the enzyme at extremely low temperatures and freezing cycles, thereby preserving the enzyme activity. Recovery of microsphere shape post lyophilization was considered as an issue. This is not unexpected, as high-water content gels shrink during lyophilization and often do not re-establish their original shape upon rehydration. The addition of cryoprotectants such as sugars and polymers can compensate for this, to help maintain the porous structure during sublimation of the internal water within the structure. Also, it has been observed that the residual activity of the enzyme reduced significantly when the lyophilization of the enzymes was performed without the addition of the cryoprotectants/cryopreservation medium [12, 13]. Thus, the use of cryoprotectants also assists the rapid recovery of shape upon reconstitution in aqueous medium and enables retention of the functionality of the active ingredients including enzymes.

Composition of precursor and gelling solution containing cryoprotectants. Untreated or pre-treated precursor alginate lyase enzyme-sodium alginate and gelling solutions may be mixed with cryoprotectants at different proportions such as hydroxypropyl-beta cyclodextrin, trehalose, polyvinyl pyrrolidone of 40 kDa (PVP 40 kDa) and dextran (70 kDa molecular weight).

Table 1 describes the composition of cryoprotectants in precursor and gelling bath solutions. The preferred concentration of cryoprotectants for precursor solution and gelling bath is described as % w/v of alginate concentration may be from 0.1% w/v to 4% w/v and 0.1% w/v to 10% w/v for divalent metal ion concentration, respectively. The concentration of trehalose, Hydroxypropyl-β-cyclodextrin, PVP (molecular weight 40 kDa) and dextran (molecular weight 70 kDa) may have range from 0.1% w/v to 20% w/v, 0.1% w/v to 2% w/v, 0.1% w/v to 1% w/v and 0.1% w/v to 1% w/v respectively. Other cryoprotectants such as glucose, lactose, maltodextrins, mannitol, glycols, and polyglycols can also as Stabilizer 1 in similar proportions to that discussed above. In one embodiment, the glucose, lactose, maltodextrins, mannitol, glycol, or polyglycol Stabilizer 1 is used along with Stabilizer 2.

TABLE 1

Composition of cryoprotectants in precursor and gelling bath solutions

| Formulation | Stabilizer 1 | Stabilizer 2 |
|---|---|---|
| 1 | Hydroxypropyl-β-cyclodextrin (0.5%, W/V) | |
| 2 | Hydroxypropyl-β-cyclodextrin (1.3%, W/V) | |
| 3 | Hydroxypropyl-β-cyclodextrin (0.5%, W/V) | trehalose (0.5%, W/V) |
| 4 | Hydroxypropyl-β-cyclodextrin (1.3%, W/V) | trehalose (5%, W/V) |
| 5 | Hydroxypropyl-β-cyclodextrin (1.3%, W/V) | trehalose (20%, W/V) |
| 6 | PVP 40 kDa (0.5%, W/V) | trehalose (0.5%, W/V) |
| 7 | dextran 70 kDa (0.4%, W/V) | trehalose (0.5%, W/V) |

These cryoprotectants components may be mixed with the untreated and pre-treated precursor solutions for 15 min to 1 hours before adding into gelling bath containing cryoprotectants for crosslinking with divalent metal ion to form alginate microspheres containing alginate lyase and cryoprotectants. These microspheres may be subjected to a lyophilization cycle to obtain freeze-dried particles with the moisture content 3% by mass or less, preferably 2% by mass or less and more preferably 1% by mass or less. Under dry conditions sealed in a vial, the dried particles may be further subjected to the high-energy radiation sterilization (gamma or e-beam radiation). These lyophilized and sterilized alginate lyase loaded divalent metal ion-crosslinked alginate microspheres can be stored for ≤24 months.

Compositions and Methods of Preparing Photo-Crosslinked Self-Degradable Alginate Microspheres Loaded with Alginate Lyase The self-degradable photo-crosslinked alginate particles loaded with alginate lyase can be prepared using methacrylate-alginate and photoinitiators. The degradation of the photocrosslinked particles can be modulated by controlling the composition of precursor solution which comprises of (i) alginate lyase enzyme (may be pre-treated with pH, temperature and metal ion inhibitors) loaded into photo-crosslinked alginate microspheres, (ii) methacrylate substituted/functionalized alginate of predetermined molecular weight and ratio of M (β-D-mannuronic acid) and G (α-L-guluronic acid) blocks (M/G)), (iv) the ratio of photo-initiator to methacrylate alginate concentration and (v) duration of photo irradiation affecting the crosslinking of the particles.

Similar to divalent metal ion crosslinked alginate microspheres, the precursor solution containing alginate lyase may degrade the alginate. This may reduce the viscosity of alginate reduce the enzyme loading capacity of alginate and adversely affect the particles size and shape. Therefore, the precursor solution may or may not be pre-treated at different pH, low temperature and exposure to metal ion inhibitor, before subjecting to the photo-irradiation.

All the pre-treatment processes of the precursor solution are exactly same as mentioned for the preparation of divalent metal ion-crosslinked microspheres.

Herein, the molecular weight and the ratio of M:G block of methacrylate-alginate is considered.

The degradation of crosslinked alginate particles can be controlled by the composition of precursor solution (i) concentration of alginate lyase enzyme (may be pre-treated with pH, temperature and metal ion inhibitors) loaded into alginate microspheres and (ii) predetermined molecular weight of alginate and ratio of M (β-D-mannuronic acid) and G (α-L-guluronic acid) blocks (M/G).

In the precursor solution, the alginate lyase enzyme causes breakdown of the alginate which can impact the encapsulation of alginate lyase enzyme into alginate particles. This also reduces the initial viscosity of alginate solution, which is important for maintaining both encapsulation efficiency within the alginate particles and also for obtaining particles of desired size and shape. The enzyme may therefore be pre-treated at different pH, low temperature and/or exposure to metal ion inhibitors, before adding the precursor mix to the divalent metal ion gelling bath for crosslinking.

The optimum catalytic activity of the lyase enzyme is observed at pH ranging from 6.8 to 7.5. To prevent the initial degradation of sodium alginate during the preparation of alginate lyase loaded alginate particles, the pH of the alginate lyase-sodium alginate solution may be reduced to 3.0. To carry out this process, sodium acetate-acetic acid buffer, of ionic strength <1 M, preferably <0.1 M and most preferably <0.01M with a pH range 3.7-5.6. In addition, the desired pH (pH 6.5 to 3.0) of the solution may also be achieved using sodium hydroxide (>1M to <0.01M) or hydrochloric acid (>1M to <0.01M). This results in the reduction or ceasing of the alginate lyase catalytic activity. This regulation of the catalytic activity may be attributed to the unfolding of 3D conformation of alginate lyase enzyme. The ceased catalytic activity of the alginate lyase enzyme may be reversed/activated by exposing alginate lyase loaded alginate particles to the aqueous environment having pH 6.5 to 7.5 The preferred buffers for reversing the activity of the alginate lyase enzyme are phosphate buffers. The preferred ionic strength of the phosphate buffer is 0.01 M with a pH range of 6.5 to 7.5 at 20° C. The desired pH (pH 6.5 to 7.5) of the solution may also be achieved using sodium hydroxide (>1M to <0.01M) or hydrochloric acid (>1M to <0.01M). Additionally, saline or de-ionized water or an aqueous solution having a pH between 6.5-7.5 may also be used.

In combination with changing the pH of the solution, the temperature of the individual component of the precursor solution before mixing may be maintained at 1-4° C. to inhibit the degradation of alginate. The temperature of precursor solution after mixing the individual component may be maintained at 1-4° C. to inhibit the degradation of alginate. Note that the temperature will also influence the viscosity of the solution.

In addition to changing the pH and temperature of the precursor solution, the enzyme may be pre-treated with the metal ion inhibitors such as $Cu^{2+}$, $Zn^{2+}$ and $Fe^{2+}$. These metal ions can inhibit the activity of the enzyme (Inoue, et al., "Functional identification of alginate lyase from the brown alga *Saccharina japonica*", Sci. Rep. 2019; 9:1-11).

Encapsulation of Bioactive Agents

Previous reports demonstrated that high molecular weight hyaluronic acid (100-500 kDa) displays anti-inflammatory and immunosuppressive activity. Many embolization medical interventions cause neuropathic pain which may be relieved by the use of hyaluronic acid of high molecular weight. The present invention discloses the encapsulation of high molecular weight hyaluronic acid in the methacrylate-alginate lyase loaded-divalent metal ion crosslinked methacrylate-alginate microspheres. To the precursor solution, anti-inflammatory bioactive agents including high molecular weight hyaluronic acid may be added. This involves the addition of hyaluronic acid 1% wt to 20% wt of methacrylate-alginate concentration in the precursor solution. On crosslinking in the divalent metal ion-gelling bath, the hyaluronic acid may be encapsulated. The encapsulated hyaluronic acid may be released at the site of embolization due to the degradation of methacrylate-alginate lyase-methacrylate-alginate microspheres. The release of hyaluronic acid may alleviate the neuropathic pain.

To make the self-degradable photo crosslinked-alginate microspheres, water-soluble photo initiators such as Irgacure 2959, Irgacure 184, Irgacure 651, Irgacure 369 and Irgacure 907 may be used. The preferred photo initiator is Irgacure 2959. These photo-initiator activate and forms radicals upon the irradiation with ultraviolet light of 320-410 nm wavelength, but the ideal wavelength is 365 nm. The degradation of the microspheres also depends on the concentration of methacrylate-alginate, photoinitiator and duration of UV-irradiation. The concentration of the methacrylate alginate and photo-initiator in the precursor solution may have a range of % w/v to 4% w/v and 0.1% w/v to 1.5% w/v respectively. For the fast-degrading alginate microspheres (≤5 days), the preferable concentrations of alginate and photo-initiator may be 1% w/v-1.5% w/v and 0.1% w/v to 0.3% w/v respectively. For the intermediary degradation period (>5 days to <30 days), the preferable concentrations of alginate and photo-initiator may be 2% w/v-3% w/v and 0.4% w/v to 0.8% w/v respectively. The slow degradation of alginate particles may be achieved using the preferable concentrations of alginate and photo-initiator 3% w/v-4% w/v and w/v to 1.5% w/v respectively Furthermore, the duration of UV irradiation may have a range from >10 seconds to <10 minutes, the preferable duration for the fast degrading microspheres may be <1 minutes, the irradiation duration for intermediary degrading period may be 1-5 minutes, whereas for slow degrading alginate microspheres, the irradiation period may be >5 mins but <10 mins.

Methods to prepare the microspheres may include a drop-casting technique wherein droplets of precursor solution may be printed on a super-hydrophobic surface (e.g., PTFE), or generated using single or double emulsion-microfluidics platforms for instance. Upon generation of droplets of the desired size, UV-light may be exposed to crosslink the chains of alginate to form spherical alginate lyase loaded alginate microspheres.

Method of Making Alginate Particles and Alginate Lyase Encapsulated Alginate Particles Using Microfluidics Alginate particles are produced through droplet-microfluidics which provides precise control on the shape, size, and morphology of alginate droplets. Typically, alginate solution is mixed with water-soluble Ca-EDTA or water-insoluble $CaCO_3$ particles and emulsified in the oil phase on a microfluidics platform to generate the droplets of alginate solution of desired size and shape. The droplets of alginate can be crosslinked to a bivalent $Ca^{2+}$ ion released from Ca-EDTA or $CaCO_3$ under acidic conditions. This crosslinking can be done through "On-Chip" or "Off-chip methods" to generate $Ca^{2+}$-crosslinked alginate beads. However, this conventional method is difficult to use when the macromolecules like alginate lyase can be encapsulated in alginate particles effectively in an acidic pH environment. Therefore, if the above conventional method is used to encapsulate the alginate lyase enzyme in alginate beads, the alginate lyase-alginate mixture containing Ca-EDTA or $CaCO_3$ under acidic conditions would become gelled and the solution could not be passed through the microfluidics platform to generate alginate precursor solution droplets. To overcome this drawback, a new method is presented below to successfully generate the alginate lyase encapsulated alginate beads using microfluidics.

The encapsulation of alginate lyase into alginate beads is performed using a droplet microfluidics method of the present disclosure wherein a precursor solution is prepared in a buffer of pH 10 at temperature 1-4° C., the precursor solution comprising alginate, alginate lyase, and Ca-EDTA or $CaCO_3$. In one embodiment, the precursor solution comprises an excipient. In another embodiment, an excipient is used in a solution to wash the alginate lyase encapsulated alginate beads formed from the precursor solution. In one embodiment, water comprising an excipient is used to wash the alginate lyase encapsulated alginate beads formed from the precursor solution. The alginate can be of predetermined molecular weight and G/M ratio. The concentration of Ca-EDTA or $CaCO_3$ is in the range of 1 M to 0.01 M and the preferable concentration is 0.05 M to 0.1 M.

The activity of the alginate lyase enzyme may range from 0.001 nU/mg to 0.25 U/mg of alginate. For the rapid degradation of alginate microspheres (>=2 days to <=5 days), the preferred activity of the enzyme may range from 0.5 mU/mg to 0.25 U/mg of alginate. To get intermediate (>5 days to <=30 days) or slow (>30 days) degradation periods, the preferred range of enzyme activity may be <0.5 mU/mg to >0.1 μU/mg of alginate and <0.1 μU/mg to >0.001 nU/mg of alginate respectively.

The buffer solution has a pH range of 8.0-13.0, and the preferred range of buffer is 9.0-11.0. The common buffer system that can be used to prepare the alginate, alginate lyase and Ca-EDTA solution are disodium hydrogen phthalate/Sodium dihydrogen orthophosphate, Barbitone sodium/Hydrochloric acid, Dipotassium hydrogen phthalate/Potassium dihydrogen orthophosphate, Potassium dihydrogen orthophosphate/sodium hydroxide, Barbitone sodium/Hydrochloric acid, Tris (hydroxylmethyl) aminomethane/Hydrochloric acid, Sodium tetraborate/Hydrochloric acid, Glycine/Sodium hydroxide, Sodium carbonate/Sodium hydrogen carbonate, Sodium tetraborate/Sodium hydroxide, Sodium bicarbonate/Sodium hydroxide, Sodium hydrogen orthophosphate/Sodium hydroxide and Potassium chloride/Sodium hydroxide. The most preferred buffer system is Sodium bicarbonate/Sodium hydroxide. The ionic strength of the buffer is <1 M, and the preferred range is <0.5 M to >0.05 M, and most preferably ≤0.1 M. The preferred temperature range is <10° C. and most preferably >1° C. to <4° C. The above-said conditions allow the generation of alginate droplets and overcome the challenges that are encountered with the conventional method to prepare alginate lyase encapsulated beads in two ways—(a) these conditions inhibit the activity of the alginate lyase enzyme thus preventing the initial degradation of alginate in the precursor solution and (b) these conditions prevent the release of $Ca^{2+}$ ion from Ca-EDTA or $CaCO_3$. Furthermore, the precursor solution along with oil passes through a suitable microfluidics chip to form alginate droplets (water-in-oil emulsion method). These droplets are crosslinked by a bivalent $Ca^{2+}$ ion by exposing them to acetic acid of concentration 0.01% v/v to 5% v/v. The preferred range of acetic acid concentration is 1%-2% v/v of acetic acid. On exposing to acetic acid, the $Ca^{2+}$ ion gets released from Ca-EDTA or $CaCO_3$ and binds with egg-boxes of alginate to form $Ca^{2+}$ crosslinked alginate lyase loaded alginate beads. These beads are then washed with deionized water containing excipients to remove the acid. If required, the beads are further crosslinked in a calcium chloride solution of concentration ranging from 2% w/v to 10% w/v. The washed beads are suspended in a solution containing excipients for the duration of 6-24 hours and subjected to freeze drying. The freeze-dried particles can be reconstituted in a neutral pH buffer to activate the alginate lyase enzyme and initiate the degradation of the alginate beads.

Lyophilization and Sterilization

The shelf-life of the self-degradable alginate microspheres containing alginate lyase and hyaluronic acid may be improved through the lyophilization and sterilization of lyophilized product. For these post-preparation process, cryoprotectants may be added into precursor solution and gelling bath. The addition of cryoprotectants is important in many ways. Firstly, it helps in maintaining the sphericity and mechanical robustness of the alginate lyase loaded alginate particles during lyophilization process. Secondly, it preserves the 3D conformation of the enzyme at extremely low temperatures and freezing cycles, thereby preserving the enzyme activity. Recovery of microsphere shape post lyophilization was considered as an issue. This is not unexpected, as high-water content gels shrink during lyophilization and often do not re-establish their original shape upon rehydration. The addition of cryoprotectants such as sugars and polymers can compensate for this, to help maintain the porous structure during sublimation of the internal water within the structure. Also, it has been observed that the residual activity of the enzyme reduced significantly when the lyophilization of the enzymes was performed without the addition of the cryoprotectants/cryopreservation medium [12, 13]. Thus, the use of cryoprotectants also assists the rapid recovery of shape upon reconstitution in aqueous medium and enables retention of the functionality of the active ingredients including enzymes.

Composition of precursor and gelling solution containing cryoprotectants. Untreated or pre-treated precursor alginate lyase enzyme-sodium alginate and gelling solutions (as described in section 4.1 and 4.2) may be mixed with cryoprotectants at different proportions such as hydroxypropyl-beta cyclodextrin, trehalose, polyvinyl pyrrolidone of 40 kDa (PVP 40 kDa) and dextran (70 kDa molecular weight).

Table 1 describes the composition of cryoprotectants in precursor and gelling bath solutions. The preferred concentration of cryoprotectants for precursor solution and gelling bath is described as % w/v of alginate concentration may be from 0.1% w/v to 4% w/v and 0.1% w/v to % w/v for divalent metal ion concentration, respectively. The concentration of trehalose, Hydroxypropyl-β-cyclodextrin, PVP (molecular weight 40 kDa) and dextran (molecular weight kDa) may have range from 0.1% w/v to 20% w/v, 0.1% w/v to 2% w/v, 0.1% w/v to 1% w/v and 0.1% w/v to 1% w/v respectively.

These cryoprotectants components may be mixed with the untreated and pre-treated precursor solutions for 15 min to 1 hours before adding into gelling bath containing cryoprotectants for crosslinking with divalent metal ion to form alginate microspheres containing alginate lyase and cryoprotectants. These microspheres may be subjected to a lyophilization cycle to obtain freeze-dried particles with the moisture content 3% by mass or less, preferably 2% by mass or less and more preferably 1% by mass or less. Under dry conditions sealed in a vial, the dried particles may be further subjected to the high-energy radiation sterilization (gamma or e-beam radiation). These lyophilized and sterilized alginate lyase loaded divalent metal ion-crosslinked alginate microspheres can be stored for ≤24 months.

Additional Embodiments

The concentration of purified alginate or oxidized form of alginate can also affect the pore size and robustness of the divalent complexed alginate bead. The concentration of the alginate can be about 0.05% weight by volume (w/v), 0.10% w/v, 0.15% w/v, 0.20% w/v, 0.25% w/v, 0.30% w/v, 0.35% w/v, 0.40% w/v, 0.45% w/v, 0.50% w/v, 0.60% w/v, 0.70% w/v, 0.80% w/v, 0.90% w/v, 1.0% w/v, 1.25% w/v, 1.5% w/v, 1.75% w/v, 2.0% w/v, 2.25% w/v, 2.5% w/v, 2.75% w/v, 3.0% w/v, 3.25% w/v, 3.5% w/v, 3.75% w/v, 4% w/v, 4.25% w/v, 4.5% w/v, 4.75% w/v, 5.0% w/v, 5.25% w/v, 5.5% w/v, 5.75% w/v, 6.0% w/v, or greater than about 6.0% w/v for the preparation of rapid (>=2 days to <=5 days) and slow degrading (>5 days to <=30 days) alginate lyase loaded divalent metal ion complexed alginate particles.

In addition, the gelling time during which the alginate particles are crosslinked within the metal ion bath can also affect the size, sphericity and physical robustness of the divalent metal ion complexed alginate particles. Generally, the term "sphericity" can refer to a measure of how closely the shape of an object resembles that of a perfect sphere. The roundness of an injectable substance can be important, for example, as abnormally shaped substances can have difficulty in travelling through blood vessels, leading to clogged blood vessels, thereby blocking blood flow to various parts of the body The gelling time can be less than about 1 min, less than about 2 minutes, less than about 3 minutes, less than about 4 minutes, less than about 5 minutes, less than about 6 minutes, less than about 7 minutes less than about 8 minutes, less than about 9 minutes, less than about 10 minutes, less than about 11 minutes, less than about 12 minutes, less than about 13 minutes, less than about 14 minutes, less than about 15 minutes, less than about 20 minutes, less than about 25 minutes, or less than about 30 minutes.

To achieve the desired degradation period of the alginate lyase loaded alginate particles, the amount of enzyme mixed with preferred alginate may be varied. The amount of alginate lyase mixed with the alginate varies from <1 unit to 50 units/ml of sodium alginate for the preparation of rapid (>=2 days to <=5 days) intermediate (>5 days to <=30 days), or slow (>30 days) degrading divalent metal ion complexed alginate particles. For the sake of clarity, in enzymology 1 unit (U) is the amount of enzyme that catalyzes the reaction of 1 μmol of substrate per minute. The amount of enzyme loading into the divalent metal ion complexed alginate particles also depends on the molecular weight or viscosity of the sodium alginate.

In certain embodiments, the activity of the alginate lyase enzyme is about 0.001 nanounits (nU) per particle, about 0.01 nU per particle, about 0.10 nU per particle, about 0.50 nU per particle, about 0.001 milliunits (mU) per particle, about 0.01 mU per particle, about 0.05 mU per particle, about 0.10 mU per particle, about 0.25 mU per particle, about 0.50 mU per particle, about 0.75 mU per particle, about 1.0 mU per particle, about 1.25 mU per particle, about 1.5 mU per particle, about 1.75 mU per particle, about 2.0 mU per particle, about 2.25 mU per particle, about 2.5 mU per particle, about 2.75 mU per particle, about 3.0 mU per particle, about 3.25 mU per particle, about 3.5 mU per particle, about 3.75 mU per particle, about 4.0 mU per particle, or a range between any two values thereof. In certain embodiments, the activity of the alginate lyase enzyme is between about 0.001 mU and 4.0 mU per particle. In certain embodiments, the activity of the alginate lyase enzyme is between about 0.01 mU and 3 mU per particle. In certain embodiments, the activity of the alginate lyase enzyme is between about 0.05 mU and 2.5 mU per particle. In certain embodiments, the activity of the alginate lyase enzyme is between about mU and 0.5 mU per particle. In certain embodiments, the activity of the alginate lyase enzyme is between about 0.5 mU and 1.0 mU per particle. In certain embodiments, the activity of the alginate lyase enzyme is between about 1.0 mU and 1.5 mU per particle. In certain embodiments, the activity of the alginate lyase enzyme is between about 1.5 mU and 2.0 mU per particle. In certain embodiments, the activity of the alginate lyase enzyme is between about 2.0 mU and 2.5 mU per particle. The per particle activity of the alginate lyase enzyme can be determined as a function of the amount of alginate used to create X number of particles, and the amount of enzyme used to prepare X particles. For example, the per particle activity of the alginate lyase enzyme can be determined to be between about 0.05 mU and 2.5 mU per particle, based upon 100 mg of alginate being converted to 20,000 particles, containing between about 1 to about 50 Units of enzyme.

Furthermore, the degradation of enzyme-loaded alginate particles could also be controlled by regulating the alginate lyase enzyme activity. In order to control the catalytic degradation activity of alginate lyase, the enzyme may be complexed or pre-treated with <1 mM of $Cu^{2+}$, $Zn^{2+}$ and $Fe^{2+}$ metal ions. These metal ions can inhibit enzymatic activity by approximately 90%. Other metal ions such as $Mg^{2+}$ and $Ca^{2+}$ at 1 mM concentration reduces the activity by 20% to 50% respectively. The free or unbound metal ions may be removed from the solution through dialysis. These metal ions can inhibit the activity of the enzyme and can be considered detrimental for the enzyme (Inoue, et al., "Functional identification of alginate lyase from the brown alga *Saccharina japonica*", Sci. Rep. 2019; 9:1-11). On the contrary, the same concept is adopted in certain embodiments of the present disclosure to regulate the degradation of alginate lyase loaded alginate particles. Importantly, this enzyme shows optimum enzymatic activity at physiological temperature and pH. Thus, under in vivo conditions, the enzymatic activity could be regulated solely using these metal ions to achieve the rapid (>=2 days to <=5 days) and longer (>5 days to <=30 days or >30 days) duration degrading particles.

In general, an enzyme may be immobilized into an inert or insoluble matrix. This provides resistance to physiological factors affecting the enzymatic reactions such as pH or temperature and also increase the rate of reaction. It also keeps the enzyme localized in a place (e.g, inside the particles, surface decorated, etc.). In certain embodiments of the present disclosure, immobilization/encapsulation of the modified or native alginate lyase enzyme to its sodium alginate substrate (reactive, instead of an inert matrix). Therefore, another important aspect is to avoid the initial degradation during the manufacturing of the alginate lyase loaded alginate particles from the alginate lyase-sodium alginate precursor solution. To overcome this problem following approaches are proposed for use in certain embodiments of the present disclosure.

The enzyme may be pre-treated with the metal ions inhibitors such as $Cu^{2+}$, $Zn^{2+}$, $Fe^{2+}$, $Mg^{2+}$ and $Ca^{2+}$. These metal ions at optimum concentration without affecting the physical robustness of the particles may reduce the degradation of the particles by partially inhibiting the enzyme activity.

Another approach is to reduce the temperature of the alginate lyase-sodium alginate precursor solution from ambient to a temperature ranging from 4 to 10° C. This will reduce or cease the catalytic activity of the alginate lyase, thereby preventing the degradation of sodium alginate. In addition, the temperature of the divalent metal ions gelling bath may also be reduced to the range of 1 to 10° C. This metal ion bath is used for gelling the droplets of sodium alginate-alginate lyase solution to form the divalent metal ions-complexed alginate lyase loaded sodium alginate particles.

The catalytic activity of alginate lyase may also be regulated by changing the pH of the alginate lyase-sodium alginate and gelling bath solutions. The optimum catalytic activity of this enzyme is observed at pH ranging from 6.8 to 7.5 (see, e.g., Farrés, et al., "Formation kinetics and rheology of alginate fluid gels produced by in-situ calcium release", Food Hydrocolloids 40 (2014): 76-84). To prevent the initial degradation of sodium alginate during the preparation of alginate lyase loaded alginate particles, the pH of the alginate lyase-sodium alginate solution may be reduced to 3.0. To carry out this process, sodium acetate-acetic acid buffer, of ionic strength <1 M, preferably <0.1 M and most preferably <0.01M with a pH range 3.7-5.6. In addition, the desired pH (pH 6.5 to 3.0) of the solution may also be achieved using sodium hydroxide (>1M to <0.01M) or hydrochloric acid (>1M to <0.01M). This results in the reduction or ceasing of the alginate lyase catalytic activity. This regulation of the catalytic activity may be attributed to the unfolding of 3D conformation of alginate lyase enzyme. The ceased catalytic activity of the alginate lyase enzyme may be reversed/activated by exposing alginate lyase loaded alginate particles to the aqueous environment having pH 6.5 to 7.5 The preferred buffer to reverse the activity of the alginate lyase enzyme is phosphate buffers. The preferred ionic strength of the phosphate buffer is 0.01 M with a pH range of 6.5 to 7.5 at 20° C. The desired pH (pH 6.5 to 7.5) of the solution may also be achieved using sodium hydroxide (>1M to <0.01M) or hydrochloric acid (>1M to <0.01M). Additionally, saline or de-ionized water or an aqueous solution having a pH between 6.5-7.5 may also be used.

Therefore, a combination of the abovementioned approaches may be used efficiently to encapsulate or load the alginate lyase enzyme into the alginate particles-complexed/gelled with divalent metal ions without degrading the alginate matrix.

The precursor alginate lyase enzyme-sodium alginate solution under the appropriate conditions (low temperature and pH) needs to be gelling in a divalent metal ions bath containing one or more cryoprotectants. The composition and condition of the gelling bath are important to make desired alginate-based embolic particles. The divalent metal ion component of the gelling bath composition may be selected from the group consisting $Cu^{2+}$, $Ba^{2+}$, $Sr^{2+}$, $Ca^{2+}$, $Co^{2+}$, $Ni^{2+}$, $Mn^{2+}$ and $Mg^{2+}$ (Lee, et al., "Alginate: properties and biomedical applications," Progress in polymer science 37, no. 1 (2012): 106-126; and Brus, et al., "Structure and dynamics of alginate gels cross-linked by polyvalent ions probed via solid state NMR spectroscopy," Biomacromolecules 18, no. 8 (2017): 2478-2488). Divalent cation choice may also influence alginate matrix crosslinking. The binding strength of divalent metal ion with alginate is given in decreasing order $Cu^{2+}>Ba^{2+}>Sr^{2+}>Ca^{2+}>Co^{2+}>Ni^{2+}>Mn^{2+}>Mg^{2+}$. The preferred metal cations are $Ba^{2+}$ and $Ca^{2+}$. These metal ions may be used at different concentrations ranging from 0.1% w/v to 10% w/v. The addition of cryoprotectants in the gelling bath is important in two ways: (a) it helps in maintaining the sphericity and mechanical robustness of the alginate lyase loaded alginate particles during lyophilization process and (b) it also preserves the 3D conformation of the enzyme in extremely low temperatures and freezing cycles, thereby preserving the enzyme activity.

In many instances, it has been observed that the residual activity of the enzyme reduced significantly when the lyophilization of the enzymes was performed without the addition of the cryoprotectants/cryopreservation medium (Tamiya, et al., "Freeze denaturation of enzymes and its prevention with additives," Cryobiology 22, no. 5 (1985): 446-456; and Porter, et al., "Effects of freezing on particulate enzymes of rat liver," J. Biol. Chem 205 (1953): 883-891). The cryoprotectant components may include those known in the art, such as sucrose, glycerol, ethylene glycol, sorbitol, trehalose, propylene glycol or proprietary/commercially available cryoprotectants. When these cryoprotectants are added into the gelling bath, it gets encapsulated or uniformly distributed in the matrix of sodium alginate particles (Chan, et al., "Effects of starch filler on the physical properties of lyophilized calcium-alginate beads and the viability of encapsulated cells," Carbohydrate polymers 83, no. 1 (2011): 225-232).

Additionally, a cryoprotectant may also be used in the post-processing stage of the preparation of freeze-dried alginate lyase loaded alginate particles, instead of adding during the manufacturing process of these particles in the gelling bath containing-divalent metal ions. In this process, the droplets of the precursor alginate lyase-sodium alginate solution added into the gelling bath containing divalent metal ion only to form alginate-lyse loaded alginate particles. Following the isolation of these particles from the gelling bath, it may be soaked in a suitable cryoprotectant and subject to the freeze-drying process. Under the freeze-drying conditions, it prevents the freeze denaturation of the enzyme as well as providing the defect-free alginate lyase loaded alginate particles by preventing the collapse of the gel structure by filling the pores formed as the water is sublimed out of the matrix. The particle size may be >40 μm, <200 μm but <2000 μm. Also, this process may be used to prepare alginate-based embolic agent of different morphologies such as microfibrils, core-shell particles, Janus particles or capsules.

Furthermore, in certain embodiments, the present disclosure provides the preparation of both radiopaque and drug-loaded alginate lyase loaded alginate particles. To achieve this, a composition of divalent metal ions containing $Ca^{2+}$ ions and one of the following x-ray contrasting metal ions such as barium, gadolinium and tantalum metal ions (Yu, et al., "Metal-based X-ray contrast media," Chemical Reviews 99, no. 9 (1999): 2353-2378) is proposed to be used in the gelling bath. Another proposed approach is the reconstitution of alginate lyase loaded alginate particles with commercially available radiopaque agents, which become temporarily absorbed into the matrix as the alginate matrix swells in the aqueous medium. The proposed method of loading the drugs/bioactive agents (anticancer and osteogenic) into alginate lyase loaded alginate particles involve the exposing these particles to the drug for 2 to 3 hours. The delivery of the drug in the body will be facilitated by the in situ degradation mechanism of alginate lyase loaded alginate particles.

In certain embodiments, enzyme loaded alginate microspheres may be stored over extended periods of time. In certain embodiments, metal ion complexed-enzyme is immobilized into its substrate. It is contemplated that the slow degradation of the matrix starts during storage condition. This degradation may be stopped by suspending the microspheres in the pH below 5.5. Apart from reducing the operating temperature below 10° C. to prevent the degradation of alginate microspheres, an alternative method is to freeze or vacuum dry these microspheres. This may stop the degradation of alginate microspheres. In certain embodiments, the dried spheres may be loaded into a specially designed syringe.

Figure 18:
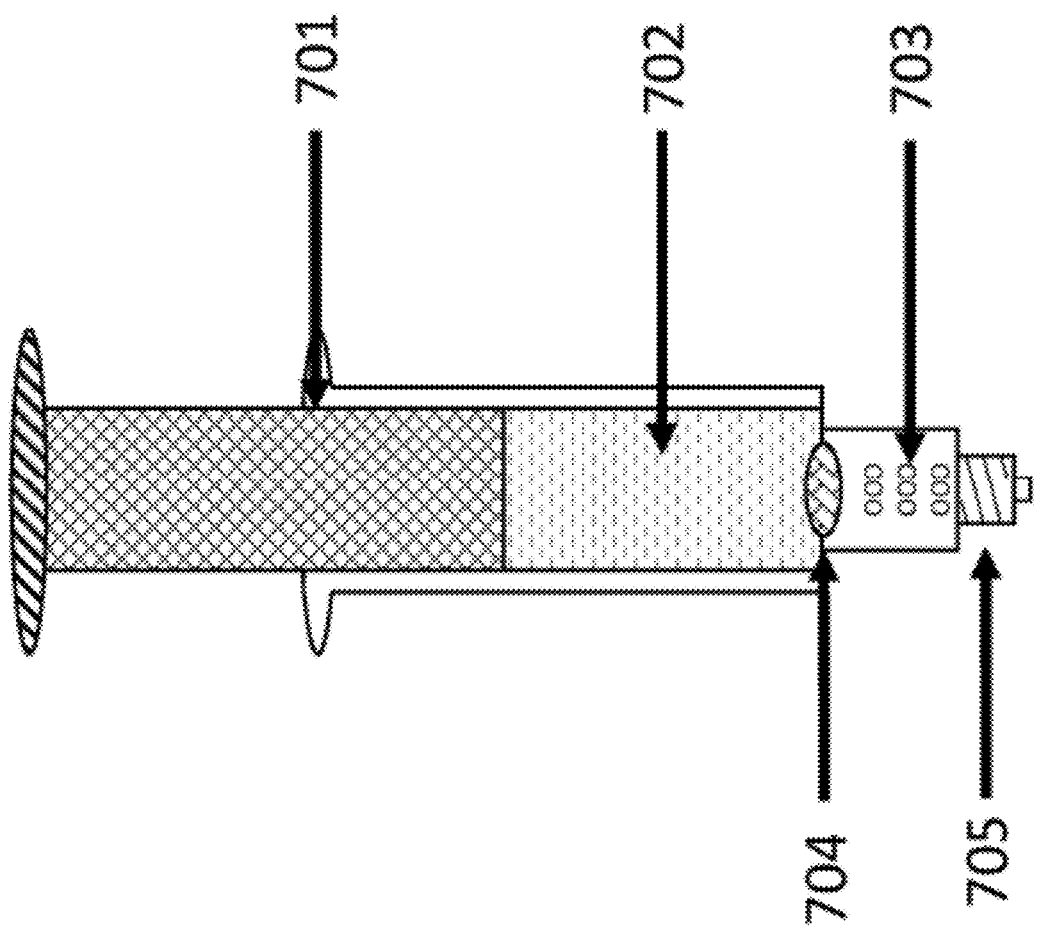
FIG. 18 illustrates an exemplary syringe showing the compartments for the suspension medium and dried alginate microspheres. The separating membrane may be torn inside the syringe by applying pressure on the plunger, thereby reconstituting the dried alginate microsphere in the suspension medium containing calcium chloride solution.

FIG. 18 illustrates a proposed design of a syringe for reconstituting and/or administering microspheres. The syringe may comprise a plunger 701, which may be in a locked or unlocked position. The syringe may also comprise a first chamber comprising a suspension medium 702, a second chamber comprising dried microspheres 703. Generally, the syringe may be constructed and arranged such that the contents of each of the chambers of the syringe are separated (e.g., fluidically) until pressure is applied to the plunger, thereby mixing the contents of each chamber (e.g., reconstituting the microspheres). It is contemplated that any multi-chamber lyophilization syringe known in the art may be used. In certain embodiments, the syringe may comprise a breakable membrane 704 separating the first chamber 701 and the second chamber 702. When pressure is applied to the plunger 701, the breakable membrane is broken and the contents of a first chamber comes into contact with the dried microspheres of a second chamber 703 to reconstitute the microspheres. In other embodiments, the syringe comprises a liquid bypass duct. In yet another embodiment, a barrier separating a first chamber and a second chamber of a syringe can comprise a one way valve. When pressure is applied to the plunger 701, the one way valve is forced open and the contents of a first chamber comes into contact with the dried microspheres of a second chamber to reconstitute the microspheres. In some embodiments, the reconstitution medium may be water for injection (WFI). Once reconstituted, the reconstituted microspheres are now ready for use. The syringe can comprise a quick connector 705 (e.g., Luer Lock connector) for connecting tubing or the like to administer the reconstituted microspheres to the subject.

Subjects

A patient treated by any of the methods or compositions described herein may be of any age and may be an adult, infant or child. In some cases, the patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). The patient may be a human or non-human subject.

Any of the compositions disclosed herein may be administered to a non-human subject, such as a laboratory or farm animal. Non-limiting examples of a non-human subject include laboratory or research animals, a dog, a goat, a guinea pig, a hamster, a mouse, a pig, a non-human primate (e.g., a gorilla, an ape, an orangutan, a lemur, or a baboon), a rat, a sheep, or a cow.

Additives and Excipients

In some cases, the alginate particles or microspheres described herein may comprise an excipient that may provide long term preservation, bulk up a formulation that contains potent active ingredients, facilitate drug absorption, reduce viscosity, or enhance the solubility of the alginate particle or microsphere. An alginate particle or microsphere of the present disclosure may comprise about 1%, 2%, 3%, 4%, 5%, 6%, 7%, 8%, 9%, 10%, 15%, 20%, 25%, 30%, 35%, 40%, 45%, 50%, or greater than about 50% of the excipient by weight or by volume.

In certain embodiments, an alginate particle or microsphere of the present disclosure may comprise one or more solubilizers. As used herein, "solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like. An alginate particle or microsphere of the present disclosure may comprise about 1%, 2%, 3%, 4%, 5%, 6%, 7%, 8%, 9%, 10%, 15%, 20%, 25%, 30%, 35%, 40%, 45%, 50%, or greater than about 50% of the solubilizer by weight or by volume.

In some embodiments, the compositions described herein include other medicinal or pharmaceutical agents, carriers, adjuvants, such as preserving, stabilizing, wetting or emulsifying agents, solution promoters, and salts for regulating the osmotic pressure, osmolarity, and/or osmolality of the alginate particle or microsphere. In some embodiments, the compositions comprise a stabilizing agent. In some embodiments, stabilizing agent is selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used.

In some embodiments, the composition comprises a suspending agent. Useful suspending agents include for example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol may have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

In some embodiments, the composition comprises an additional surfactant (co-surfactant) and/or buffering agent and/or solvent. In some embodiments, the surfactant and/or buffering agent and/or solvent is a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens), sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors), sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxyethyleneglycerol triricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof and d) cationic surfactants such as quaternary ammonium compounds, benzalkonium chloride, cetyltrimethylammonium bromide, and lauryldimethylbenzyl-ammonium chloride. It is contemplated that the solvent may be chosen with the intended subject in mind.

In some embodiments, the compositions disclosed herein comprise preservatives. Suitable preservatives for use in the compositions described herein include, but are not limited to benzoic acid, boric acid, p-hydroxybenzoates, phenols, chlorinated phenolic compounds, alcohols, quaternary compounds, quaternary ammonium compounds (e.g., benzalkonium chloride, cetyltrimethylammonium bromide or cetylpyridinium chloride), stabilized chlorine dioxide, mercurials (e.g., merfen or thiomersal), or mixtures thereof.

Other Embodiments and Equivalents

The section headings used herein are for organizational purposes only and are not to be construed as limiting the subject matter described.

It is to be understood that the methods described herein are not limited to the particular methodology, protocols, subjects, and sequencing techniques described herein and as such may vary. It is also to be understood that the terminology used herein is for the purpose of describing particular embodiments only, and is not intended to limit the scope of the methods and compositions described herein, which will be limited only by the appended claims. While some embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment may be combined with any other embodiment. It should be understood that numerous specific details, relationships, and methods are set forth to provide a full understanding of the features described herein. A skilled artisan, however, will readily recognize that the features described herein may be practiced without one or more of the specific details or with other methods. The features described herein are not limited by the illustrated ordering of acts or events, as some acts may occur in different orders and/or concurrently with other acts or events. Furthermore, not all illustrated acts or events are required to implement a methodology in accordance with the features described herein. Further, to the extent that the methods of the present disclosure do not rely on the particular order of steps set forth herein, the particular order of the steps should not be construed as limitation on the claims. Any claims directed to the methods of the present disclosure should not be limited to the performance of their steps in the order written, and one skilled in the art may readily appreciate that the steps may be varied and still remain within the spirit and scope of the present disclosure.

While some embodiments have been shown and described herein, it will be obvious to those skilled in the art that such embodiments are provided by way of example only. It is not intended that embodiments of the present disclosure be limited by the specific examples provided within the specification. While certain embodiments of the present disclosure have been described with reference to the aforementioned specification, the descriptions and illustrations of the embodiments herein are not meant to be construed in a limiting sense. Numerous variations, changes, and substitutions will now occur to those skilled in the art without departing from the disclosure.

Furthermore, it shall be understood that all aspects of the embodiments of the present disclosure are not limited to the specific depictions, configurations or relative proportions set forth herein which depend upon a variety of conditions and variables. It should be understood that various alternatives to the embodiments of the disclosure described herein may be employed in practicing the invention. It is therefore contemplated that the disclosure shall also cover any such alternatives, modifications, variations or equivalents. It is intended that the following claims define, at least in part, the scope of the invention and that methods and structures within the scope of these claims and their equivalents be covered thereby.

It will be appreciated by those skilled in the art that changes could be made to the exemplary embodiments shown and described above without departing from the broad inventive concepts thereof. It is understood, therefore, that this disclosure is not limited to the exemplary embodiments shown and described, but it is intended to cover modifications within the spirit and scope of the present disclosure as defined by the claims. For example, specific features of the exemplary embodiments may or may not be part of the claimed invention and various features of the disclosed embodiments may be combined. The words "right", "left", "lower" and "upper" designate directions in the drawings to which reference is made. The words "inwardly" and "outwardly" refer to directions toward and away from, respectively, the geometric center of the fluid delivery device. Unless specifically set forth herein, the terms "a", "an" and "the" are not limited to one element but instead should be read as meaning "at least one".

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

It is to be understood that at least some of the figures and descriptions of the disclosure have been simplified to focus on elements that are relevant for a clear understanding of the disclosure, while eliminating, for purposes of clarity, other elements that those of ordinary skill in the art will appreciate may also comprise a portion of the disclosure. However, because such elements are well known in the art, and because they do not necessarily facilitate a better understanding of the disclosure, a description of such elements is not provided herein.

The following clauses describe certain embodiments of the disclosure.

Clause 1. An alginate microsphere capable of self-degradation upon rehydration, comprising:
an alginate lyase enzyme pre-treated by varying temperature, by varying pH, and/or with a metal-ion enzyme inhibitor;
alginate molecules having one or both of (i) a predetermined molecular weight, and (ii) a predetermined ratio of β-D-Mannuronic acid (M) blocks to α-L-Guluronic acid (G) blocks; and
a divalent metal-ion crosslinking the alginate molecules, wherein the alginate microsphere is substantially free of water and/or sterilized.

Clause 2. The alginate microsphere of clause 1, wherein the degradation of alginate microsphere is controlled by one or more of the pre-treatment of the alginate lyase enzyme, amount of the alginate enzyme in the microsphere, the predetermined molecular weight of the alginate molecule, and the predetermined ratio of M:G blocks of the alginate molecules, and a composition of gelling bath, including an amount and or charge of one or more ions in the gelling bath.

Clause 3. The alginate microsphere of clause 1 or 2, wherein the pH of alginate lyase enzyme in the precursor solution containing alginate lyase and alginate, is in the range of pH 3.0 to 6.4, to prevent the degradation of alginate, before crosslinking with divalent metal cation.

Clause 4. The alginate microsphere of any one of clauses 1-3, wherein the metal-ion enzyme inhibitor is a reversible inhibitor selected from the group consisting of $Cu^{2+}$, $Zn^{2+}$, and $Fe^{2+}$ (e.g., to control the degradation of alginate in the precursor solution, before crosslinking with divalent metal cation).

Clause 5. The alginate microsphere of any one of clauses 1-4, wherein the temperature of the precursor solution is in the range of 1-4° C. to control the degradation of alginate, before crosslinking with divalent metal cation.

Clause 6. The alginate microsphere of any one of clauses 1-5, wherein the pre-treatment of the alginate enzyme in the precursor solution allows mixing of a predetermined amount of enzyme (measured in units, U) with the alginate molecules.

Clause 7. The alginate microsphere of any one of clauses 1-6, wherein an activity of the alginate lyase enzyme is modulated by adjusting one or more of a pH of the gelling bath, a temperature of the gelling bath, and an amount of the metal-ion enzyme inhibitor in the alginate microsphere.

Clause 8. The alginate microsphere of any one of clauses 1-7, wherein the degradation of the alginate microsphere is controlled by the predetermined molecular weight of alginate molecules.

Clause 9. The alginate microsphere of any one of clauses 1-8, wherein the predetermined molecular weight of the alginate molecules is in a range of greater than about 100 kDa to less than about 800 kDa.

Clause 10. The alginate microsphere of any one of clauses 1-9, wherein the predetermined ratio of M:G block controls a degradation of alginate microsphere.

Clause 11. The alginate microsphere of any one of clauses 1-10, wherein the predetermined ratio of M:G blocks is about 50:50, about 55:45, about 60:40, about 65:35, about 70:30, about 75:25, about 80:20, about 85:15, about 90:10, or about 95:5.

Clause 12. The alginate microsphere of clause 11, wherein the alginate microsphere degrades over a period of less than about 5 days.

Clause 13. The alginate microsphere of 11 or 12, wherein the alginate microsphere degrades over a period of greater than about 2 days.

Clause 14. The alginate microsphere of any one of clauses 1-10, wherein the predetermined ratio of M:G blocks is about 50:50, about 45:55, about 40:60, about 35:65, about 30:70, about 25:75, about 20:80, about 15:85, about 10:90, or about 5:95.

Clause 15. The alginate microsphere of clause 14, wherein the alginate microsphere degrades over a period of between about 5 days and about 30 days.

Clause 16. The alginate microsphere of any one of clauses 1-15, wherein the pre-treated alginate lyase enzyme is mixed in the precursor solution having enzyme activity ranging from 0.025 U/mg to 1 U/mg of alginate.

Clause 17. The alginate microsphere of any one of clauses 1-16, wherein the activity of the alginate lyase enzyme is between about 0.05 mU (milliunits) and about 2.5 mU per microsphere.

Clause 18. The alginate microsphere of clause 17, wherein the alginate microsphere degrades over a period of less than about 5 days.

Clause 19. The alginate microsphere of any one of clauses 1-16, wherein the activity of the alginate lyase enzyme is between about 0.05 nU (nanounits) and about 0.05 mU per microsphere.

Clause 20. The alginate microsphere of clause 19, wherein the alginate microsphere degrades over a period of between about 5 days and about 30 days.

Clause 21. The alginate microsphere of any one of clauses 1-20, further comprising a bioactive agent.

Clause 22. The alginate microsphere of clause 21, wherein the bioactive agent comprises an anti-inflammatory agent and/or an anesthetic drug to alleviate pain associated with embolization in a subject.

Clause 23. The alginate microsphere of clause 21, wherein the bioactive agent comprises an anti-cancer agent, or an anti-angiogenic agent.

Clause 24. The alginate microsphere of clause 22, wherein the anti-inflammatory agent comprises hyaluronic acid having a molecular weight of between about 1 million (M) and about 5 M Daltons.

Clause 25. The alginate microsphere of clause 24, where in the ratio of hyaluronic acid to the alginate molecules is about 1:20 by weight.

Clause 26. The alginate microsphere of any one of clauses 1-25, further comprising a cryoprotectant selected from the group consisting of hydroxypropyl-β cyclodextrin, trehalose, polyvinyl pyrrolidone of 40 kDa (PVP 40 kDa) and dextran (70 kDa molecular weight).

Clause 27. The alginate microsphere of any one of clauses 1-26, wherein the alginate microsphere is lyophilized.

Clause 28. The alginate microsphere of clause 27, wherein a residual water content of the lyophilized alginate microsphere is in the range of about 1% to about 3% by mass.

Clause 29. The alginate microsphere of any one of clauses 1-28, wherein a sphericity of the alginate microsphere is at least about 0.7, at least about 0.75, at least about 0.8, at least about 0.85, at least about 0.9, at least about 0.95, or at least about 0.99.

Clause 30. The alginate microsphere of any one of clauses 1-29, wherein the alginate microsphere or the lyophilized alginate microsphere is sterilized.

Clause 31. The alginate microsphere of clause 30, wherein the sterilization comprises high energy radiation sterilization, gamma-ray sterilization, or e-beam sterilization.

Clause 32. The alginate microsphere of clause 31, wherein the sterilization comprises between about 15 and about 25 kGy of gamma radiation from Cobalt 60 Isotope, or about 25 kGy of electron beam radiation in accordance with ISO 11137-1:2006.

Clause 33. The alginate microspheres of any one of clauses 1-31, wherein a shelf-life of the alginate microsphere is at least about 3 months, at least about 6 months, at least about 12 months, at least about 18 months, at least about 24 months, at least about 36 months, at least about 48 months, or at least about 60 months when stored at a given temperature.

Clause 34. The alginate microsphere of clause 33, wherein the given temperature is between about 2° C. and about 8° C.

Clause 35. The alginate microsphere of clause 33, wherein the given temperature is about room temperature (RT).

Clause 36. The alginate microsphere of any one of clauses 27-35, wherein the alginate microsphere is reconstituted in saline or saline-radiopaque contrast at physiological pH.

Clause 37. A method of preparing an alginate microsphere capable of self-degradation upon rehydration, the method comprising:
  forming droplets from a precursor solution, the precursor solution comprising: an alginate lyase enzyme pretreated by varying temperature, by varying pH, and/or with a metal-ion enzyme inhibitor; and alginate molecules having one or both of (a) a predetermined molecular weight, and (b) a predetermined ratio of β-D-Mannuronic acid (M) blocks to α-L-Guluronic acid (G) blocks;
  contacting the droplets with a gelling bath comprising a cryoprotectant, and a divalent metal-ion, thereby crosslinking the alginate molecules to form an alginate microsphere; and
  dehydrating, and optionally sterilizing, the alginate microsphere thereby substantially removing water from the microsphere.

Clause 38. The method of clause 37, wherein the precursor solution comprises one or more cryoprotectants.

Clause 39. The method of clause 37 or 38, wherein the gelling bath comprises one or more cryoprotectants.

Clause 40. The method of clause 38 or 39, wherein the cryoprotectant is selected from the group consisting of hydroxypropyl-β cyclodextrin, trehalose, polyvinyl pyrrolidone of 40 kDa (PVP 40 kDa) and dextran (70 kDa molecular weight).

Clause 41. The method of clause 40, wherein the concentration of the trehalose in the precursor solution is about 0.1% w/v to about 20% w/v.

Clause 42. The method of clause 40 or 41, wherein the concentration of the hydroxypropyl-β cyclodextrin is about 0.1% w/v to about 2% w/v.

Clause 43. The method of any one of clauses 40-42, wherein the concentration of the PVP 40 kDa in the precursor solution is about 0.1% w/v to about 1% w/v.

Clause 44. The method of any one of clauses 40-43, wherein the concentration of the dextran (molecular weight 70 kDa) in the precursor solution is about 0.1% w/v to about 1% w/v.

Clause 45. The method of any one of clauses 39-44, wherein the precursor solution and the gelling bath comprise the same cryoprotectant.

Clause 46. The method of clause 45, wherein the precursor solution and the gelling bath comprise the same cryoprotectant at equal or about equal concentrations.

Clause 47. The method of any one of clauses 37-46, wherein the dehydrating comprises lyophilizing the alginate microsphere.

Clause 48. The method of clause 47, wherein a residual water content of the lyophilized alginate microsphere is in the range of about 1% to about 3% by mass.

Clause 49. The method of any one of clauses 37-48, wherein a sphericity of the alginate microspheres is at least about 0.7, at least about 0.75, at least about 0.8, at least about at least about 0.9, at least about 0.95, or at least about 0.99.

Clause 50. The method of any one of clauses 37-49, further comprising sterilizing the alginate microsphere or lyophilized alginate microsphere.

Clause 51. The method of clause 50, wherein the sterilizing comprises high energy radiation sterilization, gamma-ray sterilization, or e-beam sterilization.

Clause 52. The method of clause 51, wherein the sterilizing comprises between about 15 and about 25 kGy of gamma radiation from Cobalt 60 Isotope, or about 25 kGy of electron beam radiation in accordance with ISO 11137-1:2006.

Clause 53. The method of any one of clauses 37-51, further comprising storing the alginate microsphere for at least about 3 months, at least about 6 months, at least about 12 months, at least about 18 months, at least about 24 months, at least about 36 months, at least about 48 months, or at least about 60 months when stored at a given temperature.

Clause 54. The method of any one of clauses 37-53, wherein a shelf-life of the alginate microsphere is at least about 3 months, at least about 6 months, at least about 12 months, at least about 18 months, at least about 24 months, at least about 36 months, at least about 48 months, or at least about 60 months when stored at a given temperature.

Clause 55. The method of clause 53 or 54, wherein the given temperature is between about 2° C. and about 8° C.

Clause 56. The method of clause 53 or 54, wherein the given temperature is about room temperature (RT).

Clause 57. The method of any one of clauses 37-56, further comprising administering the alginate microsphere, the lyophilized alginate microsphere, or the sterilized microsphere to a subject.

Clause 58. The method of clause 57, wherein the step of administering the alginate microsphere, the lyophilized alginate microsphere, or the sterilized microsphere to the subject is preceded by reconstituting the lyophilized alginate microsphere, or the sterilized microsphere in saline or saline-radiopaque contrast at physiological pH.

Clause 59. The method of any one of clauses 37-58, wherein forming the droplets is performed using a method selected from the group consisting of drop casting, spray congealing/spray cooling, spray drying, microfluidic droplet production, and jet-cutting.

Clause 60. The method of any one of clauses 37-59, wherein the degradation of alginate microsphere is controlled by one or more of the pre-treatment of the alginate lyase enzyme, amount of the alginate enzyme in the microsphere, the predetermined molecular weight of the alginate molecule, and the predetermined ratio of M:G blocks of the alginate molecules, and a composition of gelling bath, including an amount and or charge of one or more ions in the gelling bath.

Clause 61. The method of any one of clauses 37-60, wherein the pH of alginate lyase enzyme in the precursor solution containing alginate lyase and alginate, is in the range of pH 3.0 to 6.4, to prevent the degradation of alginate, before crosslinking with divalent metal cation.

Clause 62. The method of any one of clauses 37-60, wherein the metal-ion enzyme inhibitor is a reversible inhibitor selected from the group consisting of $Cu^{2+}$, $Zn^{2+}$, and $Fe^{2+}$ (e.g., to control the degradation of alginate in the precursor solution, before crosslinking with divalent metal cation).

Clause 63. The method of any one of clauses 37-62, wherein the temperature of the precursor solution is in the range of 1-4° C. to control the degradation of alginate, before crosslinking with divalent metal cation.

Clause 64. The method of any one of clauses 37-62, wherein the pre-treatment of the alginate enzyme in the precursor solution allow mixing of a predetermined amount of enzyme (measured in units, U) with the alginate molecules.

Clause 65. The method of any one of clauses 37-64, wherein an activity of the alginate lyase enzyme is modulated by adjusting one or more of a pH of the gelling bath, a temperature of the gelling bath, and an amount of the metal-ion enzyme inhibitor in the alginate microsphere.

Clause 66. The method of any one of clauses 37-64, wherein the degradation of the alginate microsphere is controlled by the predetermined molecular weight of alginate molecules.

Clause 67. The method of any one of clauses 37-66, wherein the predetermined molecular weight of the alginate molecules is in a range of greater than about 100 kDa to less than about 800 kDa.

Clause 68. The method of any one of clauses 37-67, wherein the predetermined ratio of M:G block controls a degradation of alginate microsphere.

Clause 69. The method of any one of clauses 37-68, wherein the predetermined ratio of M:G blocks is about 50:50, about 55:45, about 60:40, about 65:35, about 70:30, about about 80:20, about 85:15, about 90:10, or about 95:5.

Clause 70. The method of clause 69, wherein the alginate microsphere degrades over a period of less than about 5 days.

Clause 71. The method of clause 69 or 70, wherein the alginate microsphere degrades over a period of greater than about 2 days.

Clause 72. The method of any one of clauses 37-68, wherein the predetermined ratio of M:G blocks is about 50:50, about 45:55, about 40:60, about 35:65, about 30:70, about about 20:80, about 15:85, about 10:90, or about 5:95.

Clause 73. The method of clause 72, wherein the alginate microsphere degrades over a period of between about 5 days and about 30 days.

Clause 74. The method of any one of clauses 37-73, wherein the pre-treated alginate lyase enzyme is mixed in the precursor solution having enzyme activity ranging from U/mg to 1 U/mg of alginate.

Clause 75. The method of any one of clauses 37-74, wherein the pre-treated alginate lyase enzyme is mixed in the precursor solution having enzyme activity ranging from U/mg to 0.250 U/mg of alginate.

Clause 76. The method of clause 75, wherein the alginate microsphere degrades over a period of less than about 5 days.

Clause 77. The method of any one of clauses 37-74, wherein the pre-treated alginate lyase enzyme is mixed in the precursor solution having enzyme activity ranging from U/mg to 0.125 U/mg of alginate.

Clause 78. The method of clause 77, wherein the alginate microsphere degrades over a period of between about 5 days and about 30 days.

Clause 79. The method of any one of clauses 37-74, wherein the pre-treated alginate lyase enzyme is mixed in the precursor solution having enzyme activity ranging from U/mg to 0.005 U/mg of alginate.

Clause 80. The method of clause 79, wherein the alginate microsphere degrades over a period of greater than about 30 days.

Clause 81. The method of any one of clauses 37-80, wherein the precursor solution and/or the gelling bath further comprises a bioactive agent.

Clause 82. The method of clause 81, wherein the bioactive agent comprises an anti-inflammatory agent and/or an anesthetic agent to alleviate pain associated with embolization in a subject.

Clause 83. The method of clause 81, wherein the bioactive agent comprises an anti-cancer agent, or an anti-angiogenic agent.

Clause 84. The method of clause 83, wherein the anti-inflammatory agent comprises hyaluronic acid having a molecular weight of between about 1 million (M) and about M Daltons.

Clause 85. The method of clause 84, where in the ratio of hyaluronic acid to the alginate molecules is about 1:20 by weight.

Clause 86. The method of any one of clauses 37-85, wherein a pH of the gelling bath is less than about 6.5.

Clause 87. The method of any one of clauses 37-85, wherein a pH of the gelling bath is equal to or about equal to a pH of the precursor solution.

Clause 88. The method of any one of clauses 37-87, wherein a temperature of the precursor solution is equal to or about equal to between 1° C. and about 4° C.

Clause 89. A photopolymerized, alginate microsphere capable of self-degradation upon rehydration, comprising:
an alginate lyase enzyme pre-treated by varying temperature, by varying pH, and/or with a metal-ion enzyme inhibitor;
alginate molecules functionalized with an ethylenically unsaturated functional group, the molecules having one or both of (i) a predetermined molecular weight, and (ii) a predetermined ratio of β-D-Mannuronic acid (M) blocks to α-L-Guluronic acid (G) blocks; and
a photoinitiator,
wherein the alginate molecules are crosslinked by irradiating the photoinitiator, and
wherein the alginate microsphere is substantially free of water and/or sterilized.

Clause 90. The alginate microsphere of clause 89, wherein the ethylenically unsaturated functional group is selected from the group consisting of acrylate, methacrylate, vinylic, and allylic.

Clause 91. The alginate microsphere of clause 89 or 90, wherein the degradation of alginate microsphere is controlled by one or more of the pre-treatment of the alginate lyase enzyme, the predetermined molecular weight of the alginate molecule, and the predetermined ratio of M:G blocks of the alginate molecules, and a composition of gelling bath, including an amount and or charge of one or more ions in the gelling bath.

Clause 92. The alginate microsphere of any one of clauses 89-91, wherein the pH of alginate lyase enzyme in the precursor solution containing alginate lyase and alginate, is in the range of pH 3.0 to 6.4, to prevent the degradation of alginate, before crosslinking with divalent metal cation.

Clause 93. The alginate microsphere of any one of clauses 89-91, wherein the metal-ion enzyme inhibitor is a reversible inhibitor selected from the group consisting of $Cu^{2+}$, $Zn^{2+}$, and $Fe^{2+}$ (e.g., to control the degradation of alginate in the precursor solution, before crosslinking with divalent metal cation).

Clause 94. The alginate microsphere of any one of clauses 89-93, wherein the temperature of the precursor solution is in the range of 1-4° C. to control the degradation of alginate, before crosslinking with divalent metal cation.

Clause 95. The alginate microsphere of any one of clauses 89-93, wherein the pre-treatment of the alginate enzyme in the precursor solution allows mixing of a predetermined amount of enzyme (measured in units, U) with the alginate molecule.

Clause 96. The alginate microsphere of any one of clauses 89-95, wherein an activity of the alginate lyase enzyme is modulated by adjusting one or more of a pH of the gelling bath, a temperature of the gelling bath, and an amount of the metal-ion enzyme inhibitor in the alginate microsphere.

Clause 97. The alginate microsphere of any one of clauses 89-96, wherein the degradation of the alginate microsphere is controlled by the predetermined molecular weight of alginate molecules.

Clause 98. The alginate microsphere of any one of clauses 89-96, wherein the predetermined molecular weight of the alginate molecules is in a range of greater than about 100 kDa to less than about 800 kDa.

Clause 99. The alginate microsphere of any one of clauses 89-98, wherein the predetermined ratio of M:G block controls a degradation of alginate microsphere.

Clause 100. The alginate microsphere of any one of clauses 89-99, wherein the predetermined ratio of M:G blocks is about 50:50, about 55:45, about 60:40, about 65:35, about about 75:25, about 80:20, about 85:15, about 90:10, or about 95:5.

Clause 101. The alginate microsphere of clause 100, wherein the alginate microsphere degrades over a period of less than about 5 days.

Clause 102. The alginate microsphere of clause 100 or 101, wherein the alginate microsphere degrades over a period of greater than about 2 days.

Clause 103. The alginate microsphere of any one of clauses 89-99, wherein the predetermined ratio of M:G blocks is about 50:50, about 45:55, about 40:60, about 35:65, about about 25:75, about 20:80, about 15:85, about 10:90, or about 5:95.

Clause 104. The alginate microsphere of clause 103, wherein the alginate microsphere degrades over a period of between about 5 days and about 30 days.

Clause 105. The alginate microsphere of any one of clauses 89-104, wherein the pre-treated alginate lyase enzyme is mixed in the precursor solution having enzyme activity ranging from 0.025 U/mg to 1 U/mg of alginate.

Clause 106. The alginate microsphere of any one of clauses 89-105, wherein the activity of the alginate lyase enzyme is between about 0.05 mU (milliunits) and about 2.5 mU per microsphere.

Clause 107. The alginate microsphere of clause 106, wherein the alginate microsphere degrades over a period of less than about 5 days.

Clause 108. The alginate microsphere of any one of clauses 89-105, wherein the activity of the alginate lyase enzyme is between about 0.05 nU (nanounits) and about 0.05 mU per microsphere.

Clause 109. The alginate microsphere of clause 108, wherein the alginate microsphere degrades over a period of between about 5 days and about 30 days.

Clause 110. The alginate microsphere of any one of clauses 89-109, further comprising a bioactive agent.

Clause 111. The alginate microsphere of clause 110, wherein the bioactive agent comprises an anti-inflammatory agent to alleviate pain associated with embolization in a subject.

Clause 112. The alginate microsphere of clause 111, wherein the anti-inflammatory agent comprises hyaluronic acid having a molecular weight of between about 1 million (M) and about 5 M Daltons.

Clause 113. The alginate microsphere of clause 112, where in the ratio of hyaluronic acid to the alginate molecules is about 1:20 by weight.

Clause 114. The alginate microsphere of any one of clauses 89-113, further comprising a cryoprotectant selected from the group consisting of hydroxypropyl-β cyclodextrin, trehalose, polyvinyl pyrrolidone of 40 kDa (PVP 40 kDa) and dextran (70 kDa molecular weight).

Clause 115. The alginate microsphere of any one of clauses 89-114, wherein the alginate microsphere is lyophilized.

Clause 116. The alginate microsphere of clause 103, wherein a residual water content of the lyophilized alginate microsphere is in the range of about 1% to about 3% by mass.

Clause 117. The alginate microsphere of any one of clauses 89-116, wherein a sphericity of the alginate microsphere is at least about 0.7, at least about 0.75, at least about 0.8, at least about 0.85, at least about 0.9, at least about 0.95, or at least about 0.99.

Clause 118. The alginate microsphere of any one of clauses 89-117, wherein the alginate microsphere or the lyophilized alginate microsphere is sterilized.

Clause 119. The alginate microsphere of clause 118, wherein the sterilization comprises high energy radiation sterilization, gamma-ray sterilization, or e-beam sterilization.

Clause 120. The alginate microsphere of clause 119, wherein the sterilization comprises between about 15 and about 25 kGy of gamma radiation from Cobalt 60 Isotope, or about 25 kGy of electron beam radiation in accordance with ISO 11137-1:2006.

Clause 121. The alginate microsphere of any one of clauses 89-120, wherein a shelf-life of the alginate microsphere is at least about 3 months, at least about 6 months, at least about 12 months, at least about 18 months, at least about 24 months, at least about 36 months, at least about 48 months, or at least about 60 months when stored at a given temperature.

Clause 122. The alginate microsphere of clause 121, wherein the given temperature is between about 2° C. and about 8° C.

Clause 123. The alginate microsphere of clause 121, wherein the given temperature is about room temperature (RT).

Clause 124. The alginate microsphere of any one of clauses 115-123, wherein the alginate microsphere is reconstituted in saline or saline-radiopaque contrast at physiological pH.

Clause 125. A method of preparing a photopolymerized, alginate microsphere capable of self-degradation upon rehydration, the method comprising:

forming droplets from a precursor solution, the precursor solution comprising: an alginate lyase enzyme pre-treated by varying temperature, by varying pH, and/or with a metal-ion enzyme inhibitor; alginate molecules functionalized with an ethylenically unsaturated functional group, the molecules having one or both of (a) a predetermined molecular weight, and (b) a predetermined ratio of β-D-Mannuronic acid (M) blocks to α-L-Guluronic acid (G) blocks; and a photoinitiator;

irradiating the droplets including the photoinitiator, thereby crosslinking the alginate molecules to form a photopolymerized, alginate microsphere; and dehydrating, and optionally sterilizing, the alginate microsphere thereby substantially removing water from the microsphere.

Clause 126. The method of clause 125, wherein the ethylenically unsaturated functional group is selected from the group consisting of acrylate, methacrylate, vinylic, and allylic.

Clause 127. The method of clause 125 or 126, wherein the precursor solution comprises one or more cryoprotectants.

Clause 128. The method of any one of clauses 125-127, wherein the gelling bath comprises one or more cryoprotectants.

Clause 129. The method of clause 127 or 128, wherein the cryoprotectant is selected from the group consisting of hydroxypropyl-β cyclodextrin, trehalose, polyvinyl pyrrolidone of 40 kDa (PVP 40 kDa) and dextran (70 kDa molecular weight).

Clause 130. The method of clause 129, wherein the concentration of the trehalose in the precursor solution is about 0.1% w/v to about 20% w/v.

Clause 131. The method of clause 129 or 130, wherein the concentration of the Hydroxypropyl-0 cyclodextrin is about 0.1% w/v to about 2% w/v.

Clause 132. The method of any one of clauses 129-131, wherein the concentration of the PVP 40 kDa in the precursor solution is about 0.1% w/v to about 1% w/v.

Clause 133. The method of any one of clauses 129-132, wherein the concentration of the dextran (molecular weight 70 kDa) in the precursor solution is about 0.1% w/v to about 1% w/v.

Clause 134. The method of any one of clauses 128-133, wherein the precursor solution and the gelling bath comprise the same cryoprotectant.

Clause 135. The method of clause 134, wherein the precursor solution and the gelling bath comprise the same cryoprotectant at equal or about equal concentrations.

Clause 136. The method of any one of clauses 125-135, wherein the dehydrating comprises lyophilizing the alginate microsphere.

Clause 137. The method of clause 136, wherein a residual water content of the lyophilized alginate microsphere is in the range of about 1% to about 3% by mass.

Clause 138. The method of any one of clauses 125-137, wherein a sphericity of the alginate microsphere is at least about 0.7, at least about 0.75, at least about 0.8, at least about at least about 0.9, at least about 0.95, or at least about 0.99.

Clause 139. The method of any one of clauses 125-138, further comprising sterilizing the alginate microsphere or lyophilized alginate microsphere.

Clause 140. The method of clause 139, wherein the sterilizing comprises high energy radiation sterilization, gamma-ray sterilization, or e-beam sterilization.

Clause 141. The alginate microsphere of clause 140, wherein the sterilization comprises between about 15 and about 25 kGy of gamma radiation from Cobalt 60 Isotope, or about 25 kGy of electron beam radiation in accordance with ISO 11137-1:2006.

Clause 142. The method of any one of clause 125-141, further comprising storing the alginate microsphere for at least about 3 months, at least about 6 months, at least about 12 months, at least about 18 months, at least about 24 months, at least about 36 months, at least about 48 months, or at least about 60 months when stored at a given temperature.

Clause 143. The method of any one of clauses 125-142, wherein a shelf-life of the alginate microsphere is at least about 3 months, at least about 6 months, at least about 12 months, at least about 18 months, at least about 24 months, at least about 36 months, at least about 48 months, or at least about 60 months when stored at a given temperature.

Clause 144. The method of clause 142 or 143, wherein the given temperature is between about 2° C. and about 8° C.

Clause 145. The method of clause 142 or 143, wherein the given temperature is about room temperature (RT).

Clause 146. The method of any one of clauses 125-145, further comprising administering the alginate microsphere, the lyophilized alginate microsphere, or the sterilized microsphere to a subject.

Clause 147. The method of clause 146, wherein the step of administering the alginate microsphere, the lyophilized alginate microsphere, or the sterilized microsphere to a subject is preceded by reconstituting the alginate microsphere, the lyophilized alginate microsphere, or the sterilized microsphere using saline or saline-radiopaque contrast at physiological pH.

Clause 148. The method of any one of clauses 125-147, wherein flowing the precursor solution through the orifice to form droplets is performed using a method selected from the group consisting of drop casting, spray congealing/spray cooling, spray drying, and microfluidic droplet production.

Clause 149. The method of any one of clauses 125-148, wherein the degradation of alginate microsphere is controlled by one or more of the pre-treatment of the alginate lyase enzyme, the predetermined molecular weight of the alginate molecule, and the predetermined ratio of M:G blocks of the alginate molecules, and a composition of gelling bath, including an amount and or charge of one or more ions in the gelling bath.

Clause 150. The method of any one of clauses 125-149, wherein the pH of alginate lyase enzyme in the precursor solution containing alginate lyase and alginate, is in the range of pH 3.0 to 6.4, to prevent the degradation of alginate, before crosslinking with divalent metal cation.

Clause 151. The method of any one of clauses 125-150, wherein the metal-ion enzyme inhibitor is a reversible inhibitor selected from the group consisting of $Cu^{2+}$, $Zn^{2+}$, and $Fe^{3+}$ (e.g., to control the degradation of alginate in the precursor solution, before crosslinking with divalent metal cation).

Clause 152. The method of any one of clauses 125-151, wherein the temperature of the precursor solution is in the range of 1-4° C. to control the degradation of alginate, before crosslinking with divalent metal cation.

Clause 153. The method of any one of clauses 125-152, wherein the pre-treatment of the alginate enzyme in the precursor solution allow the mixing of the desired activity of enzyme (referred as units, U) with the alginate, which controls a degradation of the alginate microsphere for a length of time.

Clause 154. The method of any one of clauses 125-153, wherein the degradation of the alginate microsphere is controlled by the predetermined molecular weight of alginate molecules.

Clause 155. The method of any one of clauses 125-154, wherein the predetermined molecular weight of the alginate molecules is in a range of greater than about 100 kDa to less than about 800 kDa.

Clause 156. The method of any one of clauses 125-155, wherein the predetermined ratio of M:G block controls a degradation of alginate microsphere.

Clause 157. The method of any one of clauses 125-156, wherein the predetermined ratio of M:G blocks is about 50:50, about 55:45, about 60:40, about 65:35, about about 75:25, about 80:20, about 85:15, about 90:10, or about 95:5.

Clause 158. The method of clause 157, wherein the alginate microsphere degrades over a period of less than about 5 days.

Clause 159. The method of clause 157 or 158, wherein the alginate microsphere degrades over a period of greater than about 2 days.

Clause 160. The method of any one of clauses 125-156, wherein the predetermined ratio of M:G blocks is about 50:50, about 45:55, about 40:60, about 35:65, about about 25:75, about 20:80, about 15:85, about 10:90, or about 5:95.

Clause 161. The method of clause 160, wherein the alginate microsphere degrades over a period of between about 5 days and about 30 days.

Clause 162. The method of any one of clauses 125-161, wherein the pre-treated alginate lyase enzyme is mixed in the precursor solution having enzyme activity ranging from U/mg to 1 U/mg of alginate.

Clause 163. The method of any one of clauses 125-162, wherein the pre-treated alginate lyase enzyme is mixed in the precursor solution having enzyme activity ranging from U/mg to 0.250 U/mg of alginate.

Clause 164. The method of clause 163, wherein the alginate microsphere degrades over a period of less than about 5 days.

Clause 165. The method of any one of clauses 125-162, wherein the pre-treated alginate lyase enzyme is mixed in the precursor solution having enzyme activity ranging from U/mg to 0.125 U/mg of alginate.

Clause 166. The method of clause 165, wherein the alginate microsphere degrades over a period of between about 5 days and about 30 days.

Clause 167. The method of any one of clauses 124-147, the pre-treated alginate lyase enzyme is mixed in the precursor solution having enzyme activity ranging from 0.0025 U/mg to 0.005 U/mg of alginate.

Clause 168. The method of clause 167, wherein the alginate microsphere degrades over a period of greater than about 30 days.

Clause 169. The method of any one of clauses 125-168, wherein the precursor solution and/or the gelling bath further comprises a bioactive agent.

Clause 170. The method of clause 169, wherein the bioactive agent comprises an anti-inflammatory agent to alleviate pain associated with embolization in a subject.

Clause 171. The method of clause 170, wherein the anti-inflammatory agent comprises hyaluronic acid having a molecular weight of between about 1 million (M) and about M Daltons.

Clause 172. The method of clause 171, wherein the ratio of hyaluronic acid to the alginate molecules is about 1:20 by weight.

Clause 173. The method of any one of clauses 125-172, wherein a pH of the gelling bath is less than about 6.5.

Clause 174. The method of any one of clauses 125-172, wherein a pH of the gelling bath is equal to or about equal to a pH of the precursor solution.

Clause 175. The method of any one of clauses 125-174, wherein a temperature of the precursor solution is equal to or about equal to between 1° C. and about 4° C.

Clause 176. A method of inducing a self-degrading embolism in a subject in need thereof, comprising administering a plurality of the alginate microspheres of any one of clauses 1-36 and 89-124 into a blood vessel of the subject.

Clause 177. The method of clause 176, wherein the blood vessel is a *geniculate* artery.

Clause 178. A syringe, comprising:
a first chamber comprising alginate microspheres of any one of clauses 1-36 or 89-124;
a second chamber disposed axially to the first chamber, said second chamber comprising a reconstitution medium; and
a plunger configured to, upon depression, expose the alginate microspheres to the reconstitution medium, thereby reconstituting the alginate microspheres.

Clause 179. The syringe of clause 178, further comprising a breakable membrane separating the first chamber and the second chamber, wherein upon depression of the plunger, the breakable membrane breaks to expose the alginate microspheres to the reconstitution medium, thereby reconstituting the alginate microspheres.

Clause 180. A microsphere capable of self-degradation, upon rehydration, for administration to a mammalian subject in need thereof, the microsphere comprising:
a biocompatible polysaccharide material incapable of being enzymatically hydrolyzed by the mammalian subject, wherein the biocompatible polysaccharide material has one or both of (i) a predetermined molecular weight, and (ii) a predetermined ratio of β-D-Mannuronic acid (M) blocks to α-L-Guluronic acid (G) blocks;
an enzyme capable of hydrolyzing the biocompatible polysaccharide material, wherein the enzyme does not naturally occur in the mammalian subject, and wherein the enzyme is pre-treated by varying temperature, by varying pH, and/or with a metal-ion enzyme inhibitor; and
a divalent metal-ion crosslinking the biocompatible polysaccharide material,
wherein the microsphere is substantially free of water and/or sterilized.

Clause 181. The microsphere of clause 180, wherein the biocompatible polysaccharide material comprises alginate.

Clause 182. The microsphere of clause 180 or 181, wherein the enzyme comprises alginate lyase.

Clause 183. The microsphere of any one of clauses 180-182, wherein the biocompatible polysaccharide material is resorbable.

Clause 184. The microsphere of any one of clauses 180-183, wherein the biocompatible polysaccharide material is stable to enzymatic hydrolysis within the mammalian subject.

Clause 185. The microsphere of any one of clauses 180-184, wherein a rate of resorption of the biocompatible polysaccharide material is more precisely controlled by inclusion of a quantity of an enzyme not found within the mammal that has a specific action that causes breakdown of the embolic material once in the body.

Clause 186. A method of preparing a microsphere capable of self-degradation, upon rehydration, for administration to a mammalian subject in need thereof, the method comprising:
 forming droplets from a precursor solution, the precursor solution comprising: a biocompatible polysaccharide material incapable of being enzymatically hydrolyzed by the mammalian subject, wherein the biocompatible polysaccharide material has one or both of (i) a predetermined molecular weight, and (ii) a predetermined ratio of β-D-Mannuronic acid (M) blocks to α-L-Guluronic acid (G) blocks; and an enzyme capable of hydrolyzing the biocompatible polysaccharide material, wherein the enzyme does not naturally occur in the mammalian subject, and wherein the enzyme is pre-treated by varying temperature, by varying pH, and/or with a metal-ion enzyme inhibitor;
 contacting the droplets with a gelling bath comprising a cryoprotectant, and a divalent metal-ion, thereby cross-linking the biocompatible polysaccharide material to form a microsphere,
 dehydrating, and optionally sterilizing, the microsphere thereby substantially removing water from the microsphere.

Clause 187. The method of clause 186, wherein the biocompatible polysaccharide material comprises alginate.

Clause 188. The method of clause 186 or 187, wherein the enzyme comprises alginate lyase.

Clause 189. The method of any one of clauses 186-188, wherein the biocompatible polysaccharide material is resorbable.

Clause 190. The method of any one of clauses 186-189, wherein the biocompatible polysaccharide material is stable to enzymatic hydrolysis within the mammalian subject.

Clause 191. The method of any one of clauses 186-190, wherein a rate of resorption of the biocompatible polysaccharide material is more precisely controlled by inclusion of a quantity of an enzyme not found within the mammal that has a specific action that causes breakdown the embolic material once in the body.

Clause 192. A photopolymerized, microsphere capable of self-degradation, upon rehydration, for administration to a mammalian subject in need thereof, comprising:
 a biocompatible polysaccharide material incapable of being enzymatically hydrolyzed by the mammalian subject, wherein the biocompatible polysaccharide material has one or both of (i) a predetermined molecular weight, and (ii) a predetermined ratio of β-D-Mannuronic acid (M) blocks to α-L-Guluronic acid (G) blocks;
 an enzyme capable of hydrolyzing the biocompatible polysaccharide material, wherein the enzyme does not naturally occur in the mammalian subject, and wherein the enzyme is pre-treated by varying temperature, by varying pH, and/or with a metal-ion enzyme inhibitor; and
 a photoinitiator,
 wherein the biocompatible polysaccharide material is crosslinked by irradiating the photoinitiator, and
 wherein the microsphere is substantially free of water and/or sterilized.

Clause 193. The microsphere of clause 192, wherein the biocompatible polysaccharide material comprises alginate.

Clause 194. The microsphere of clause 192 or 193, wherein the enzyme comprises alginate lyase.

Clause 195. The microsphere of any one of clauses 192-194, wherein the biocompatible polysaccharide material is resorbable.

Clause 196. The microsphere of any one of clauses 192-195, wherein the biocompatible polysaccharide material is stable to enzymatic hydrolysis within the mammalian subject.

Clause 197. The microsphere of any one of clauses 192-196, wherein a rate of resorption of the biocompatible polysaccharide material is more precisely controlled by inclusion of a quantity of an enzyme not found within the mammal that has a specific action that causes breakdown of the embolic material once in the body.

Clause 198. A method of preparing a photopolymerized, microsphere capable of self-degradation, upon rehydration, for administration to a mammalian subject in need thereof, the method comprising:
 flowing a precursor solution through an orifice to form droplets, the precursor solution comprising: a biocompatible polysaccharide material incapable of being enzymatically hydrolyzed by the mammalian subject, wherein the biocompatible polysaccharide material has one or both of (i) a predetermined molecular weight, and (ii) a predetermined ratio of β-D-Mannuronic acid (M) blocks to α-L-Guluronic acid (G) blocks; an enzyme capable of hydrolyzing the biocompatible polysaccharide material, wherein the enzyme does not naturally occur in the mammalian subject, and wherein the enzyme is pre-treated by varying temperature, by varying pH, and/or with a metal-ion enzyme inhibitor; and a photoinitiator; and
 irradiating the droplets including the photoinitiator, thereby crosslinking the biocompatible polysaccharide material to form a photopolymerized, microsphere,
 dehydrating, and optionally sterilizing, the microsphere thereby substantially removing water from the microsphere.

Clause 199. The method of clause 198, wherein the biocompatible polysaccharide material comprises alginate.

Clause 200. The method of clause 198 or 199, wherein the enzyme comprises alginate lyase.

Clause 201. The method of any one of clauses 198-200, wherein the biocompatible polysaccharide material is resorbable.

Clause 202. The method of any one of clauses 198-201, wherein the biocompatible polysaccharide material is stable to enzymatic hydrolysis within the mammalian subject.

Clause 203. The method of any one of clauses 198-202, wherein the rate of resorption of the biocompatible polysaccharide material is more precisely controlled by inclusion of a quantity of an enzyme not found within the mammal that has a specific action that causes breakdown the embolic material once in the body.

Clause 300. A method of preparing an alginate microsphere capable of self-degradation upon rehydration, the method comprising:
 forming droplets from a precursor solution using a microfluidics platform, the precursor solution comprising:
 (i) an alginate lyase enzyme pre-treated by alkaline pH solution of varying range and varying temperature (1-4° C.);
 (ii) alginate molecules having one or both of (a) a predetermined molecular weight, and (b) a predetermined ratio of β-D-Mannuronic acid (M) blocks to α-L-Guluronic acid (G) blocks;
 (iii) crosslinking agent such as Ca-EDTA or CaCO$_3$ and;
 (iv) excipients contacting the droplets with a gelling solution comprising of surfactant, oil, acetic acid, thereby cross-linking the alginate molecules to form an alginate microsphere; and dehydrating, and optionally sterilizing, the alginate microsphere thereby substantially removing water from the microsphere.

Clause 301. An alginate microsphere made by the method of clause 300.

Clause 302. The alginate microsphere of claim 301, wherein the degradation of alginate microsphere is controlled by one or more of the pre-treatment of the alginate lyase enzyme, amount of the alginate enzyme in the microsphere, the predetermined molecular weight of the alginate molecule, and the predetermined ratio of M:G blocks of the alginate molecules, and bivalent cation-crosslinking.

Clause 303. The alginate microsphere of clause 302, wherein the pH of precursor solution containing Alginate, alginate lyase and crosslinking agent (Ca-EDTA or $CaCO_3$) is the range of 8 to 13 at temperature 1-4° C. to prevent the degradation of alginate as well as the gelation of precursor solution.

Clause 304. The alginate microsphere of any one of clauses 301-303, wherein the pre-treatment of the alginate enzyme in the precursor solution allows mixing of a predetermined amount of enzyme (measured in units, U) with the alginate molecules.

Clause 305. The alginate microsphere any one of clauses 301-304, wherein after the droplet of the precursor solution have alkaline pH and low temperature can be generation through microfluidics chip and crosslinked in a solution containing acetic acidic in the range 0.05% v/v to 5% v/v, oil and surfactant for a duration of 1 min to 3 hours. Under acidic condition, the crosslinking of alginate with $Ca^{2+}$ ion occur due to the ionization of Ca-EDTA or $CaCO_3$ and the encapsulated enzyme remains inactive under acidic pH condition, thus preventing the degradation of alginate beads.

Clause 306. The alginate microsphere any one of clauses 301-305, wherein the $Ca^{2+}$-crosslinked alginate beads containing alginate lyase can be further crosslinked with bivalent $Ca^{2+}$ cation by exposing beads to <10% w/v of calcium chloride for a duration of >1 mins to <24 hours. The duration of crosslinking period controls the degradation of alginate particles under physiological conditions.

Clause 307. The alginate microsphere of clause 306, wherein the calcium chloride solution further contains excipients required for the freeze-drying steps.

Clause 308. The alginate microsphere of clause 307, where in the $Ca^{2+}$-crosslinked alginate beads containing alginate lyase are further washed in aqueous medium containing excipients to remove unbound $Ca^{2+}$ ion.

Clause 309. The alginate microsphere of clause 308, wherein the $Ca^{2+}$-crosslinked alginate beads containing alginate lyase are dispersed in a solution containing excipients and subjected to freeze drying to produce freeze dried $Ca^{2+}$ crosslinked alginate beads containing alginate lyase enzyme.

Clause 310. The alginate microsphere of clause 309, wherein the freeze dried $Ca^{2+}$ crosslinked alginate beads containing alginate lyase enzyme are further subjected to sterilization step (gamma-radiation and e-beam radiation).

Clause 311. The alginate microsphere of clause 310, wherein the freeze dried and sterilized $Ca^{2+}$-crosslinked alginate beads containing alginate lyase enzyme can be reconstituted in aqueous solution of neutral pH which activates the alginate lyase enzyme and initiates the degradation of alginate particles.

Clause 401. An alginate microsphere capable of self-degradation upon rehydration, comprising:

an alginate lyase enzyme pre-treated by varying temperature, by varying pH, and/or with a metal-ion enzyme inhibitor;

alginate molecules having one or both of (i) a predetermined molecular weight, and (ii) a predetermined ratio of β-D-Mannuronic acid (M) blocks to α-L-Guluronic acid (G) blocks; and a divalent metal-ion crosslinking the alginate molecules, wherein the alginate microsphere is substantially free of water and/or sterilized.

Clause 402. The alginate microsphere of clause 401, wherein the degradation of alginate microsphere is controlled by one or more of the pre-treatment of the alginate lyase enzyme, an amount of the alginate enzyme in the microsphere, the predetermined molecular weight of the alginate molecule, and the predetermined ratio of M:G blocks of the alginate molecules, and a composition of gelling bath, including an amount and or charge of one or more ions in the gelling bath.

Clause 403. The alginate microsphere of clause 401, wherein at least one of (i)-(iii) applies:

(i) the metal-ion enzyme inhibitor is a reversible inhibitor selected from the group consisting of $Cu^{2+}$, $Zn^{2+}$, and $Fe^{2+}$, (ii) the pre-treatment of the alginate enzyme in the precursor solution allows mixing of a predetermined amount of enzyme (measured in units, U) with the alginate molecules, and (iii) an activity of the alginate lyase enzyme is modulated by adjusting one or more of a pH of a gelling bath, a temperature of the gelling bath, and an amount of the metal-ion enzyme inhibitor in the alginate microsphere.

Clause 404. The alginate microsphere of clause 401, wherein at least one of (i)-(v) applies:

(i) the predetermined molecular weight of the alginate molecules is in a range of greater than about 100 kDa to less than about 800 kDa, (ii) the predetermined ratio of M:G blocks is about 50:50, about 55:45, about 60:40, about 65:35, about 70:30, about 75:25, about 80:20, about 85:15, about 90:10, or about 95:5, (iii) the predetermined ratio of M:G blocks is about 50:50, about 45:55, about 40:60, about 35:65, about 30:70, about 25:75, about 20:80, about 15:85, about 10:90, or about 5:95, (iv) an activity of the alginate lyase enzyme is between about 0.05 mU (milliunits) and about 2.5 mU per microsphere, and (v) an activity of the alginate lyase enzyme is between about 0.05 nU (nanounits) and about 0.05 mU per microsphere.

Clause 405. The alginate microsphere of clause 404, wherein at least one of (a)-(d) applies:

(a) the alginate microsphere of (ii) degrades over a period of less than about 5 days or greater than about 2 days, (b) the alginate microsphere of (iii) degrades over a period of between about 5 days and about 30 days, (c) the alginate microsphere of (iv) degrades over a period of less than about 5 days, and (d) the alginate microsphere of (v) degrades over a period of between about 5 days and about 30 days.

Clause 406. The alginate microsphere of clause 401, wherein at least one of (i)-(vii) applies:
  (i) the microsphere further comprises a bioactive agent,
  (ii) the microsphere further comprises a cryoprotectant selected from the group consisting of hydroxypropyl-β cyclodextrin, trehalose, polyvinyl pyrrolidone of 40 kDa (PVP 40 kDa), dextran (70 kDa molecular weight), glucose, lactose, maltodextrins, mannitol, glycols, and polyglycols,
  (iii) the alginate microsphere is lyophilized,
  (iv) a sphericity of the alginate microsphere is at least about 0.7, at least about 0.75, at least about 0.8, at least about 0.85, at least about 0.9, at least about 0.95, or at least about 0.99,
  (v) the alginate microsphere is sterilized, or the alginate microsphere is lyophilized and sterilized,
  (vi) a shelf-life of the alginate microsphere is at least about 3 months, at least about 6 months, at least about 12 months, at least about 18 months, at least about 24 months, at least about 36 months, at least about 48 months, or at least about 60 months when stored at a given temperature, and
  (vii) a lyophilized alginate microsphere is reconstituted in saline or saline-radiopaque contrast at physiological pH.

Clause 407. The alginate microsphere of clause 406, wherein at least one of (a)-(d) applies:
  (a) the bioactive agent of (i) comprises an anti-inflammatory agent, an anesthetic drug, an anti-cancer agent, or an anti-angiogenic agent,
  (b) a residual water content of the lyophilized alginate microsphere of (iii) is in the range of about 1% to about 3% by mass,
  (c) the sterilization of (v) comprises high energy radiation sterilization, gamma-ray sterilization, or e-beam sterilization, and
  (d) the given temperature of (vi) is between about 2° C. and about 8° C. or about room temperature (RT).

Clause 408. The alginate microsphere of clause 407, wherein the anti-inflammatory agent of (a) comprises hyaluronic acid having a molecular weight of between about 1 million (M) and about 5 M Daltons or the sterilization of (c) comprises between about 15 and about 25 kGy of gamma radiation from Cobalt 60 Isotope, or about 25 kGy of electron beam radiation in accordance with ISO 11137-1: 2006.

Clause 409. A method of preparing an alginate microsphere capable of self-degradation upon rehydration, the method comprising:
  forming droplets from a precursor solution, the precursor solution comprising:
    an alginate lyase enzyme pre-treated by varying temperature, by varying pH, and/or with a metal-ion enzyme inhibitor; and
    alginate molecules having one or both of (a) a predetermined molecular weight, and (b) a predetermined ratio of β-D-Mannuronic acid (M) blocks to α-L-Guluronic acid (G) blocks;
  contacting the droplets with a gelling bath comprising a divalent metal-ion, thereby crosslinking the alginate molecules to form an alginate microsphere; and
  dehydrating, and optionally sterilizing, the alginate microsphere thereby substantially removing water from the microsphere.

Clause 410. The method of clause 409, wherein at least one of (i)-(x) applies:
  (i) the precursor solution comprises one or more cryoprotectants,
  (ii) the gelling bath comprises one or more cryoprotectants,
  (iii) the pH of alginate lyase enzyme in the precursor solution containing alginate lyase and alginate is in the range of pH 3.0 to 6.4,
  (iv) the metal-ion enzyme inhibitor is a reversible inhibitor selected from the group consisting of $Cu^{2+}$, $Zn^{2+}$, and $Fe^{2+}$,
  (v) the temperature of the precursor solution is in the range of 1-4° C.,
  (vi) the pre-treatment of the alginate enzyme in the precursor solution allows mixing of a predetermined amount of enzyme (measured in units, U) with the alginate molecules,
  (vii) an activity of the alginate lyase enzyme is modulated by adjusting one or more of a pH of the gelling bath, a temperature of the gelling bath, and an amount of the metal-ion enzyme inhibitor in the alginate microsphere,
  (viii) a pH of the gelling bath is less than about 6.5,
  (ix) a pH of the gelling bath is equal to or about equal to a pH of the precursor solution, and
  (x) the precursor solution and/or the gelling bath further comprises a bioactive agent.

Clause 411. The method of clause 409, wherein at least one of (i)-(iv) applies:
  (i) the dehydrating comprises lyophilizing the alginate microsphere,
  (ii) forming the droplets is performed using a method selected from the group consisting of drop casting, spray congealing/spray cooling, spray drying, microfluidic droplet production, and jet-cutting,
  (iii) a sphericity of the alginate microsphere is at least about 0.7, at least about 0.75, at least about 0.8, at least about 0.85, at least about 0.9, at least about 0.95, or at least about 0.99, and
  (iv) a shelf-life of the alginate microsphere is at least about 3 months, at least about 6 months, at least about 12 months, at least about 18 months, at least about 24 months, at least about 36 months, at least about 48 months, or at least about 60 months when stored at a given temperature.

Clause 412. The method of clause 410, wherein the cryoprotectant of (i) and (ii) is each independently selected from the group consisting of hydroxypropyl-β cyclodextrin, trehalose, polyvinyl pyrrolidone of 40 kDa (PVP 40 kDa), dextran (70 kDa molecular weight), glucose, lactose, maltodextrins, mannitol, glycols, and polyglycols.

Clause 413. The method of clause 412, wherein at least one of (a)-(f) applies:
  (a) the concentration of the trehalose in the precursor solution (i) is about 0.1% w/v to about 20% w/v,
  (b) the concentration of the hydroxypropyl-β cyclodextrin the precursor solution (i) or the gelling bath (ii) is about 0.1% w/v to about 2% w/v,
  (c) the concentration of the PVP 40 kDa in the precursor solution (i) is about 0.1% w/v to about 1% w/v,
  (d) the concentration of the dextran (molecular weight 70 kDa) in the precursor solution (i) is about 0.1% w/v to about 1% w/v,
  (e) the precursor solution (i) and the gelling bath (ii) comprise the same cryoprotectant, and
  (f) the precursor solution (i) and the gelling bath (ii) comprise the same cryoprotectant at equal or about equal concentrations.

Clause 414. The method of clause 411, wherein a residual water content of the lyophilized alginate microsphere is in the range of about 1% to about 3% by mass.

Clause 415. The method of clause 409, further comprising at least one step selected from (i)-(iv)
- (i) sterilizing the alginate microsphere or the alginate microsphere that has been dehydrated by lyophilization,
- (ii) storing the alginate microsphere for at least about 3 months, at least about 6 months, at least about 12 months, at least about 18 months, at least about 24 months, at least about 36 months, at least about 48 months, or at least about 60 months when stored at a given temperature,
- (iii) administering the alginate microsphere, or the alginate microsphere that has been dehydrated by lyophilization, to a subject, and
- (iv) reconstituting the alginate microsphere, or the alginate microsphere that has been dehydrated by lyophilization, using saline or saline-radiopaque contrast at physiological pH.

Clause 416. The method of clause 415, wherein at least one of (a)-(d) applies:
- (a) the sterilizing of (i) comprises high energy radiation sterilization, gamma-ray sterilization, or e-beam sterilization,
- (b) the sterilizing of (i) comprises between about 15 and about 25 kGy of gamma radiation from Cobalt 60 Isotope, or about 25 kGy of electron beam radiation in accordance with ISO 11137-1:2006,
- (c) the given temperature of (ii) is between about 2° C. and about 8° C., and
- (d) the given temperature of (ii) is about room temperature (RT).

Clause 417. The method of clause 409, wherein the degradation of alginate microsphere is controlled by one or more of the pre-treatment of the alginate lyase enzyme, an amount of the alginate enzyme in the microsphere, the predetermined molecular weight of the alginate molecule, and the predetermined ratio of M:G blocks of the alginate molecules, and a composition of gelling bath, including an amount and or charge of one or more ions in the gelling bath.

Clause 418. The method of clause 409, wherein at least one of (i)-(vii) applies:
- (i) the predetermined molecular weight of the alginate molecules is in a range of greater than about 100 kDa to less than about 800 kDa,
- (ii) the predetermined ratio of M:G blocks is about 50:50, about 55:45, about 60:40, about 65:35, about 70:30, about 75:25, about 80:20, about 85:15, about 90:10, or about 95:5,
- (iii) the predetermined ratio of M:G blocks is about 50:50, about 45:55, about 40:60, about 35:65, about 30:70, about 25:75, about 20:80, about 15:85, about 10:90, or about 5:95,
- (iv) the pre-treated alginate lyase enzyme is mixed in the precursor solution having enzyme activity ranging from 0.0025 U/mg to 1 U/mg of alginate,
- (v) the pre-treated alginate lyase enzyme is mixed in the precursor solution having enzyme activity ranging from 0.125 U/mg to 0.250 U/mg of alginate,
- (vi) the pre-treated alginate lyase enzyme is mixed in the precursor solution having enzyme activity ranging from 0.025 U/mg to 0.125 U/mg of alginate, and
- (vii) the pre-treated alginate lyase enzyme is mixed in the precursor solution having enzyme activity ranging from 0.0025 U/mg to 0.005 U/mg of alginate.

Clause 419. The method of clause 418, wherein at least one of (a)-(e) applies:
- (a) the alginate microsphere degrades over a period of less than about 5 days or greater than about 2 days,
- (b) the alginate microsphere of (iii) degrades over a period of between about 5 days and about 30 days,
- (c) the alginate microsphere of (v) degrades over a period of less than about 5 days,
- (d) the alginate microsphere of (vi) degrades over a period of between about 5 days and about 30 days, and
- (e) the alginate microsphere of (vii) degrades over a period of greater than about 30 days.

Clause 420. The method of clause 410, wherein the bioactive agent of (x) comprises an anti-inflammatory agent, an anesthetic agent, anti-cancer agent, or an anti-angiogenic agent.

Clause 421. The method of clause 420, wherein the anti-inflammatory agent comprises hyaluronic acid having a molecular weight of between about 1 million (M) and about 5 M Daltons.

Clause 509. A method of preparing an alginate microsphere capable of self-degradation upon rehydration, the method comprising:
forming droplets from a precursor solution using a microfluidics platform, the precursor solution comprising:
- (i) an alginate lyase enzyme pre-treated with an alkaline pH and with a temperature less than about 15° C.;
- (ii) alginate molecules having one or both of (a) a predetermined molecular weight, and (b) a predetermined ratio of β-D-Mannuronic acid (M) blocks to α-L-Guluronic acid (G) blocks; and
- (iii) a bivalent cation crosslinking agent;

contacting the droplets with a gelling solution comprising oil and an acid, thereby crosslinking the alginate molecules to form an alginate microsphere; and dehydrating, and optionally sterilizing, the alginate microsphere thereby substantially removing water from the microsphere.

Clause 510. The method of clause 509, wherein the degradation of alginate microsphere is controlled by one or more of the pre-treatment of the alginate lyase enzyme, an amount of the alginate enzyme in the microsphere, the predetermined molecular weight of the alginate molecule, and the predetermined ratio of M:G blocks of the alginate molecules, and bivalent cation crosslinking of the alginate molecules.

Clause 511. The method of clause 509 or 510, wherein at least one of (i)-(viii) applies:
- (i) the alginate lyase enzyme is pre-treated with a pH of about 8 to about 13,
- (ii) the alginate lyase enzyme is pre-treated with a temperature of about 1° C. to about 4° C.,
- (iii) the pre-treatment of the alginate enzyme in the precursor solution allows mixing of a predetermined amount of enzyme (measured in units, U) with the alginate molecules,
- (iv) the precursor solution has a pH of about 8 to about 13 and is maintained at a temperature of about 1° C. to about 4° C.,
- (v) the precursor solution further comprises an excipient,
- (vi) the bivalent cation crosslinking agent is $Ca^{2+}$ released from Ca-EDTA or $CaCO_3$,
- (vii) the acid is acetic acid, and
- (viii) the gelling solution further comprises a surfactant.

Clause 512. The method of any one of clauses 509-511, wherein the gelling solution comprises oil, about 0.05% v/v to about 5% v/v acetic acid, and a surfactant and the droplets are contacted with the gelling solution for about 1 minute to about 3 hours, crosslinking the alginate molecules.

Clause 513. The method of any one of clauses 509-512, wherein the step of dehydrating, and optionally sterilizing, the alginate microsphere is preceded by crosslinking the alginate microspheres with a bivalent $Ca^{2+}$ ion.

Clause 514. The method of any one of clauses 509-512, wherein the step of dehydrating, and optionally sterilizing, the alginate microsphere is preceded by further crosslinking the alginate molecules with a second bivalent $Ca^{2+}$ ion.

Clause 515. The method of clause 514, wherein further crosslinking the alginate molecules with a second bivalent $Ca^{2+}$ ion forms alginate microspheres crosslinked with a bivalent $Ca^{2+}$ ion.

Clause 516. The method of clause 513 or 514, wherein the alginate microspheres or alginate molecules are crosslinked by exposure to a solution comprising less than about 10% w/v $CaCl_2$ for about 1 minute to about 24 hours.

Clause 517. The method of clause 516, wherein the solution further comprises an excipient.

Clause 518. The method of clause 517, wherein the step of dehydrating the alginate microsphere or the bivalent $Ca^{2+}$ crosslinked alginate microspheres comprises lyophilizing the alginate microspheres or the bivalent $Ca^{2+}$ crosslinked alginate microspheres.

Clause 519. The method of clause 518, comprising sterilizing the lyophilized alginate microsphere or the lyophilized bivalent $Ca^{2+}$ crosslinked alginate microspheres using gamma radiation and/or e-beam radiation.

Clause 520. The method of clause 519, comprising reconstituting the lyophilized and sterilized alginate microspheres or the lyophilized and sterilized bivalent $Ca^{2+}$ crosslinked alginate microspheres in an aqueous solution of neutral pH.

EXAMPLES

Example 1: Alginate Lyase Enzyme Concertation Dependent Degradation of Alginate Particles The schematic diagram for the preparation of the alginate particles is shown in FIGS. 1A-1C and FIGS. 2A-2C. Sodium alginate of viscosity (5-40 cP, condition 1% w/v in water @ ° C.) was dissolved in de-ionized water to prepare the stock solution of concentration 4% w/v. Likewise, a stock solution of alginate lyase enzyme of concentration 50 U/ml was prepared by dissolving 5 mg of enzyme powder (equivalent 50 U) in 1 ml of DI water. To prepare the alginate lyase-sodium alginate precursor solution having final concentrations of 5 U/ml or 0.5 U/ml of alginate lyase enzyme and 2% w/v of sodium alginate, 0.1 ml or 0.01 ml of alginate lyase enzyme was mixed with 0.5 ml of 4% w/v of sodium alginate for 30 seconds and make up the volume to 1 ml with deionized water.

Figure 3A:
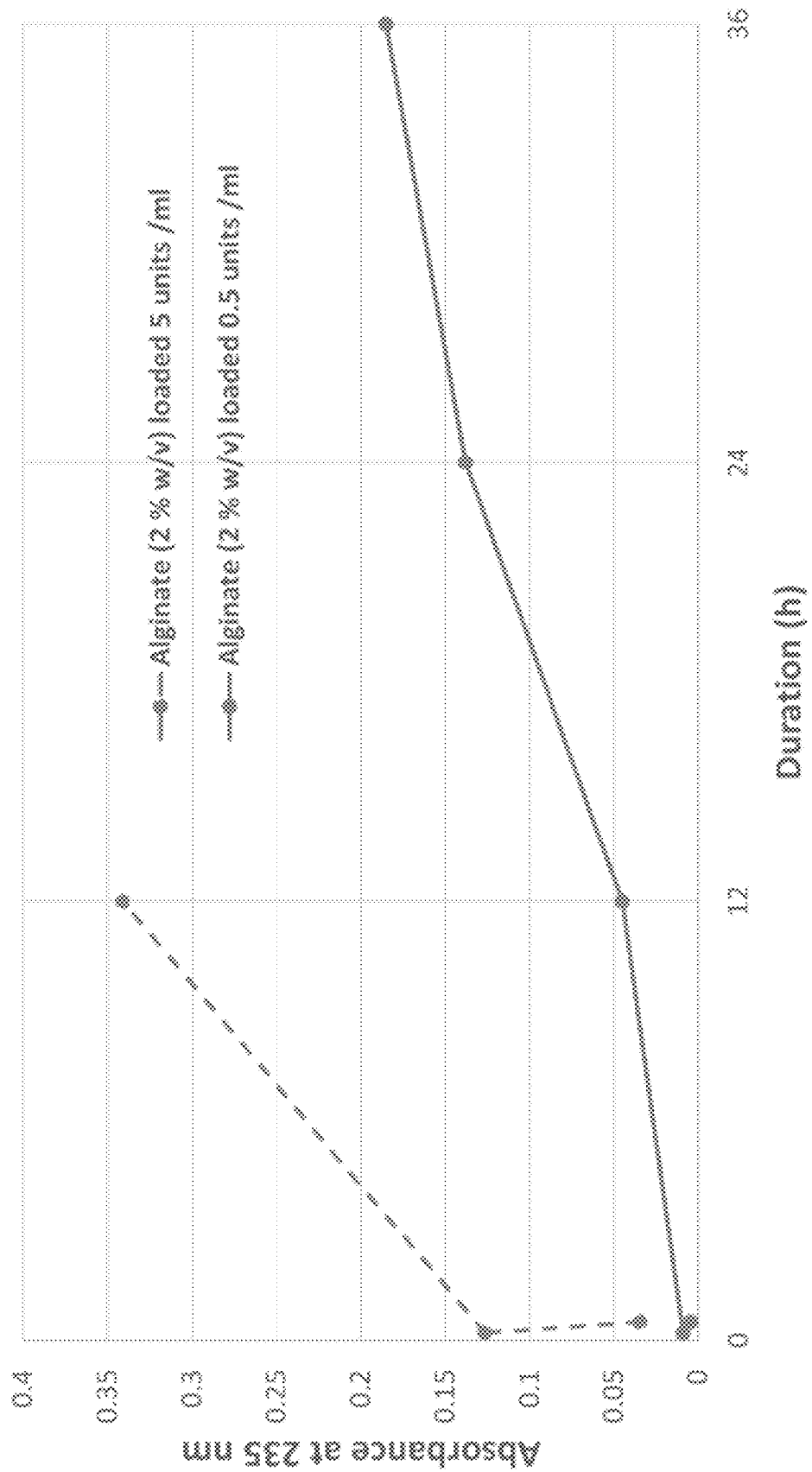
FIG. 3A illustrates enzyme concentration dependent alginate particle degradation. A line graph of the degradation of alginate particles over time with varying enzyme concentrations is provided.
Figure 3B:
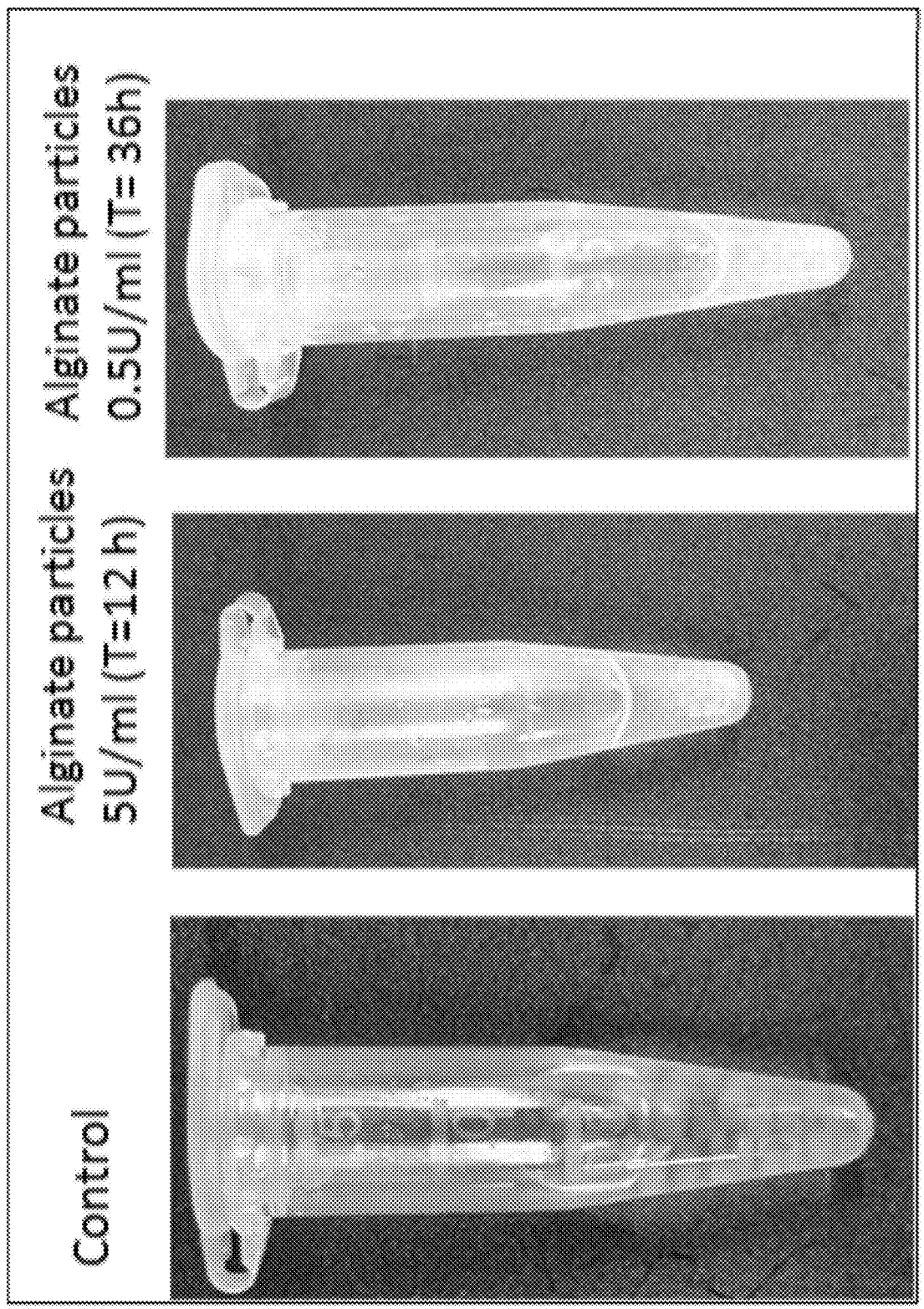
FIG. 3B illustrates enzyme concentration dependent alginate particle degradation. Images of the particles after the degradation period, and samples having varying concentrations of enzyme.
Figure 5:
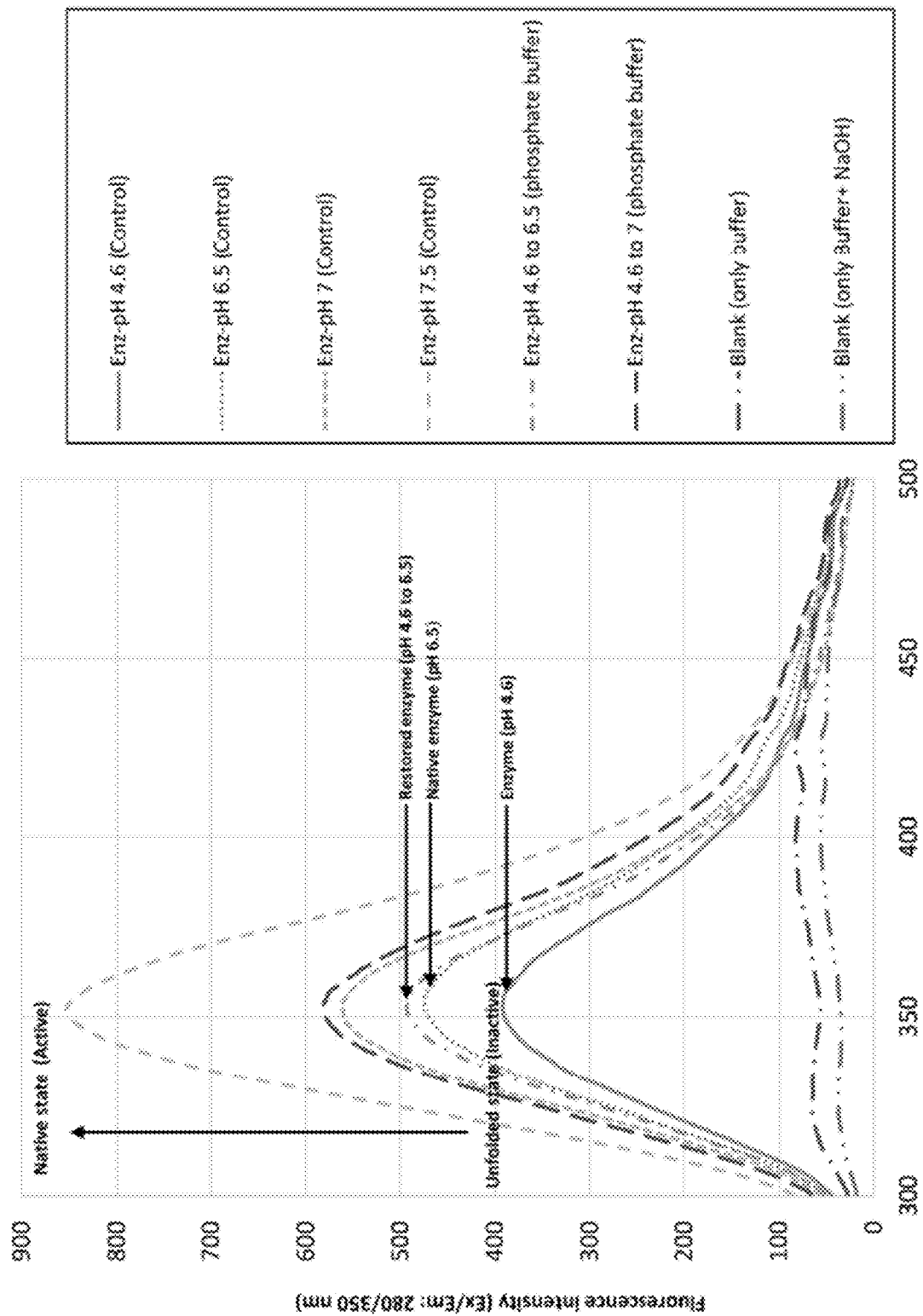
FIG. 5 illustrates pH dependent regulation of enzyme conformation/activity.

The precursor alginate lyase-alginate solution was added dropwise into the gelling bath containing 10% w/v calcium chloride under constant stirring for 5 minutes to achieve alginate lyase loaded $Ca^{2+}$-complexed alginate particles. Then, the particles were isolated by sieving or centrifugation and washed with de-ionized water three times for 1 minute each to remove excess or calcium chloride. Washed alginate lyase loaded with $Ca^{2+}$-crosslinked alginate particles were dispersed in 10 mM phosphate buffer at pH 6.8 and incubated at 37° C. for the desired duration to evaluate the degradation of alginate particles. The degradation of calcium ion complexed alginate particles loaded with 5 units (U) and 0.5 U of alginate lyase enzyme shown in FIG. 3A. The alginate particles loaded with 5 U of enzyme rapidly degraded in 12 h, whereas the particle loaded with 0.5 U of enzyme degraded at a slower rate and unable to reach the absorbance level similar to 5 U loaded alginate particle after 36 hours. From FIG. 3B, 5 U loaded alginate lyase loaded alginate particles were completely degraded in 12 h, whereas 0.5 U alginate lyase loaded alginate particles samples showed the partially degraded particles in 36 h. In the control sample (without enzyme), the calcium ion complexed alginate particles remained intact. These results demonstrated the alginate lyase enzyme concertation dependent degradation of alginate particles.

Example 2: Alginate Lyase Enzyme Concentration-Dependent Degradation of Alginate Particles Prepared from High Viscosity Alginate High viscosity sodium alginate (Viscosity 144 cP, condition 1% w/v in water @ 25° C.) was dissolved in de-ionized water to prepare the stock solution of concentration 3% w/v. Likewise, a stock solution of alginate lyase enzyme of concentration 50 U/ml was prepared by dissolving 5 mg of enzyme powder (equivalent 50 U) in 1 ml of DI water. To prepare the alginate lyase-sodium alginate precursor solution having final concentrations of 1 U/ml, 0.5 U/ml and 0.25 U/ml of alginate lyase enzyme and 2% w/v of sodium alginate, 0.02 ml, 0.01 ml, 0.005 ml) of alginate lyase enzyme was mixed with 0.5 ml of 3% w/v of sodium alginate for 30 seconds and make up the volume to 1 ml with de-ionized water.

Figure 4:
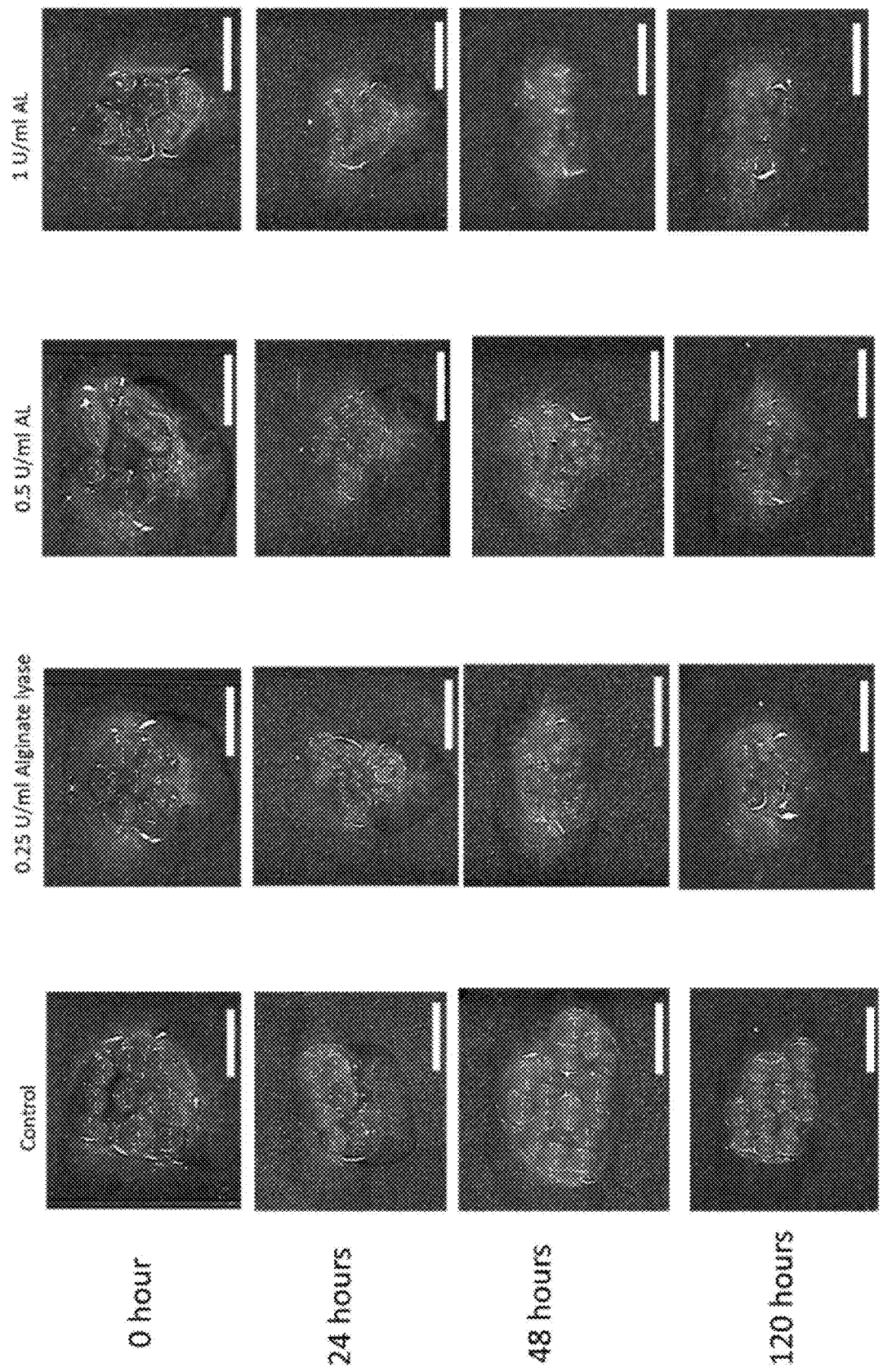
FIG. 4 illustrates enzyme concentration dependent degradation of $Ca^{2+}$-crosslinked alginate microspheres prepared from alginate (Viscosity 144 cps@ 1% w/v of alginate, 25° C.). Alginate lyase precursor solution containing 0.25 U/ml, 0.5 U/ml and 1 U/ml of alginate lyase and 1.5% w/v of alginate. The control microspheres do not contain enzyme. Scale bar=5 mm.

The precursor alginate lyase-alginate solution was added dropwise into the gelling bath containing 2% w/v calcium chloride under constant stirring for 5 minutes to achieve alginate lyase loaded $Ca^{2+}$-complexed alginate particles. Then, the particles were isolated by sieving or centrifugation and washed with de-ionized water three times for 1 minute each to remove excess or calcium chloride. Washed alginate lyase loaded $Ca^{2+}$-complexed alginate particles were dispersed in 10 mM phosphate buffer at pH 6.5 and incubated at 37° C. for the desired duration to evaluate the degradation of alginate particles. The degradation of calcium ion complexed alginate particles loaded with 1 U, 0.5 U and 0.25 U of alginate lyase enzyme shown in FIG. 4. The alginate particles loaded with 1 U of enzyme rapidly degraded over 120 hours when compared to the particle loaded with 0.5 U and 0.25 U of enzyme. In the control sample (without enzyme), the $Ca^{2+}$-crosslinked alginate particles remained intact. These results demonstrated the alginate lyase enzyme concertation dependent degradation of alginate particles.

Example 3: pH-Dependent Regulation of Alginate Lyase Enzyme Conformation/Activity To study, the pH-dependent regulation of lyase enzyme conformation/activity, the alginate lyase enzyme was exposed to different pH and subjected to the fluorescence spectroscopy. In general, an open conformation of enzyme inactivates or reduces the enzyme catalytic activity, whereas further stabilization of the native structure improves the catalytic activity of the enzyme. From FIG. 5, the fluorescence of native enzyme (1 U/ml) in acidic pH 4.6 (acetate buffer) is at a lower level when compared to the native enzyme at pH 7.0 (10 mM, phosphate buffer). The reduction in fluorescence in acidic pH indicated the open conformation of the enzyme. When the pH of enzyme solution changed to pH 4.6 to 7.0, the fluorescence recovered or enhanced is found to be at a level similar to the native enzyme at pH 7.0.

This demonstrated the reversible conformation of the alginate lyase enzyme in response to change in the pH of the solution with reactivation of enzyme activity. Therefore, by changing the pH of alginate lyase-alginate precursor or the gelling bath solutions, the initial degradation of particles during the manufacturing process of alginate lyase loaded divalent metal ion particles. On reconstituting the alginate-lyase enzyme loaded divalent metal ion complexed alginate particles in an aqueous solution having neutral pH (6.5 to 7.5), the activity of the alginate lyase enzyme can be restored to get the tailored degradation of the alginate particles.

Figure 6:
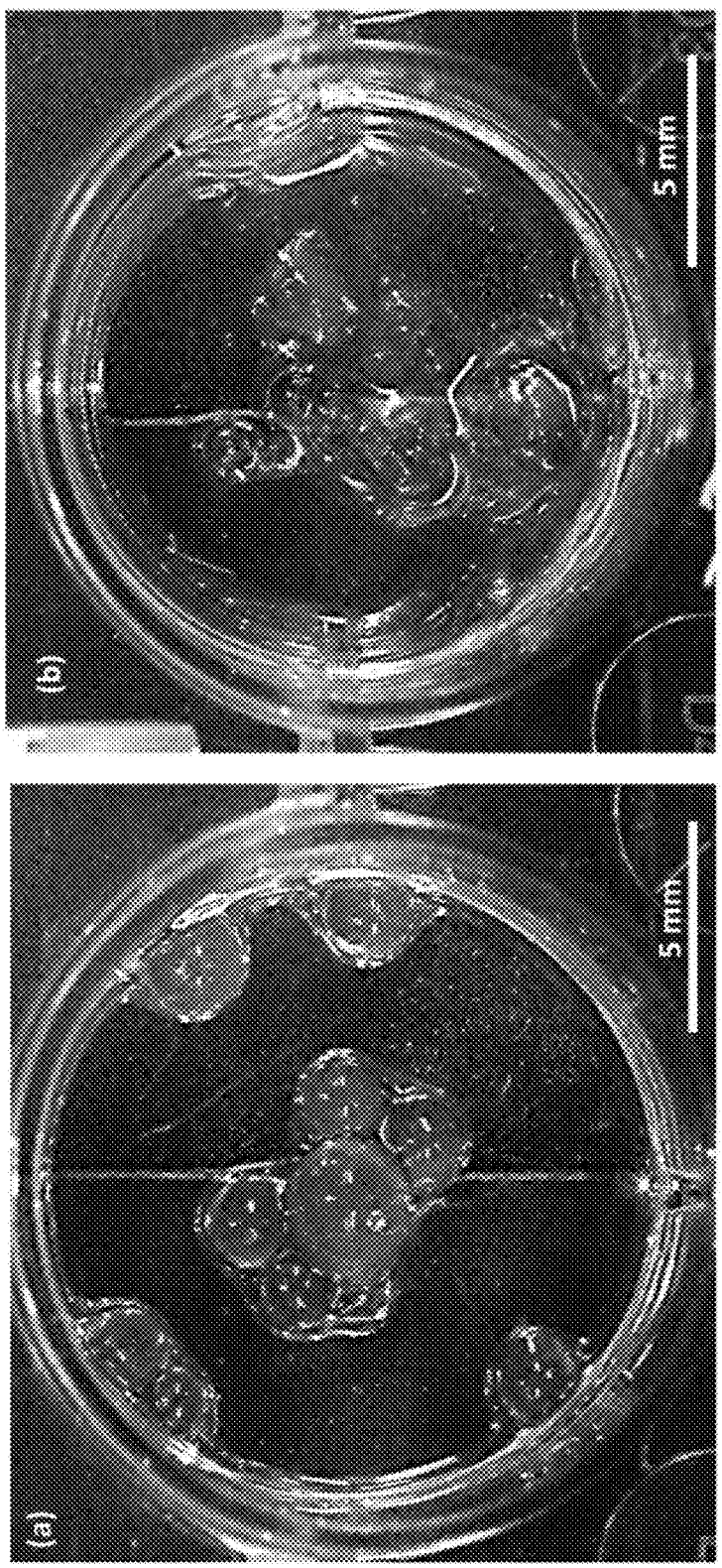
FIG. 6 illustrates preparation of $Ca^{2+}$-crosslinked alginate microspheres loaded with 5 U of alginate lyase enzyme using alginate lyase-alginate precursor solution pre-treated with (a) 0.1 M acetate buffer, pH 4.0 and (b) 0.01 M phosphate buffer, pH 6.5.

Example 4: Effect of pH on the Preparation of $Ca^{2+}$-Crosslinked Alginate Microspheres Loaded Alginate Lyase Enzyme Alginate lyase enzyme and high viscosity alginate (viscosity 144 cP, condition 1% w/v in water @ 25° C.) were dissolved in 0.1 M sodium acetate buffer of pH 4 with final concentrations of 5 U/ml and 1.5% w/v respectively. Similarly, alginate lyase enzyme-high viscosity alginate (viscosity 144 cps, condition 1% w/v in water @ 25° C.) solution was also prepared in 0.01 M phosphate buffer of pH 6.5 with final concentrations of 5 U/ml and 1.5% w/v respectively. Both the solutions were incubated at 4° C. for 15 mins, before dropping into 2% w/v calcium chloride solution to get calcium ion-crosslinked alginate microspheres loaded with alginate lyase enzyme. The crosslinked microspheres were washed three times in deionized water for 1 min each. The microspheres prepared in the acetate buffer showed a spherical shape (FIG. 6 (a)). On the other hand, microspheres obtained from phosphate buffer were irregularly shaped and partially degraded (FIG. 6 (b)). These results indicate that the low pH reduced the catalytic activity of the enzyme and prevented degradation of alginate, thereby aiding in getting the spherical microspheres. This method of making microspheres increases the processing window which may help in upscaling the production of the alginate microspheres loaded with the alginate lyase enzyme.

Example 5: Degradation of $Ca^{2+}$-Crosslinked Alginate Lyase-Alginate Microspheres Prepared from Alginate-Alginate Lyase Precursor Solution Pretreated with Acidic pH (Acetate Buffer, pH 4)

Figure 7:
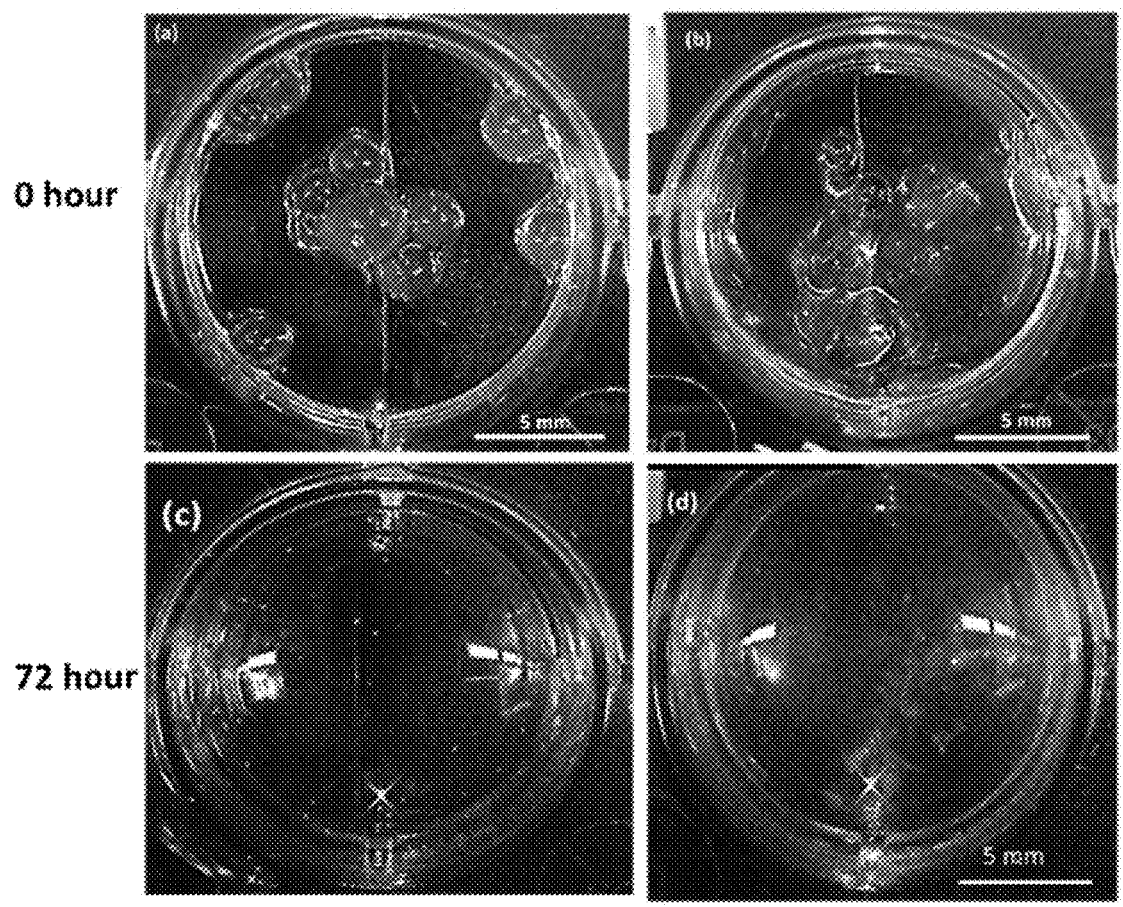
FIG. 7 illustrates microscopic images of degraded $Ca^{2+}$-crosslinked alginate microspheres prepared from alginate lyase (AL)-alginate (Alg) precursor solution containing 5 U of AL enzyme pre-treated with (a and c) 0.1 M acetate buffer, pH 4.0 and (b and d) 0.01 M phosphate buffer, pH 6.5, in phosphate buffer at 0 and 72 hours respectively. (e) Absorbance spectra of the degraded products of Alginate-AL microspheres corresponding to (c) and (d) samples.
Figure 7:
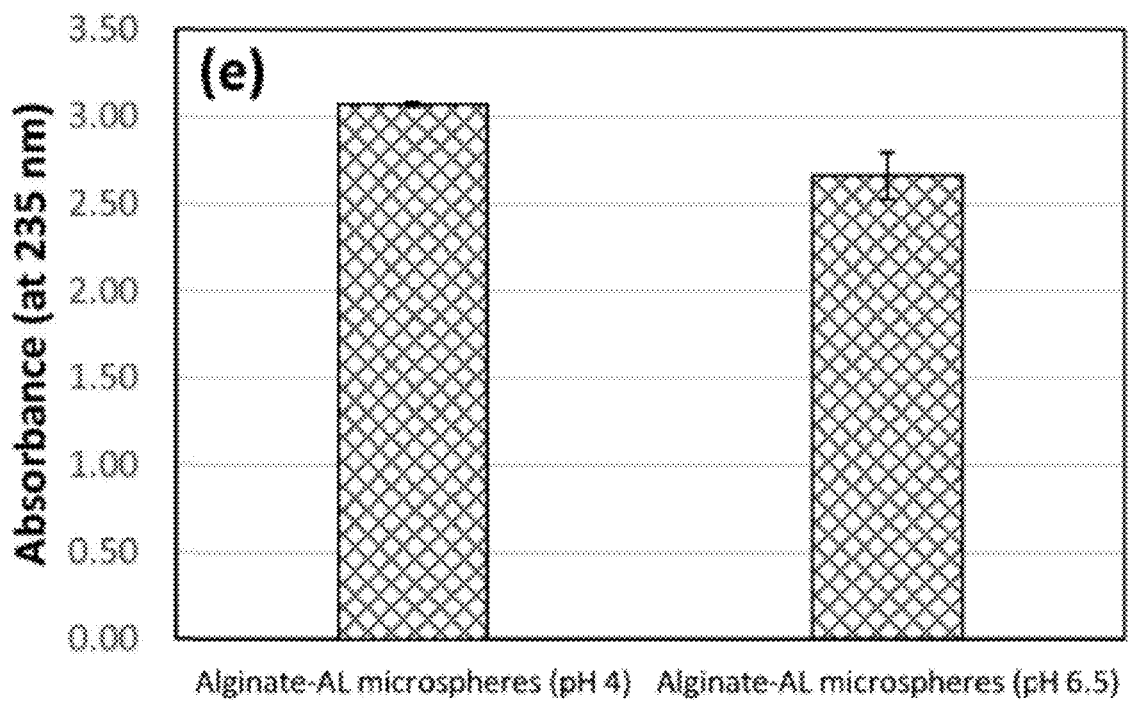

Alginate lyase enzyme and high viscosity alginate (viscosity 144 cP, condition 1% w/v in water @ 25° C.) were dissolved in 0.1 M sodium acetate buffer of pH 4 with final concentrations of 5 U/ml and 1.5% w/v respectively. Similarly, alginate lyase enzyme-high viscosity alginate (viscosity 144 cP, condition 1% w/v in water @ 25° C.) solution was also prepared in 0.01 M phosphate buffer of pH 6.5 with final concentrations of 5 U/ml and 1.5% w/v respectively. Both the solutions were incubated at 4° C. for 15 mins, before dropping into 2% w/v calcium chloride solution to get calcium ion-crosslinked alginate microspheres loaded with alginate lyase enzyme. The crosslinked microspheres were washed three times in deionized water for 1 min each. The microspheres prepared in the acetate buffer showed a spherical shape (FIG. 7 (a)). On the other hand, microspheres obtained from phosphate buffer were irregularly shaped and partially degraded (FIG. 7 (b)). These results indicate that the low pH reduced the catalytic activity of the enzyme and prevented degradation of alginate, thereby aiding in getting the spherical microspheres. This method of making microspheres increases the processing window which may help in upscaling the production of the alginate microspheres loaded with the alginate lyase enzyme, by minimizing the degradation of alginate by the alginate lyase in the precursor solution. These two microspheres were incubated in 0.01 M phosphate buffer and/or -supplemented with 0.1 N NaOH to achieve pH 6.5 (in case of precursor solution pre-treated with acetate buffer) for 72 hours. The acetate buffer treated alginate-alginate lyase microspheres was completely degraded with no visible sign of residues as shown in FIG. 7 (c). On the other hand, phosphate buffer treated alginate-alginate lyase microspheres showed some white residues as observed in FIG. 7 (d). The degradation of these particles was also determined using UV-visible spectroscopy, wherein the degraded product of the alginate microspheres was determined by its absorbance at 235 nm. It was observed that acetate buffer treated alginate lyase-alginate $Ca^{2+}$-crosslinked microspheres showed a greater degradation when compared to phosphate buffered-treated equivalent microspheres (FIG. 7 (e)). These results indicate the pH dependent reversible activity of the alginate lyase enzyme, wherein the enzyme is partially and reversibly inhibited or modulated by exposing to low pH, which allow the loading of the desired amount of enzyme in the alginate microsphere without degrading the alginate matrix. The entrapped enzyme in the alginate microsphere is reversibly activated by exposing to optimum pH, resulting in the degradation of the alginate microspheres.

Example 6: Acidic pH-Dependent Reversible Activity of Alginate Lyase Enzyme

Alginate lyase enzyme and high viscosity alginate (viscosity 144 cP, condition 1% w/v in water @ 25° C.) was dissolved in 0.1 M acetate buffer (pH 4.0) and 0.01 M phosphate buffer (pH 6.5) with the final concentration of 1 U/ml and 0.1% w/v respectively. The samples names of the respective reactions are Alginate-AL A.B and Alginate-AL P.B. The temperature of these solutions was maintained at 1-4° C. and 37° C. for 30 mins. After the incubation, the reaction was terminated by adding 0.1N NaOH. Likewise, the alginate lyase enzyme was pre-incubated in acetate buffer for 15 mins, and then mixed with high viscosity alginate dissolved in M phosphate buffer and supplemented with 0.1 N NaOH to achieve the optimum pH 6.5 having the final concentration of 0.1 U/ml and 1% w/v respectively. The solution was incubated at 1-4° C. and 37° C. for 30 mins. After the incubation, the reaction was terminated by adding NaOH (Sample name is Alginate (P.B)-AL (A.B)). After terminating the reactions, the enzyme activity of the alginate lyase enzyme was determined by the absorbance of the degraded product at 235 nm wavelength.

Figure 8:
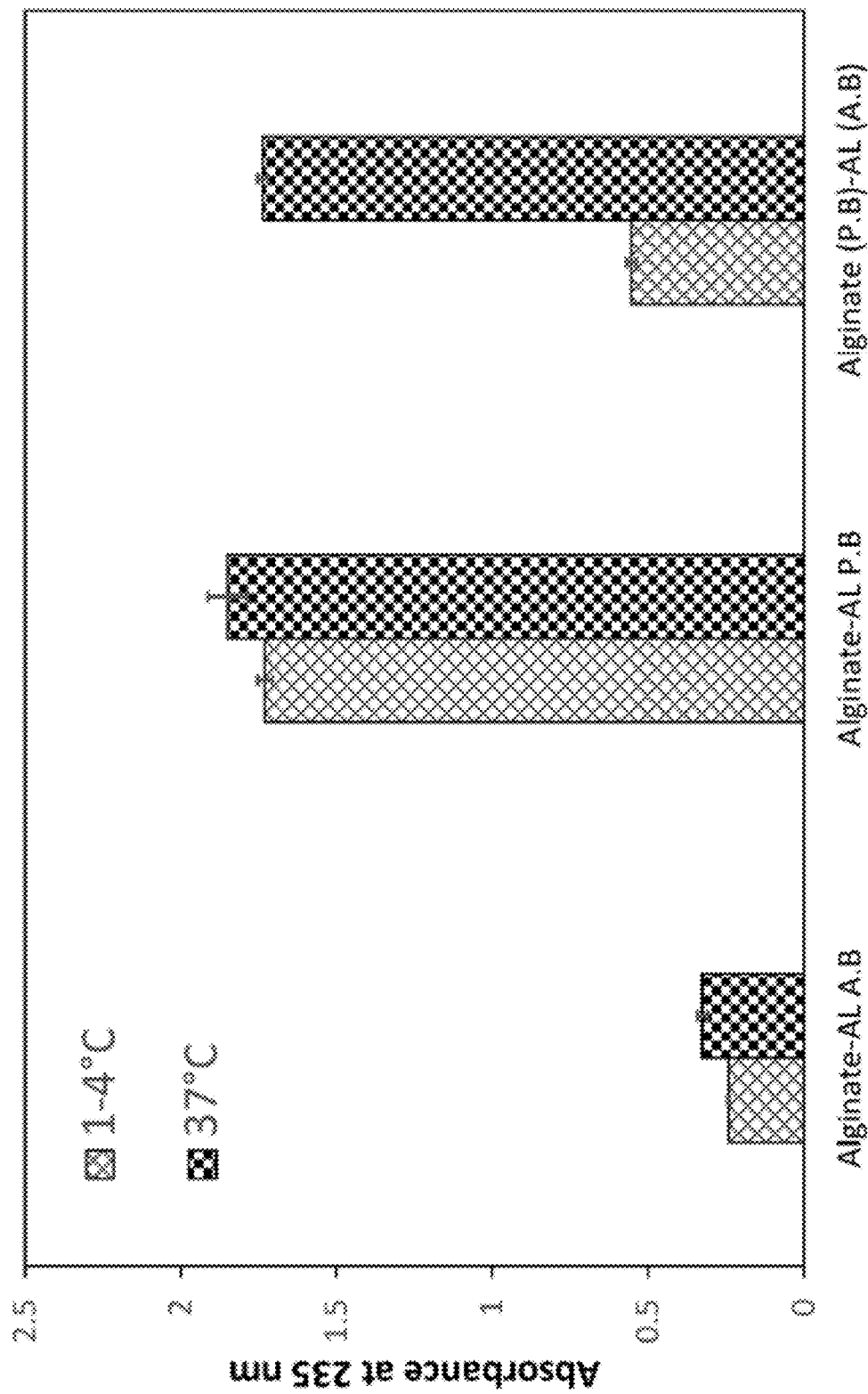
FIG. 8 illustrates absorbance spectra of degraded products obtained from alginate-alginate lyase (AL, 5 U) precursor solution in acetate buffer (A.B), pH 4 (Alginate-AL A.B), alginate-alginate lyase (AL) precursor solution in 0.01 M phosphate buffer (P.B), pH 6.5 (Alginate-AL P.B) and alginate lyase pre-incubated in A.B for 15 mins and mixed with alginate dissolved in 0.01M P.B ((Alginate (P.B)-AL (A.B)) for 30 mins at 1-4° C. and 37° C. respectively.
Figures 9A, 9B, 9C:
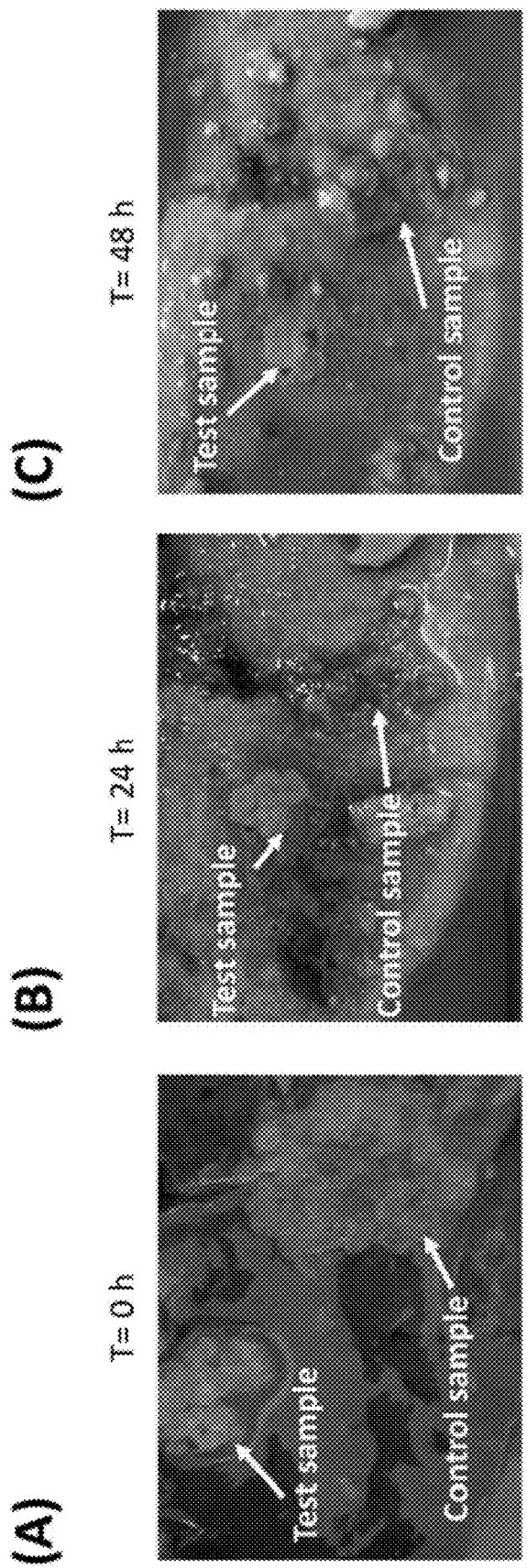
FIG. 9A illustrates ex vivo degradation studies of alginate lyase loaded calcium ion-complexed alginate particles in a liver model at 0 hours.
FIG. 9B illustrates ex vivo degradation studies of alginate lyase loaded calcium ion-complexed alginate particles in a liver model at 24 hours.
FIG. 9C illustrates ex vivo degradation studies of alginate lyase loaded calcium ion-complexed alginate particles in a liver model at 48 hours.

From FIG. 8, it was observed that enzyme activity of Alginate-AL A.B is reduced at 1-4° C. and 37° C., when compared to Alginate-AL P.B sample. Furthermore, it is observed from Alginate-AL P.B sample that there is negligible effect of low temperature on reducing the alginate lyase activity. Furthermore, the alginate lyase enzyme-pretreated with acetate buffer mixed with alginate dissolved in phosphate buffer (Alginate (P.B)-AL (A.B)) showed 4 times reduction in the enzyme activity at 4° C. when compared to Alginate-AL P.B sample. This indicates that acetate buffer partially reduced the activity of the enzyme at 1-4° C. Remarkably, the alginate lyase enzyme activity increases considerably at 37° C. and the levels were found to be similar to Alginate-AL P.B sample. This increase in the activity showed the pH-dependent reversible alginate lyase activity, wherein the enzyme is partially and reversibly inhibited or modulated by exposing to low pH, which is restored by changing to the optimum pH of the solution. These results are further supported by FIG. 9A-9C.

Example 7: Lyophilization of $Ca^{2+}$-Crosslinked Alginate Microspheres Loaded with Alginate Lyase Enzyme Using Cryoprotectants PVP 40 kDa (0.5%, W/V) and Trehalose (0.5%, W/V)

Figure 10:
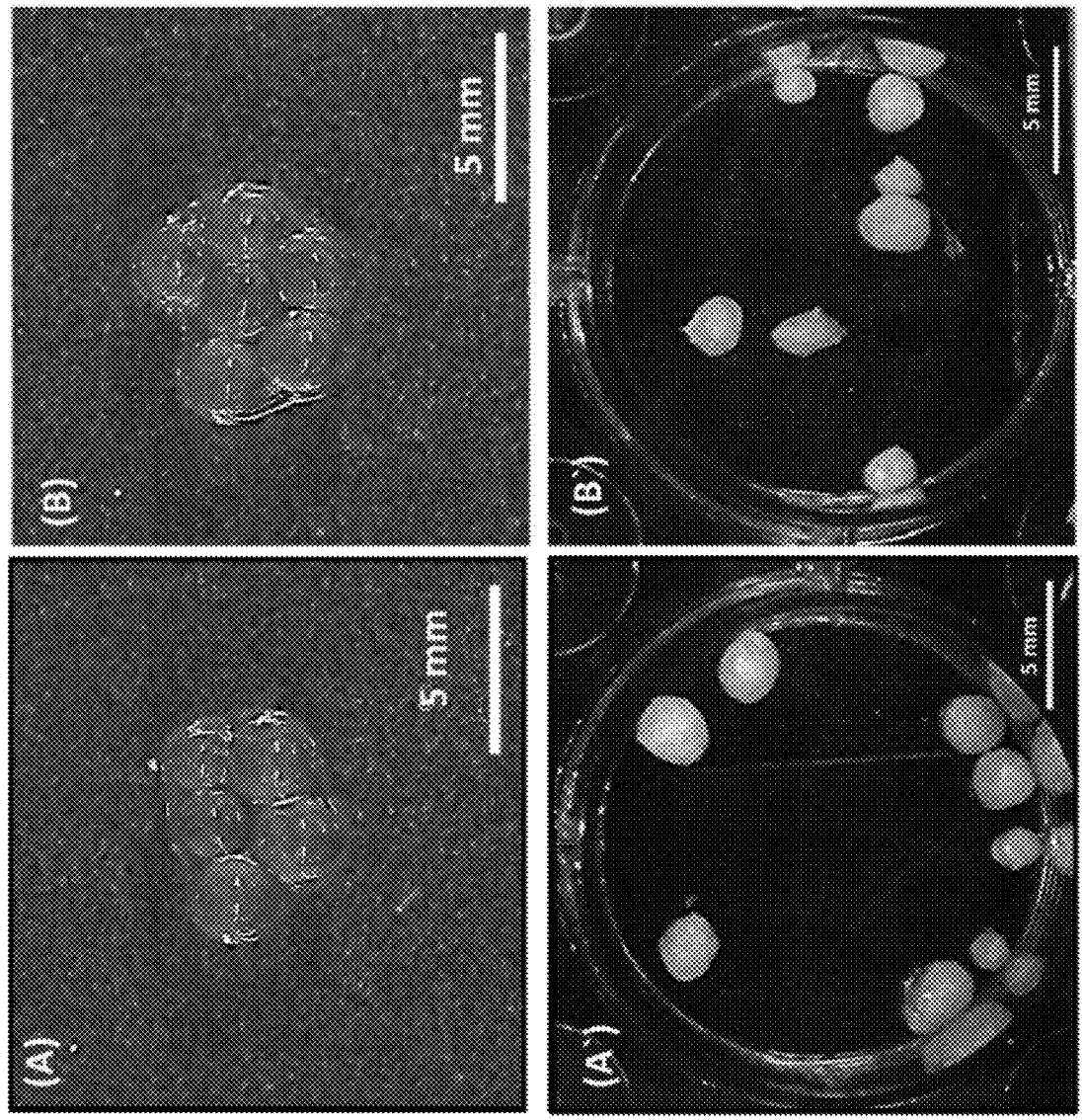
FIG. 10 illustrates $Ca^{2+}$-crosslinked alginate microspheres loaded with 1 U alginate lyase enzyme and 0.5% w/v-PVP 40 KDa+0.5% w/v trehalose (A and A') and 0.5% w/v hydroxypropyl-β cyclodextrin (B and B'), before and after lyophilization respectively.

Dissolve high viscosity (Viscosity 144 cP, condition 1% w/v in water @ 25° C.) 1.5% w/v sodium alginate, PVP 40 kDa (0.5% w/v), trehalose (0.5% w/v) in deionized water and stir on a magnetic stirrer for half an hour/45 min at 1-4° C. to obtain a homogenous dispersion. Then, added 5 U alginate lyase enzyme into the dispersion and mix for 1 min. This solution added dropwise to 2% w/v $CaCl_2$) containing PVP 40 kDa (0.5% w/v) and trehalose (0.5% w/v), and stir for 15 minutes to get PVP 40 kDa and trehalose containing $Ca^{2+}$-crosslinked alginate microspheres loaded with alginate lyase enzyme. These microspheres were further washed with deionized water 3 times for 1 min. each and exposed to liquid nitrogen for 30 sec to 2 minutes. The frozen microspheres were lyophilized for 24 hours using a lyophilizer which was set at −57° C. under ultra-high vacuum. From FIGS. 10A and 10A', the freeze dried or lyophilized microspheres showed no change in the shape when compared to non-lyophilized microspheres, thus indicating preservation of shape of the microspheres.

Example 8: Lyophilization of $Ca^{2+}$-Crosslinked Alginate Microspheres Loaded with Alginate Lyase Enzyme Using Cryoprotectants Hydroxypropyl-β-Cyclodextrin (0.5%, W/V)

Dissolve high viscosity (144 cP, condition 1% w/v in water @ 25° C.) 1.5% w/v sodium alginate and Hydroxypropyl-β-cyclodextrin (0.5%, W/V) in deionized water and stir on a magnetic stirrer for half an hour/45 min at 1-4° C. to obtain a homogenous dispersion. Then, added 5 U alginate lyase enzyme into the dispersion and mix for 1 min. This solution added dropwise to 2% w/v $CaCl_2$) containing 0.5% w/v of Hydroxypropyl-β-cyclodextrin and stir for minutes to get Hydroxypropyl-β-cyclodextrin containing $Ca^{2+}$-crosslinked alginate microspheres loaded with alginate lyase enzyme. These microspheres were further washed with deionized water 3 times for 1 min. each and exposed to liquid nitrogen for 30 sec to 2 minutes. The frozen microspheres were lyophilized for 24 hours using a lyophilizer which was set at −57° C. under ultra-high vacuum. From FIGS. 10B and 10B', the freeze dried or lyophilized microspheres showed no change in the shape when compared to non-lyophilized microspheres, thus indicating preservation of shape of the microspheres.

Figure 11:
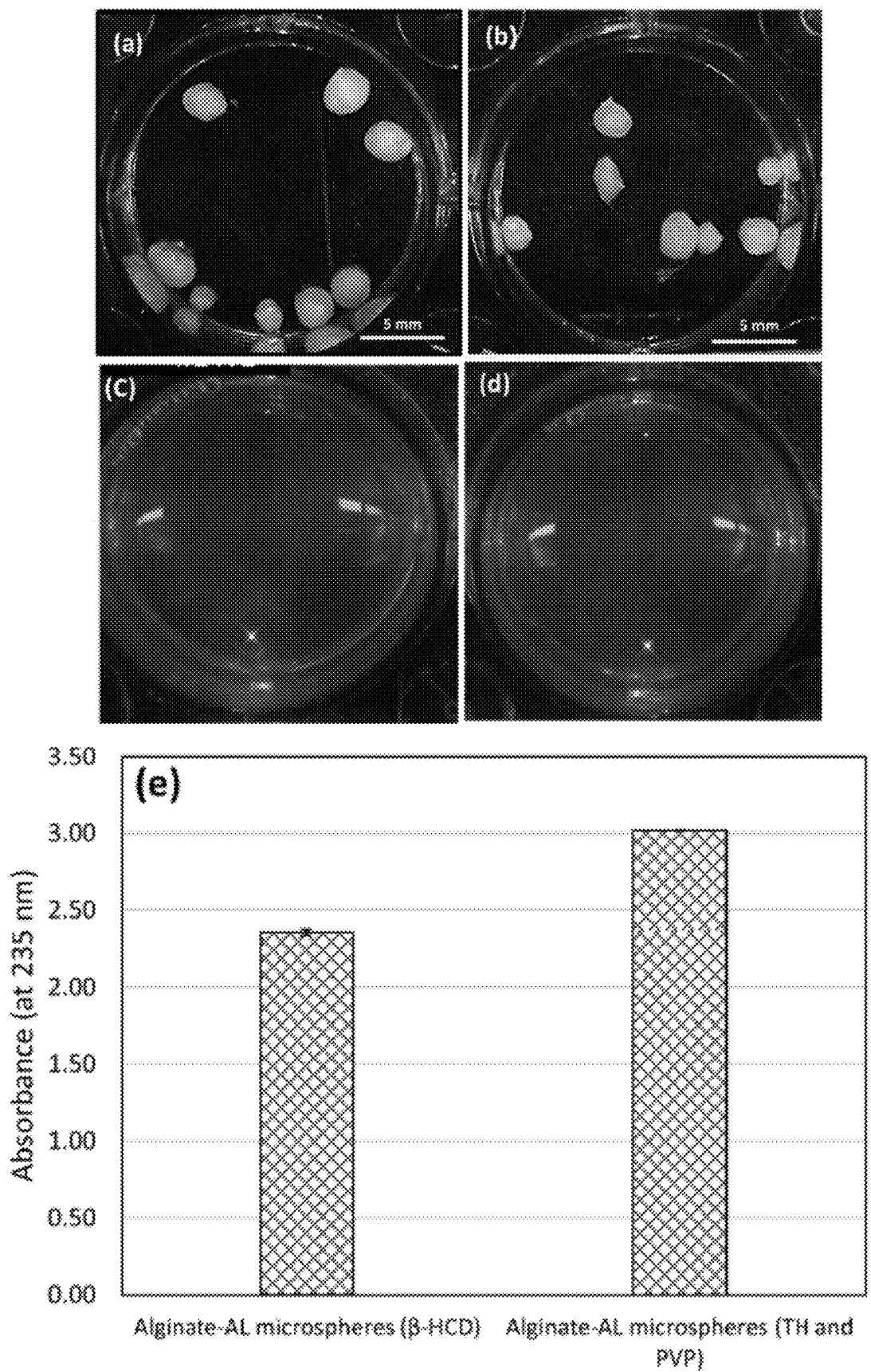
FIG. 11 illustrates microscopic images of lyophilized $Ca^{2+}$-crosslinked alginate microspheres loaded with 5 U alginate lyase enzyme and (a) 0.5% w/v-PVP 40 kDa+0.5% w/v trehalose and (b) 0.5% w/v hydroxypropyl-β cyclodextrin (before degradation); (c) and (d) samples are corresponding to (a) and (b) respectively, degraded in 0.01 M phosphate buffer (pH 6.5) after 72 hours of incubation at 37° C. Absorbance spectra of the degraded product of the samples (c) and (d) in 0.01 M phosphate buffer (pH 6.5) after 72 hours of incubation at 37° C. (e).

Example 9: Degradation of Lyophilized $Ca^{2+}$-Crosslinked Alginate Microspheres Loaded with Alginate Lyase Enzyme Containing PVP 40 kDa (0.5%, W/V) and Trehalose (0.5%, W/V) Cryoprotectants Dissolve high viscosity (Viscosity 144 cP, condition 1% w/v in water @ 25° C.) 1.5% w/v sodium alginate, PVP 40 kDa (0.5% w/v), trehalose (0.5% w/v) in deionized water and stir on a magnetic stirrer for half an hour/45 min at 1-4° C. to obtain a homogenous dispersion. Then, added 5 U alginate lyase enzyme into the dispersion and mix for 1 min. This solution was added dropwise to 2% w/v $CaCl_2$) containing PVP 40 kDa (0.5% w/v) and trehalose (0.5% w/v), and stirred for 15 minutes to get PVP 40 kDa and trehalose containing $Ca^{2+}$-crosslinked alginate microspheres loaded with alginate lyase enzyme. These microspheres were further washed with deionized water 3 times for 1 min. each and exposed to liquid nitrogen for 30 sec to 2 minutes. The frozen microspheres were lyophilized for 24 hours using a lyophilizer which was set at −57° C. under ultra-high vacuum. FIG. 11 (a) shows the freeze dried or lyophilized microspheres. The lyophilized microspheres were suspended in 0.01 M phosphate buffer (pH 6.5) and incubated at 37° C. for 72 hours. It was observed that the suspended microsphere was degraded, and the turbidity is observed as shown in FIG. 11 (c). FIG. 11 (e) shows the absorbance spectra of degraded product of lyophilized self-degradable alginate microspheres.

Example 10: Degradation of Lyophilized $Ca^{2+}$-Crosslinked Alginate Microspheres Loaded with Alginate Lyase Enzyme Containing Hydroxypropyl-β-Cyclodextrin (0.5%, W/V) Cryoprotectant Dissolve high viscosity (144 cP, condition 1% w/v in water @ 25° C.) 1.5% w/v sodium alginate and Hydroxypropyl-β-cyclodextrin (0.5% w/v) in deionized water and stir on a magnetic stirrer for half an hour/45 min at 1-4° C. to obtain a homogenous dispersion. Then, added 5 U alginate lyase enzyme into the dispersion and mix for 1 min. This solution was added dropwise to 2% w/v $CaCl_2$) containing 0.5% w/v of Hydroxypropyl-β-cyclodextrin and stirred for 15 minutes to get Hydroxypropyl-β-cyclodextrin containing $Ca^{2+}$-crosslinked alginate microspheres loaded with alginate lyase enzyme. These microspheres were further washed with deionized water 3 times for 1 min. each and exposed to liquid nitrogen for 30 sec to 2 minutes. The frozen microspheres were lyophilized for 24 hours using a lyophilizer which was set at −57° C. under ultra-high vacuum. FIG. 11 (b) shows the freeze dried or lyophilized microspheres. The lyophilized microspheres were suspended in 0.01 M phosphate buffer (pH 6.5) and incubated at 37° C. for 72 hours. It was observed that the suspended microsphere was degraded, and the turbidity is observed as shown in FIG. 11 (d). FIG. 11 (e) shows the absorbance spectra of degraded product of lyophilized self-degradable alginate microspheres.

Example 11: Ex Vivo Degradation of Alginate Lyase Loaded Divalent Metal Ion-Complexed Alginate Particles In this test, 5 U of alginate lyase enzyme was loaded into the calcium ion-complexed alginate particles and control particles (without enzyme) and placed it onto the liver (bovine) immersed in saline. To evaluate the degradation of particles, the liver was kept in an oven with a temperature set at 37±1° C. and morphological change in the particles was observed for 48 hours. From FIG. 9, the alginate lyase loaded alginate particles lost the shape in 48 hours and a film of white residue can be observed. On the other hand, the control particles maintain the shape for 48 hours. A black film on the control particles can be observed which might be the formation of biofilm.

Example 12: In Vitro Biocompatibility of Alginate Particles

Figure 12:
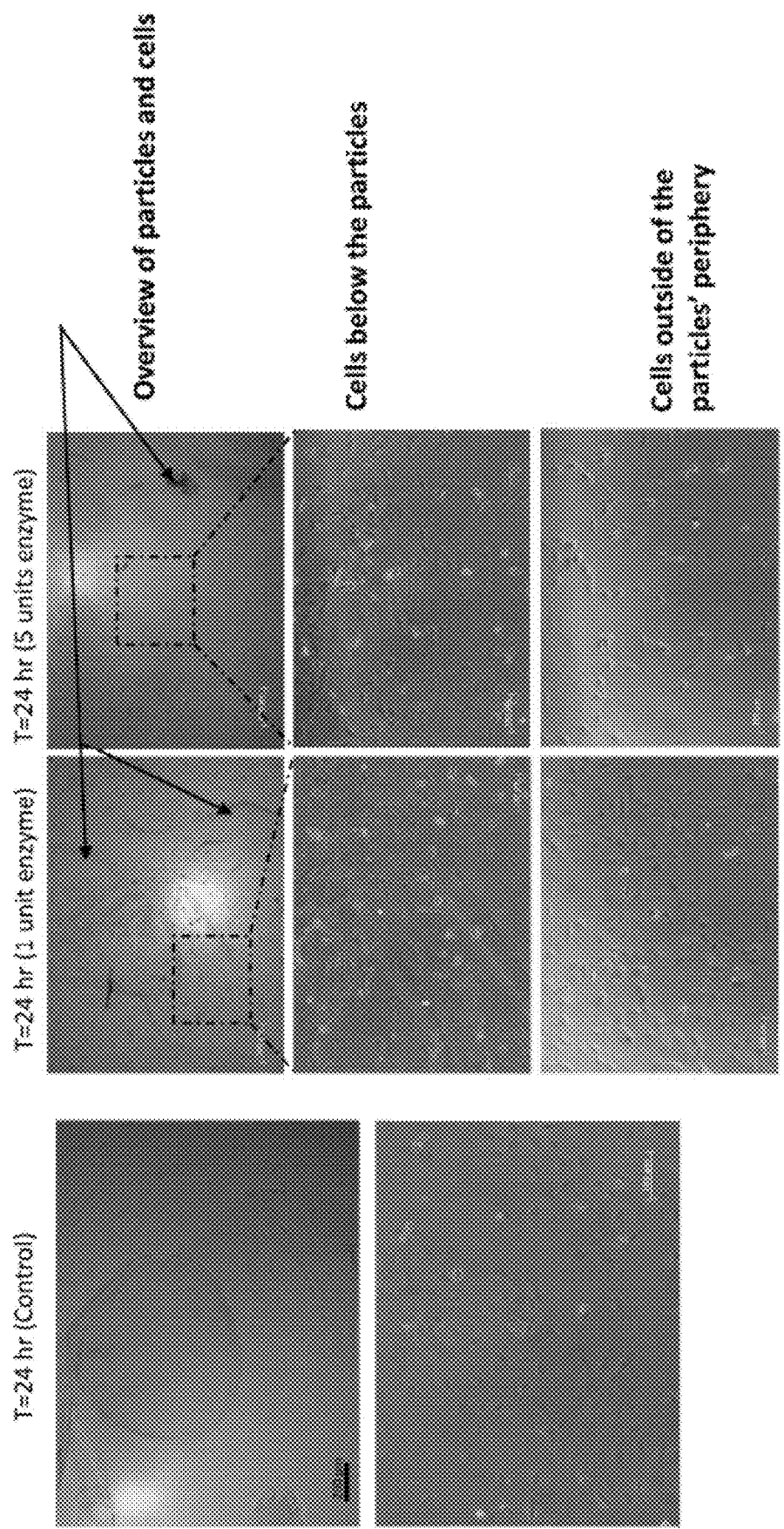
FIG. 12 illustrates in vitro biocompatibility of alginate lyase loaded-calcium ion alginate particles.

Two different calcium ion-complexed alginate particles were prepared loaded with 1 U and 5 U of alginate lyase enzyme. To evaluate the biocompatibility of the particles, the morphology and viability of the cells were observed through a light microscope as shown in FIG. 12. Cells were seeded in a 24 well-plate with the cell density of $10^4$ cells per ml. Cells were cultured under 37° C., 5% $CO_2$, and 95% relative humidity in alpha-MEM containing 10% fetal bovine serum and 1% penicillin and streptomycin. At least 10 particles of size 2-3 mm were added in the 24 well-plate and incubated for 24 hr. In control samples, intact particles were observed with no detrimental influence on the viability and morphology of osteoblast cells. Alginate particles loaded with 5 U of alginate lyase enzyme were completely degraded (indicated by the debris of the degraded alginate particles), whereas 1 U of alginate lyase enzyme loaded alginate particles were irregularly shaped. The cells are viable with flattened morphology below the degraded particles. This data demonstrated the in vitro biocompatibility of the alginate lyase loaded calcium-complexed alginate particles.

Example 13: Degradation of Lyophilized $Ca^{2+}$-Crosslinked Alginate Lyase-Alginate Microspheres in from Alginate-Alginate Lyase Precursor Solution Pretreated with Alkaline pH (Carbonate Buffer, pH 10)

Figure 13:
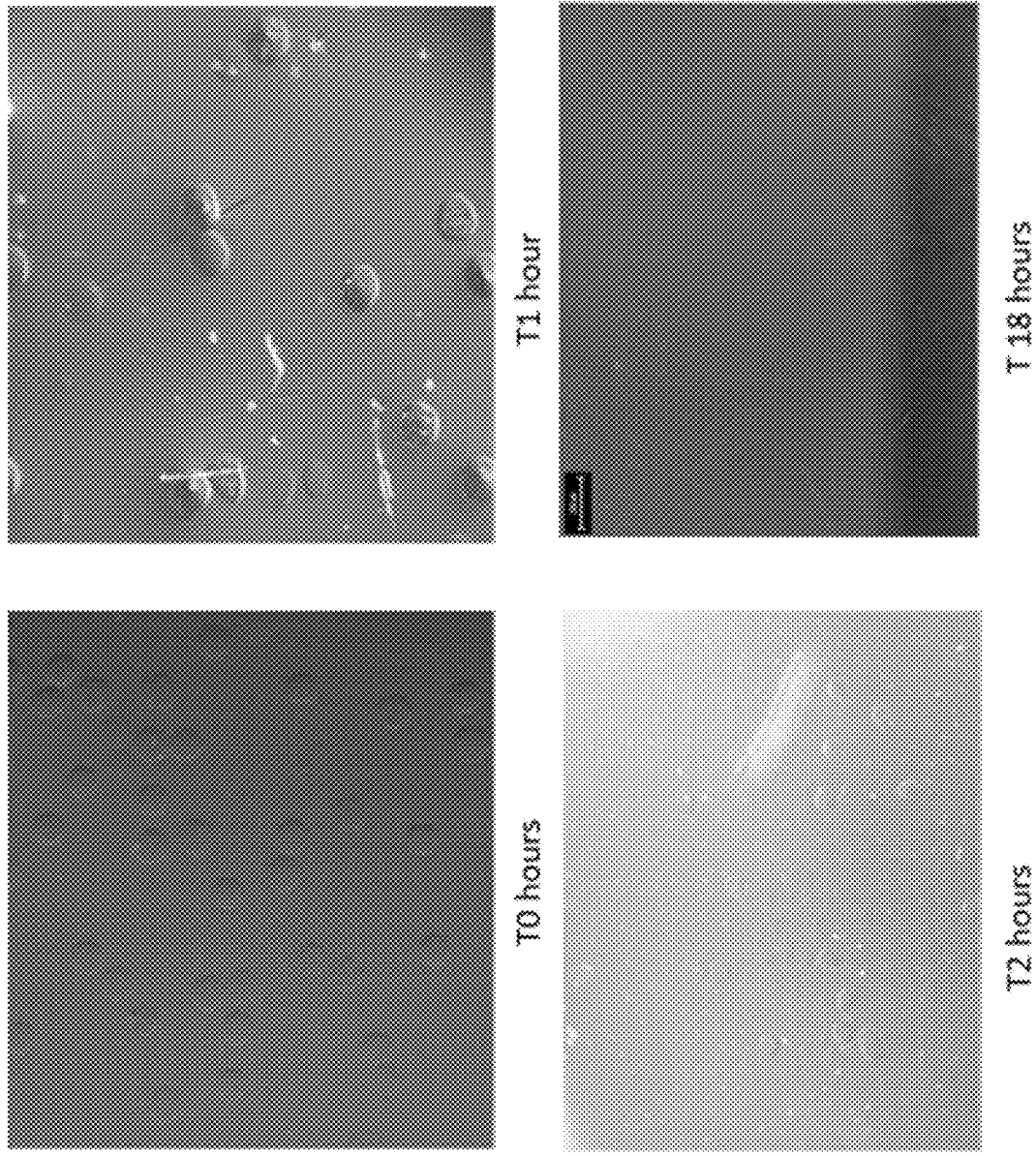
FIG. 13 illustrates post lyophilized resorbable beads rehydrated in saline at physiological conditions observed at 4 time points.

4% w/v Pronova alginate (G/M<1, molecular weight approx. 75 kDa-200 kDa) in carbonate buffer (pH 10 and 0.1 M) were dissolved and stirred on a magnetic stirrer for half an hour/45 min at 1-4° C. to obtain a homogenous dispersion. Then, 100 mM of ethylenediaminetetraacetic acid calcium disodium salt hydrate and alginate lyase were added to obtain the precursor solution containing final concentration of 2% w/v alginate, 0.05 U/ml of alginate lyase, and 50 mM of ethylenediaminetetraacetic acid calcium disodium salt hydrate. Through the microfluidics platform, the droplets of precursor solution of size approx. 200 µm were generated using oil-in-water emulsion technique and exposed to an acidic solution of 2% w/v acetic acid, oil+ 0.05% surfactant to crosslink the beads, wherein $Ca^{2+}$ ion releases by the ionization of Ca-EDTA and binds to egg-box alginate droplets to generate $Ca^{2+}$-crosslinked alginate beads loaded with alginate lyase enzyme. To isolate the crosslinked alginate beads of size approx. 200 µm, the droplets were treated with a droplet breaking solution and further washed with deionized water to remove the oil and surfactant. These beads were further crosslinked in 2% w/v $CaCl_2$) solution for 5 mins, thereafter, again washed with deionized water to remove the residual calcium chloride solution. Furthermore, the beads were stored in acetate buffer (0.1 M, pH 4.0) containing trehalose and β-hydroxy-cyclodextrin for at least 6 hours before being subjected to lyophilization. After lyophilization, the beads were rehydrated or reconstituted in a saline solution and the degradation was evaluated for 18 hours in static solution condition. From FIG. 13, T1 hours shows some minor breakdown, shape change with loss of uniformity, and small particle agglomeration (<10 µm) appearing in the solution. T2 hours follows this trend with increased surface and shape damage, agglomeration of small particles in solution has increased. T18 hours showed a completely bead free solution with no agglomeration observed.

Figure 14:
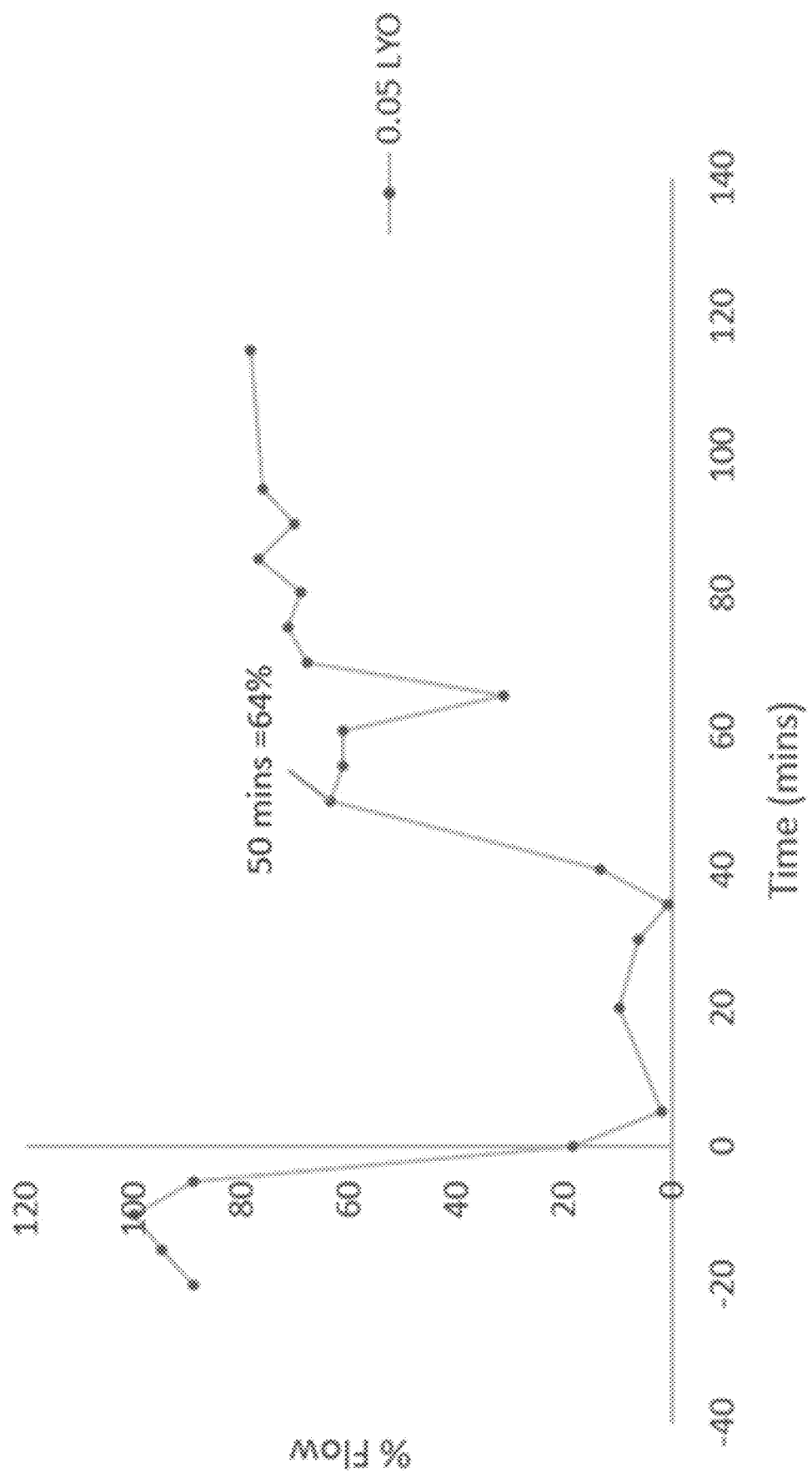
FIG. 14 is a chart showing re-establishment of flow following embolization and subsequent degradation of rehydrated resorbable alginate beads containing 0.05 U of alginate lyase in an Elastrat Liver Model.

Example 14: Degradation of Post Lyophilized Resorbable Alginate Beads Reconstituted in Saline Solution in Elastrat Liver Model Herein, the lyophilized resorbable alginate beads containing 0.05 U of alginate lyase were reconstituted in saline solution and injected in the Elastrat Liver Model to see the occlusion efficiency of these beads and degradation of beads over time by quantifying the flow restoration of saline. FIG. 14 depicts that the flow rate at 0 min (T=0) was reduced by >90% for 38 mins after injections of beads in the liver model channel. By 50 mins, 64% flow was restored, and, after about 2 hours, the flow rate was restored by 80%. These results indicate a greater degradation rate was observed in a dynamic flow condition when compared to static conditions as given in Example 13.

Figure 15:
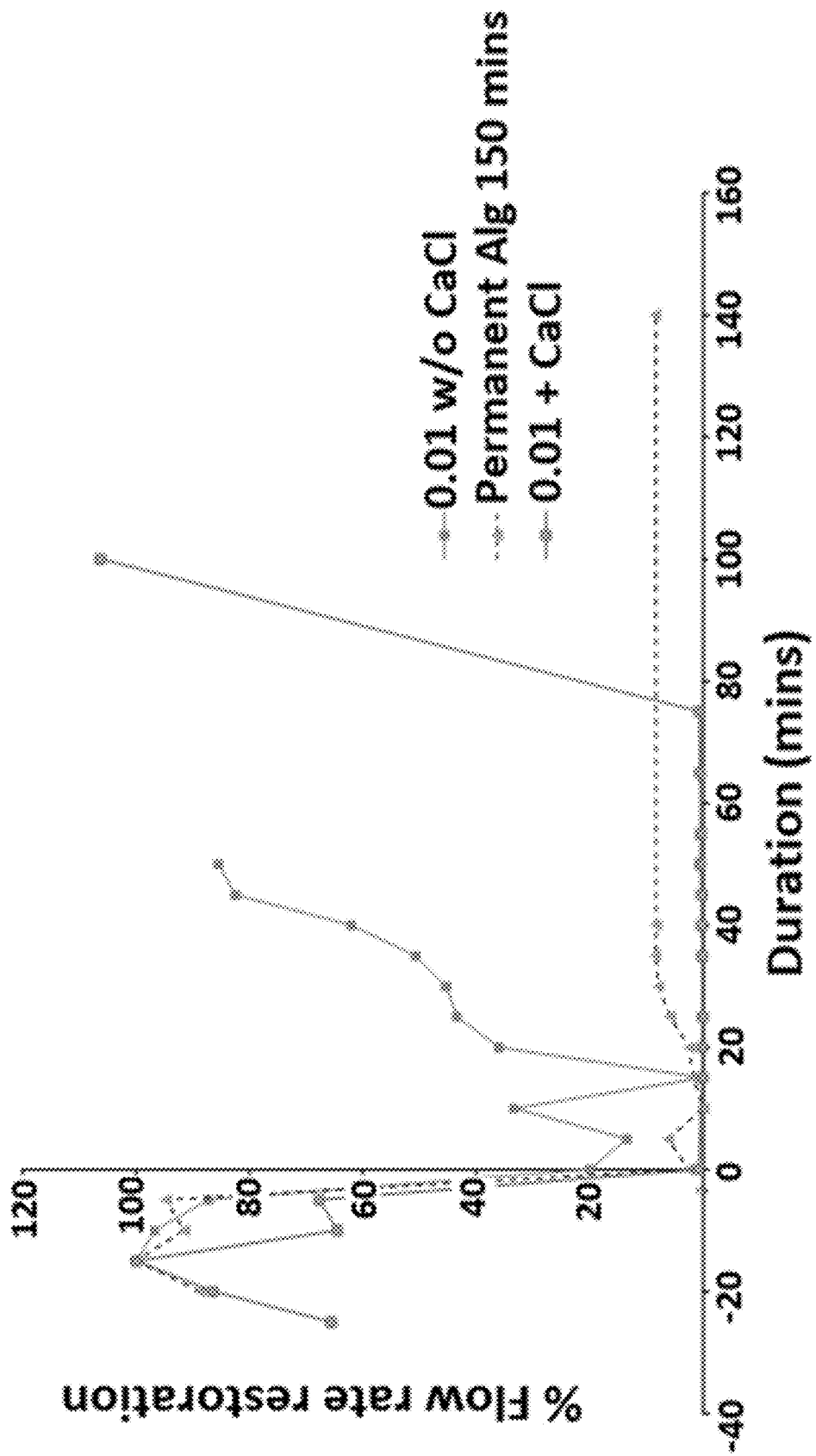
FIG. 15 is a chart showing re-establishment of flow following embolization and subsequent degradation of rehydrated resorbable alginate beads containing 0.01 U (without (w/o) addition crosslinking in $CaCl_2$)), with additional crosslinking in $CaCl_2$) solution (0.01 U+$CaCl_2$)), and permanent beads in the Elastrat Liver Model.

Example 15: Evaluation of $Ca^{2+}$ Ion Crosslinking on the Degradation Behavior of Resorbable Alginate Beads in Elastrat Liver Model The effect of calcium ion crosslinking on the degradation rate of resorbable alginate is shown in FIG. 15. Resorbable alginate beads containing 0.01 U of alginate lyase that were crosslinked by $Ca^{2+}$ ion released by the ionization of Ca-EDTA under acidic conditions (0.01 without (w/o) $CaCl_2$)) showed an inefficient reduction of the flow rate of saline after injection into the liver model, indicating the presence of deformed alginate beads due to the alginate lyase degrading activity. By 40 mins, −80% flow rate was achieved, thereby indicating the rapid degradation of resorbable alginate beads. To reduce the activity of the enzyme, these beads were further crosslinked in 2% w/v $CaCl_2$) solution for 5 mins. These particles were injected into the liver model and a complete reduction in the flow rate was observed until 70 mins, thereafter an accelerated restoration of flow was achieved by 100 mins. On the other hand, permanent beads (only crosslinked with Ca-ETDA) showed a continuous reduction in the flow rate indicating no degradation or disintegration of alginate beads observed over a period of 140 min. These results demonstrated that $Ca^{2+}$ crosslinking is dependent on alginate lyase activity, thus controlling the degradation of alginate beads.

Example 16: Alkaline pH Dependent Reversible Activity of Alginate Lyase

Figure 16:
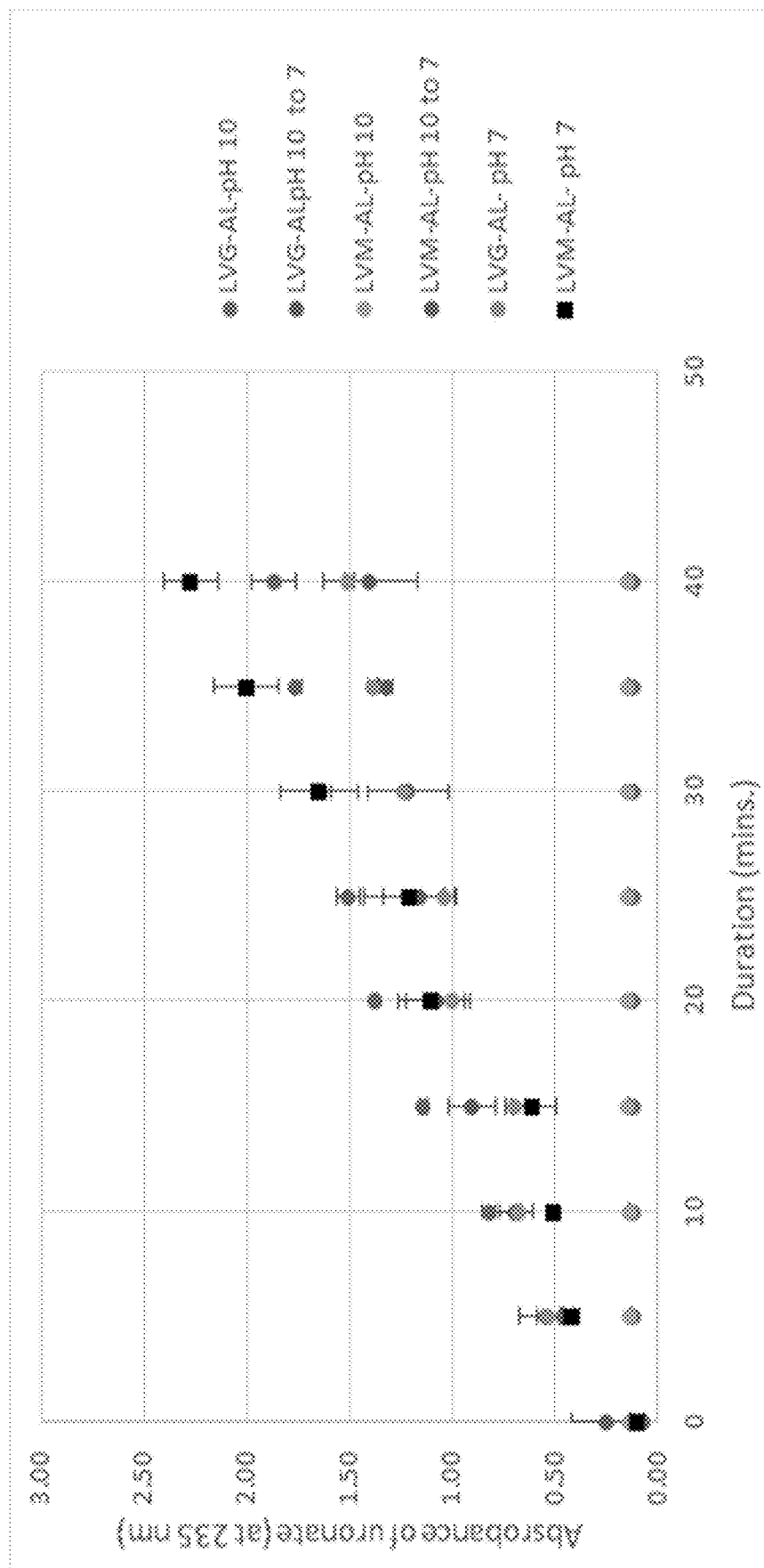
FIG. 16 is a chart showing alkaline pH dependent reversible alginate lyase activity.

Alginate lyase enzyme and LVG alginate (G/M>1, molecular weight approx. 75 kDa-200 kDa) or LVM alginate (G/M<1, molecular weight approx. 75 kDa-200 kDa) were dissolved in 0.1 M carbonate buffer (pH 10.0) and 0.01 M phosphate buffer (pH 6.5) with the final concentration of 0.1 U/ml and 0.1% w/v respectively. The sample names of the respective reactions are LVM- or -LVG-AL pH 10 and LVG-Alginate-AL pH 7. Likewise, the alginate lyase enzyme was pre-incubated in pH 10.0, 0.1 M carbonate buffer for 15 mins, and then mixed with LVG alginate (G/M>1, molecular weight approx. 75 kDa-200 kDa) or LVM alginate (G/M<1, molecular weight approx. 75 kDa-200 kDa) in 0.01 M phosphate buffer to achieve the optimum pH 6.5 having the final concentration of 0.1 U/ml and 0.1% w/v respectively. The sample names of the respective reactions are LVM- or -LVG-AL pH 10 to 7. All the above-mentioned samples were incubated and the enzyme activity of the alginate lyase enzyme was determined by the absorbance of the degraded product at 235 nm wavelength (FIG. 16).

Figure 17:
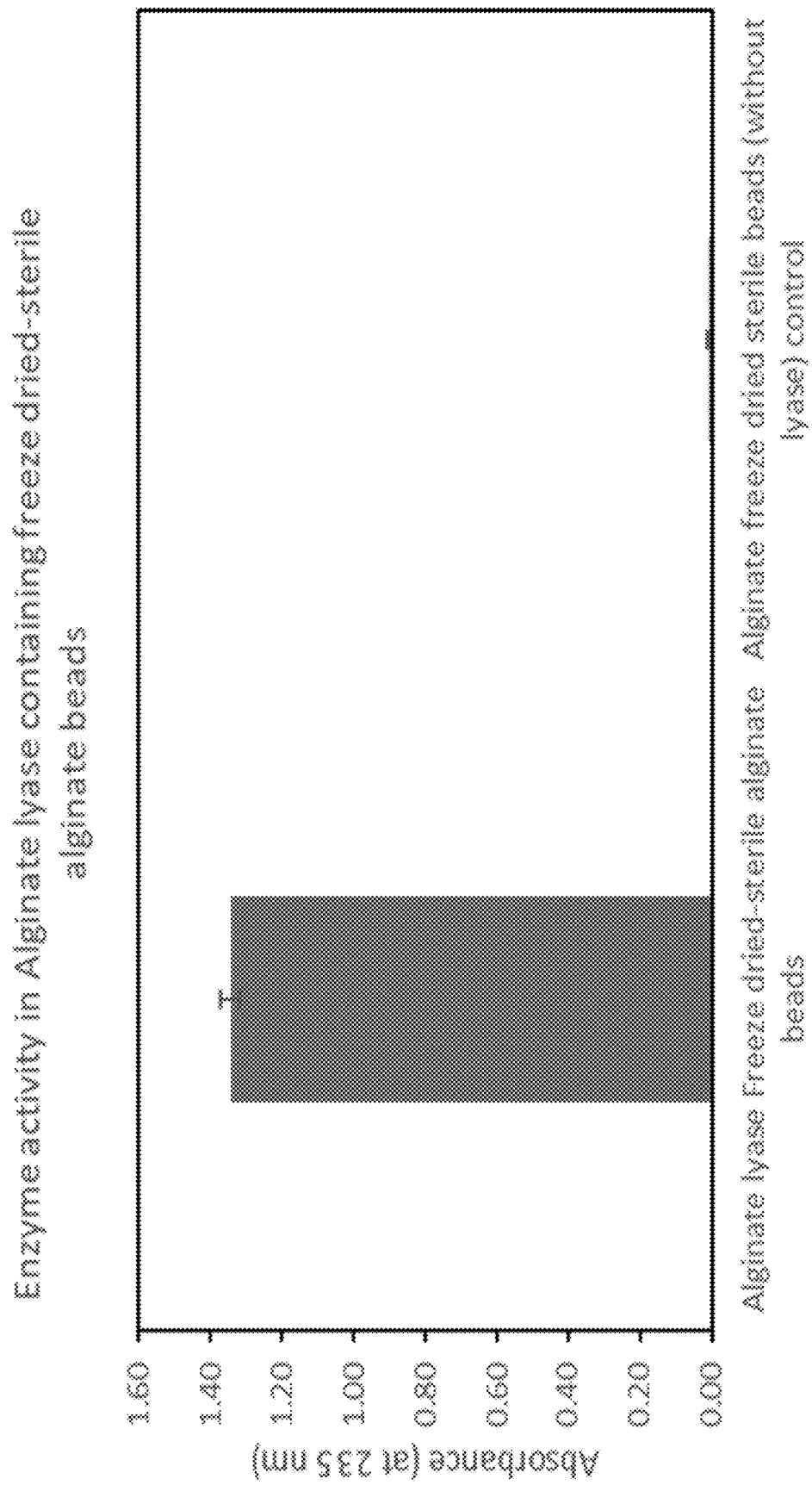
FIG. 17 is a graph showing the effect of e-beam sterilization on the activity of alginate lyase enzyme (0.05 U) encapsulated into $Ca^{2+}$-crosslinked alginate beads (beads without enzyme shown as a control).

Example 17: Effect of Sterilization on Alginate Beads Loaded with 0.05 U of Alginate Lyase Enzyme The lyophilized alginate beads containing 0.05 U of alginate were sterilized using kGy e-beam and subjected to self-degradation in saline solution at physiological conditions (pH 7 and temperature 37° C.) for 24 hours. FIG. 17 shows the presence of alginate lyase activity as indicated by an increase in absorbance recorded at 235 nm when compared to freeze dried sterile alginate beads control (without lyase). These results demonstrated that resorbable beads can be freeze dried, sterilized, and degraded on reconstitution in an aqueous solution (here, saline) under physiological conditions wherein the sterilization does not affect the alginate lyase enzyme activity.

What is claimed is:

1. An alginate microsphere capable of self-degradation upon rehydration, comprising:
   an alginate lyase enzyme pre-treated by varying temperature, by varying pH, and/or with a metal-ion enzyme inhibitor;
   alginate molecules having one or both of (i) a predetermined molecular weight, and (ii) a predetermined ratio of β-D-Mannuronic acid (M) blocks to α-L-Guluronic acid (G) blocks; and
   a divalent metal-ion crosslinking the alginate molecules, wherein the alginate microsphere is substantially free of water and/or sterilized.

2. The alginate microsphere of claim 1, wherein the degradation of alginate microsphere is controlled by one or more of the pre-treatment of the alginate lyase enzyme, an amount of the alginate enzyme in the microsphere, the predetermined molecular weight of the alginate molecule, and the predetermined ratio of M:G blocks of the alginate molecules, and a composition of gelling bath, including an amount and or charge of one or more ions in the gelling bath.

3. The alginate microsphere of claim 1, wherein at least one of (i)-(iii) applies:
   (i) the metal-ion enzyme inhibitor is a reversible inhibitor selected from the group consisting of $Cu^{2+}$, $Zn^{2+}$, and $Fe^{3+}$,
   (ii) the pre-treatment of the alginate enzyme in the precursor solution allows mixing of a predetermined amount of enzyme (measured in units, U) with the alginate molecules, and
   (iii) an activity of the alginate lyase enzyme is modulated by adjusting one or more of a pH of a gelling bath, a temperature of the gelling bath, and an amount of the metal-ion enzyme inhibitor in the alginate microsphere.

4. The alginate microsphere of claim 1, wherein at least one of (i)-(v) applies:
   (i) the predetermined molecular weight of the alginate molecules is in a range of greater than about 100 kDa to less than about 800 kDa,
   (ii) the predetermined ratio of M:G blocks is about 50:50, about 55:45, about 60:40, about 65:35, about 70:30, about 75:25, about 80:20, about 85:15, about 90:10, or about 95:5,
   (iii) the predetermined ratio of M:G blocks is about 50:50, about 45:55, about 40:60, about 35:65, about 30:70, about 25:75, about 20:80, about 15:85, about 10:90, or about 5:95,
   (iv) an activity of the alginate lyase enzyme is between about 0.05 mU (milliunits) and about 2.5 mU per microsphere, and
   (v) an activity of the alginate lyase enzyme is between about 0.05 nU (nanounits) and about 0.05 mU per microsphere.

5. The alginate microsphere of claim 4, wherein at least one of (a)-(d) applies:
   (a) the alginate microsphere of (ii) degrades over a period of less than about 5 days or greater than about 2 days,
   (b) the alginate microsphere of (iii) degrades over a period of between about 5 days and about 30 days,
   (c) the alginate microsphere of (iv) degrades over a period of less than about 5 days, and
   (d) the alginate microsphere of (v) degrades over a period of between about 5 days and about 30 days.

6. The alginate microsphere of claim 1, wherein at least one of (i)-(vii) applies:
   (i) the microsphere further comprises a bioactive agent,
   (ii) the microsphere further comprises a cryoprotectant selected from the group consisting of hydroxypropyl-ß cyclodextrin, trehalose, polyvinyl pyrrolidone of 40 kDa (PVP 40 kDa), dextran (70 kDa molecular weight), glucose, lactose, maltodextrins, mannitol, glycols, and polyglycols,
   (iii) the alginate microsphere is lyophilized,
   (iv) a sphericity of the alginate microsphere is at least about 0.7, at least about 0.75, at least about 0.8, at least about 0.85, at least about 0.9, at least about 0.95, or at least about 0.99,
   (v) the alginate microsphere is sterilized, or the alginate microsphere is lyophilized and sterilized,
   (vi) a shelf-life of the alginate microsphere is at least about 3 months, at least about 6 months, at least about 12 months, at least about 18 months, at least about 24 months, at least about 36 months, at least about 48 months, or at least about 60 months when stored at a given temperature, and
   (vii) a lyophilized alginate microsphere is reconstituted in saline or saline-radiopaque contrast at physiological pH.

7. The alginate microsphere of claim 6, wherein at least one of (a)-(d) applies:
   (a) the bioactive agent of (i) comprises an anti-inflammatory agent, an anesthetic drug, an anti-cancer agent, or an anti-angiogenic agent,
   (b) a residual water content of the lyophilized alginate microsphere of (iii) is in the range of about 1% to about 3% by mass,
   (c) the sterilization of (v) comprises high energy radiation sterilization, gamma-ray sterilization, or e-beam sterilization, and
   (d) the given temperature of (vi) is between about 2° C. and about 8° C. or about room temperature (RT).

8. The alginate microsphere of claim 7, wherein the anti-inflammatory agent of (a) comprises hyaluronic acid having a molecular weight of between about 1 million (M) and about 5 M Daltons or the sterilization of (c) comprises between about 15 and about 25 kGy of gamma radiation from Cobalt 60 Isotope, or about 25 kGy of electron beam radiation in accordance with ISO 11137-1:2006.

9. A method of preparing an alginate microsphere capable of self-degradation upon rehydration, the method comprising:
   forming droplets from a precursor solution, the precursor solution comprising:
      an alginate lyase enzyme pre-treated by varying temperature, by varying pH, and/or with a metal-ion enzyme inhibitor; and
      alginate molecules having one or both of (a) a predetermined molecular weight, and (b) a predetermined ratio of β-D-Mannuronic acid (M) blocks to α-L-Guluronic acid (G) blocks;
   contacting the droplets with a gelling bath comprising a divalent metal-ion, thereby crosslinking the alginate molecules to form an alginate microsphere; and dehydrating, and optionally sterilizing, the alginate microsphere thereby substantially removing water from the microsphere.

10. The method of claim 9, wherein at least one of (i)-(x) applies:
   (i) the precursor solution comprises one or more cryoprotectants,
   (ii) the gelling bath comprises one or more cryoprotectants,
   (iii) the pH of alginate lyase enzyme in the precursor solution containing alginate lyase and alginate is in the range of pH 3.0 to 6.4,
   (iv) the metal-ion enzyme inhibitor is a reversible inhibitor selected from the group consisting of $Cu^{2+}$, $Zn^{2+}$, and $Fe^{3+}$,
   (v) the temperature of the precursor solution is in the range of 1-4° C.,
   (vi) the pre-treatment of the alginate enzyme in the precursor solution allows mixing of a predetermined amount of enzyme (measured in units, U) with the alginate molecules,
   (vii) an activity of the alginate lyase enzyme is modulated by adjusting one or more of a pH of the gelling bath, a temperature of the gelling bath, and an amount of the metal-ion enzyme inhibitor in the alginate microsphere,
   (viii) a pH of the gelling bath is less than about 6.5,
   (ix) a pH of the gelling bath is equal to or about equal to a pH of the precursor solution, and
   (x) the precursor solution and/or the gelling bath further comprises a bioactive agent.

11. The method of claim 9, wherein at least one of (i)-(iv) applies:
   (i) the dehydrating comprises lyophilizing the alginate microsphere,
   (ii) forming the droplets is performed using a method selected from the group consisting of drop casting, spray congealing/spray cooling, spray drying, microfluidic droplet production, and jet-cutting,
   (iii) a sphericity of the alginate microsphere is at least about 0.7, at least about 0.75, at least about 0.8, at least about 0.85, at least about 0.9, at least about 0.95, or at least about 0.99, and
   (iv) a shelf-life of the alginate microsphere is at least about 3 months, at least about 6 months, at least about 12 months, at least about 18 months, at least about 24 months, at least about 36 months, at least about 48 months, or at least about 60 months when stored at a given temperature.

12. The method of claim 10, wherein the cryoprotectant of (i) and (ii) is each independently selected from the group consisting of hydroxypropyl-ß cyclodextrin, trehalose, polyvinyl pyrrolidone of 40 kDa (PVP 40 kDa), dextran (70 kDa molecular weight), glucose, lactose, maltodextrins, mannitol, glycols, and polyglycols.

13. The method of claim 12, wherein at least one of (a)-(f) applies:
   (a) the concentration of the trehalose in the precursor solution (i) is about 0.1% w/v to about 20% w/v,
   (b) the concentration of the hydroxypropyl-ß cyclodextrin the precursor solution (i) or the gelling bath (ii) is about 0.1% w/v to about 2% w/v,
   (c) the concentration of the PVP 40 kDa in the precursor solution (i) is about 0.1% w/v to about 1% w/v,
   (d) the concentration of the dextran (molecular weight 70 kDa) in the precursor solution (i) is about 0.1% w/v to about 1% w/v,
   (e) the precursor solution (i) and the gelling bath (ii) comprise the same cryoprotectant, and
   (f) the precursor solution (i) and the gelling bath (ii) comprise the same cryoprotectant at equal or about equal concentrations.

14. The method of claim 11, wherein a residual water content of the lyophilized alginate microsphere is in the range of about 1% to about 3% by mass.

15. The method of claim 9, further comprising at least one step selected from (i)-(iv)
   (i) sterilizing the alginate microsphere or the alginate microsphere that has been dehydrated by lyophilization,
   (ii) storing the alginate microsphere for at least about 3 months, at least about 6 months, at least about 12 months, at least about 18 months, at least about 24 months, at least about 36 months, at least about 48 months, or at least about 60 months when stored at a given temperature,
   (iii) administering the alginate microsphere, or the alginate microsphere that has been dehydrated by lyophilization, to a subject, and
   (iv) reconstituting the alginate microsphere, or the alginate microsphere that has been dehydrated by lyophilization, using saline or saline-radiopaque contrast at physiological pH.

16. The method of claim 15, wherein at least one of (a)-(d) applies:
   (a) the sterilizing of (i) comprises high energy radiation sterilization, gamma-ray sterilization, or e-beam sterilization,
   (b) the sterilizing of (i) comprises between about 15 and about 25 kGy of gamma radiation from Cobalt 60 Isotope, or about 25 kGy of electron beam radiation in accordance with ISO 11137-1:2006,
   (c) the given temperature of (ii) is between about 2° C. and about 8° C., and
   (d) the given temperature of (ii) is about room temperature (RT).

17. The method of claim 9, wherein the degradation of alginate microsphere is controlled by one or more of the pre-treatment of the alginate lyase enzyme, an amount of the alginate enzyme in the microsphere, the predetermined molecular weight of the alginate molecule, and the predetermined ratio of M:G blocks of the alginate molecules, and a composition of gelling bath, including an amount and or charge of one or more ions in the gelling bath.

18. The method of claim 9, wherein at least one of (i)-(vii) applies:
   (i) the predetermined molecular weight of the alginate molecules is in a range of greater than about 100 kDa to less than about 800 kDa,
   (ii) the predetermined ratio of M:G blocks is about 50:50, about 55:45, about 60:40, about 65:35, about 70:30, about 75:25, about 80:20, about 85:15, about 90:10, or about 95:5,
   (iii) the predetermined ratio of M:G blocks is about 50:50, about 45:55, about 40:60, about 35:65, about 30:70, about 25:75, about 20:80, about 15:85, about 10:90, or about 5:95,
   (iv) the pre-treated alginate lyase enzyme is mixed in the precursor solution having enzyme activity ranging from 0.0025 U/mg to 1 U/mg of alginate,
   (v) the pre-treated alginate lyase enzyme is mixed in the precursor solution having enzyme activity ranging from 0.125 U/mg to 0.250 U/mg of alginate, (vi) the pre-treated alginate lyase enzyme is mixed in the precursor solution having enzyme activity ranging from 0.025 U/mg to 0.125 U/mg of alginate, and (vii) the pre-treated alginate lyase enzyme is mixed in the precursor solution having enzyme activity ranging from 0.0025 U/mg to 0.005 U/mg of alginate.

19. The method of claim 18, wherein at least one of (a)-(e) applies:

(a) the alginate microsphere (ii) degrades over a period of less than about 5 days or greater than about 2 days, (b) the alginate microsphere of (iii) degrades over a period of between about 5 days and about 30 days, (c) the alginate microsphere of (v) degrades over a period of less than about 5 days, (d) the alginate microsphere of (vi) degrades over a period of between about 5 days and about 30 days, and (e) the alginate microsphere of (vii) degrades over a period of greater than about 30 days.

20. The method of claim 10, wherein the bioactive agent of (x) comprises an anti-inflammatory agent, an anesthetic agent, anti-cancer agent, or an anti-angiogenic agent.

21. The method of claim 20, wherein the anti-inflammatory agent comprises hyaluronic acid having a molecular weight of between about 1 million (M) and about 5 M Daltons.

* * * * *